(12) United States Patent
Schneider et al.

(10) Patent No.: US 9,328,336 B2
(45) Date of Patent: May 3, 2016

(54) DGAT GENES AND METHODS OF USE FOR TRIGLYCERIDE PRODUCTION IN RECOMBINANT MICROORGANISMS

(71) Applicants: Jane C Schneider, San Diego, CA (US); Eric Moellering, La Jolla, CA (US); Erik Holtzapple, San Diego, CA (US); Soyan Lieberman, Solana Beach, CA (US); Gena Roy, San Diego, CA (US)

(72) Inventors: Jane C Schneider, San Diego, CA (US); Eric Moellering, La Jolla, CA (US); Erik Holtzapple, San Diego, CA (US); Soyan Lieberman, Solana Beach, CA (US); Gena Roy, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 622 days.

(21) Appl. No.: 13/652,934

(22) Filed: Oct. 16, 2012

(65) Prior Publication Data

US 2014/0106417 A1    Apr. 17, 2014

(51) Int. Cl.
   *C12N 9/10*    (2006.01)
   *C12P 7/64*    (2006.01)

(52) U.S. Cl.
   CPC .............. *C12N 9/1029* (2013.01); *C12P 7/64* (2013.01); *C12P 7/6436* (2013.01); *Y02P 20/52* (2015.11)

(58) Field of Classification Search
   None
   See application file for complete search history.

(56) References Cited

U.S. PATENT DOCUMENTS

| | | | |
|---|---|---|---|
| 5,447,858 A | 9/1995 | Key et al. | 435/172.3 |
| 5,464,758 A | 11/1995 | Gossen et al. | 435/69.1 |
| 5,639,952 A | 6/1997 | Quail et al. | 800/205 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,814,618 A | 9/1998 | Bujard et al. | 514/44 |
| 6,027,900 A | 2/2000 | Allnutt et al. | 435/6 |
| 6,252,140 B1 | 6/2001 | Mitra et al. | 800/298 |
| 6,316,224 B1 | 11/2001 | Xia | 435/69.1 |
| 6,379,945 B1 | 4/2002 | Jepson et al. | 435/243 |
| 6,410,828 B1 | 6/2002 | Armstrong et al. | 800/287 |
| 7,135,290 B2 | 11/2006 | Dillon | 435/6 |
| 7,198,937 B2 | 4/2007 | Xue et al. | 435/254.2 |
| 7,294,506 B2 | 11/2007 | Daniell et al. | 435/320.1 |
| 7,642,405 B2 | 1/2010 | Lee | 800/296 |
| 7,901,928 B2 | 3/2011 | Yadav et al. | 435/254.21 |
| 2008/0020415 A1 | 1/2008 | Yadav et al. | 435/15 |
| 2009/0104674 A1 | 4/2009 | Yadav et al. | 435/134 |
| 2009/0317878 A1 | 12/2009 | Champagne et al. | 435/134 |
| 2009/0317904 A1 | 12/2009 | Vick et al. | 435/320.1 |
| 2010/0184169 A1 | 7/2010 | Roberts et al. | 435/134 |
| 2010/0192258 A1* | 7/2010 | Benning et al. | 800/281 |
| 2010/0255550 A1 | 10/2010 | Benning et al. | 435/134 |
| 2010/0255551 A1 | 10/2010 | Roberts et al. | 435/134 |
| 2010/0279390 A1 | 11/2010 | Saphire | 435/257.2 |
| 2010/0317073 A1 | 12/2010 | Sayre et al. | 435/136 |
| 2011/0061130 A1 | 3/2011 | Zou et al. | 800/281 |
| 2011/0250659 A1 | 10/2011 | Roberts et al. | 435/134 |

FOREIGN PATENT DOCUMENTS

| | | | |
|---|---|---|---|
| CN | 102492672 | 6/2012 | ............ C12N 15/54 |
| WO | WO 97/45538 | 12/1997 | ............ C12N 15/10 |
| WO | WO 00/62601 | 10/2000 | ............ A01H 13/00 |
| WO | WO 03/091413 | 11/2003 | |
| WO | WO 2005/005643 | 1/2005 | ............ C12N 15/82 |
| WO | WO 2007/133558 | 11/2007 | ............ E21B 37/00 |
| WO | WO 2009/149465 | 12/2009 | ............ C12N 15/82 |
| WO | WO 2011/026008 | 3/2011 | ............... C12P 1/00 |
| WO | WO 2011/034863 | 3/2011 | ............ A01H 13/00 |
| WO | WO 2011161093 A1 * | 6/2011 | |
| WO | WO 2011/156520 | 12/2011 | ............... C12P 7/64 |
| WO | WO 2011/161093 | 12/2011 | ............ C12N 15/82 |
| WO | WO 2011156520 | * 12/2011 | |
| WO | WO 2012/059925 | 5/2012 | ............... A01H 5/00 |
| WO | WO 2012/087982 | 6/2012 | ............... C12N 1/00 |

OTHER PUBLICATIONS

Parrish et al (articulate and dissolved lipid classes in cultures of Phaeodactylum tricornutum grown in cage culture turbidostats with a range of nitrogen supply rates. Marine Ecology. 35: 119-128, 1987).*

Friedberg (Automated protein function prediction—the genomic challenge. Brief. Bioinformatics. 7: 225-242, 2006).*

Hill et al (Functional analysis of conserved histidines in ADP-glucose pyrophosphorylase from *Escherichia coli*. Biochem. Biophys. Res. Comm. 244:573-577, 1998).*

Guo et al (Protein tolerance to random amino acid change, Proc. Natl. Acad. Sci. USA 101:9205-9210, 2004).*

Parrish et al (Particulate and dissolved lipid classes in cultures of Phaeodactylum tricornutum grown in cage culture turbidostats with a range of nitrogen supply rates. Marine Ecology. 35: 119-128, 1987).*

Office Action dated Sep. 24, 2013 issued in U.S. Appl. No. 13/707,287.

Wang, et al., UniProt. Database, Accession No. E9NME7 (Apr. 2011).

(Continued)

*Primary Examiner* — Medina A Ibrahim
*Assistant Examiner* — Wayne Zhong
(74) *Attorney, Agent, or Firm* — Harness, Dickey & Pierce P.L.C.

(57) ABSTRACT

The present invention provides diacylglycerol acyltransferase (DGAT) genes, including genes encoding localization peptides. The present invention also provides recombinant cells, such as algae, transformed with DGAT genes and methods of using such recombinant cells to produce triglyceride.

20 Claims, 12 Drawing Sheets
(7 of 12 Drawing Sheet(s) Filed in Color)

(56) References Cited

OTHER PUBLICATIONS

Office Action dated Dec. 13, 2013 issued in U.S. Appl. No. 13/707,287.
Abe, J., et al. (2008), "Expression of exogenous genes under the control of endogenous HSP70 and CAB promoters in the closterium peracerosum-strigosum-littorale complex", *Plant Cell Physiol*, 49(4): 625-632.
Altschul, S., et al. (1997), "Gapped Blast and PSI-Blast: a new generation of protein database search programs", *Nucleic Acids Research*, 25(17): 3389-3402.
Alvarez, HM, et al. (2002), "Triacylglycerols in prokaryotic microorganisms", *Appl Microbiol Biotechnol*, 60(4): 367-376.
Alvarez, A., et al. (2008), Cloning and characterization of a gene involved in triacylglycerol biosynthesis and identification of additional homologous genes in the oleaginous bacterium *Rhodococcus opacus* PD630, *Microbiology*, 154: 2327-2335.
Andrianov, V., et al., (2010), "Tobacco as a production platform for biofuel: overexpression of Arabidopsis DGAT and LEC2 genes increases accumulation and shifts the composition of lipids in green biomes", *Plant Biotechnol J.*, 8(3): 277-287.
Apt. K., et al., (2002), "In vivo characterization of diatom multipartite plastid targeting signals", *Journal of Cell Science*, 115: 4061-4069.
Arabolaza, A., et al., (2008), "Multiple pathways for triacyclglycerol biosynthesis in *Streptomyces coelicolor*", *Applied and Environmental Microbiology*, 74(9): 2573-2582.
Barney, et al., (2012), "Differences in substrate specificities of five bacterial wax ester synthases", *Appl. And Environmental Microbiology*, 78(16): 5734-5745.
Beopoulos, A., et al., (2012), "Identification and characterization of DGA2, an acyltransferase of the DGAT1 acyl-coa:diacylglycerol acyltransferase family in the oleaginous yeast *Yarrowia lipolytica*. New insights into the storage lipid metabolism of oleaginous yeasts" *Appl Microbiol Biotechnol*, 93:1523-1537.
Biester, E., et al., (2012), "Multifunctional Acyltransferases from *Tetrahymena thermophila*", *Lipids*, 47: 371-381.
Bouvier-Navé, P., et al., (2000), "Expression in yeast and tobacco of plant cDNAs encoding acyl CoA:diacylglycerol acyltransferase", *Eur. J. Biochem.*, 267, 85-96.
Buhman, K., et al., (2001), "The enzymes of neutral lipid synthesis", *Minireview*, 276(44): 40369-40372.
Cagliari, A., et al., (2011), "Biosynthesis of triacylglycerols (TAGs) in plants and algae", *International Journal of Plant Biology*, 2:e10.
Cases, S., et al. (1998), "Identification of a gene encoding an acyl coa:diacylglycerol acyltransferase,a key enzyme in triacylglycerol synthesis", *Proc. Natl. Acad. Sci. USA*, 95: 13018-13023.
Cases, S., et al. (2001), "Cloning of DGAT2, a second mammalian diacylglycerol acyltransferase, and related family members*", *The Journal of Biological Chemistry*, 276(42), 38870-38876.
Castruita, M., et al. (2011), "Systems biology approach in *Chlamydomonas* reveals connections between copper nutrition and multiple metabolic steps", *The Plant Cell*, 23: 1273-1292.
Chen, H., et al. (2008), "Conditional production of a functional fish growth hormone in the transgenic line of nannochloropsis octulata (Eustigmatophyceae)[1]", *J. Phycol.*, 44: 768-776.
Chen, W., et al., (2009), "A high throughput nile red method for quantitative measurement of neutral lipids in microalgae", *J Microbiol Methods*, 77(1): 41-47.
Chen, J., et al., (2011), "Correlation of Kennedy pathway efficiency with seed oil content of canola (*Brassica napus L.*) lines", *Can J. Plant Sci.*, 91: 251-259.
Chen, J., et al. (2012), "A look at diacylglycerol acyltransferases (DGATs) in algae", *Journal of Biotechnology*, 162: 28-39.
Courchesne, M., et al., (2009), "Enhancement of lipid production using biochemical, genetic and transcription factor engineering approaches", *Journal of Biotechnology*, 141: 31-41.
Daniel, J., et al. (2004), "Induction of a novel class of diacylglycerol acyltransferases and triacyglycerol accumulation in *Mycobacterium tuberculosis* as it goes into a dormancy-like state in culture", *Journal of Bacteriology*, 186(15): 5017-5030.
Duan, Y., et al., (2011), *De novo* Biosynthesis of biodiesel by *Escherichia coli* in optimized fed-batch cultivation, *PloS One*, 6(5): e20265.
Durrett, T., et al. (2010), "A distinct DGAT with sn-3 acetyltransferase activity that synthesizes unusual, reducted-viscosity oils in *Euonymus* and transgenic seeds", *Proc. National Acad Sci USA*, 107(20): 9464-9469.
Fan, J., et al., (2011), "Corrigendum to a cholorplast pathway for the de novo biosynthesis of triacylglycerol in *chlamydomonas reinhardtii*" [FEBS lett. 585 (2011) 1985-1991], *FEBS Letters*, 585: 4029.
Fan, J., et al., (2011), "A cholorplast pathway for the de novo biosynthesis of triacylglycerol in *chlamydomonas reinhardtii*", *FEBS letters*, 585: 1985-1991.
Ferrante, P. et al. (2008), "An optimized, chemically regulated gene expression system for *Chlamydomonas*", *PloS ONE*, 3(9): e3200.
Fischer, N., et al. (2001), "The flanking regions of PSaD drive efficient gene expression in the nucleus of the green alga chlamydomonas reinhardtii", *Mol Genet Genomics*, 265(5): 888-894.
Gouveia, L., et al. (2009), "Microalgae as a raw material for biofuels production", *J ind Microbiol Biotechnol*, 36: 269-274.
Greenspan, P., et al. (1985), "Nile red: a selective fluorescent stain for intracellular lipid droplets" *The Journal of Cell Biology*, 100: 965-973.
Greenwell., H., et al. (2010), "Placing microalgae on the biofuels priority list: a review of the technological challenges", *Journal of the Royal Society Interface*, 7: 703-726.
Hellmann, A., et al. (1997), "Gene replacement by homologous recombination in the multicellular green alga volvox carteri" *Proc. Natl. Acad. Sci USA*, 94:7469-7474.
Henikoff, S., et al. (1992), "Amino acid substitution matrices from protein blocks", *Proc. Natl. Acad. Sci USA*, 89:10915-10919.
Hernández, L., et al., (2012), "A cytosolic acyltransferase contributes to triacylglycerol synthesis in surcrose-rescued arabidopsis seed oil catabolism mutants", *Plant Physiology*, 160: 215-225.
Hernàndez, M., et al., (2012), "The atf2 gene is involved in triacylglycerol biosynthesis and accumulation in the oleaginous *Rhodococcus opacus* PD630", *Applied Microbial and Cell Physiology*, DOI 10.1007/S00253-012-4360-1.
Hu, Q., et al., (2008), "Microalgal triacylglycerols as feedstocks for biofuel production: perspectives and advances", *The Plant Journal*, 54: 621-639.
Iwai, M., et al. (2004), "Improved genetic transformation of the thermophilic cyanobacterium, thermosynechoccus elongates BP-1", *Plant Cell Physiol.* 45(2):171-175.
Jako, C., et al. (2001), "Seed-specific over-expression of an arabidopsis cDNA encoding a diacylglycerol Acyltransferase enhances seed oil content and seed weight", *Plant Physiology*, 126: 861-874.
Kaddor, C., et al (2009), "Analysis of neutral lipid biosynthesis in *Streptomyces avermitilis* MA-4680 and characterization of an acyltransferase involved herein", *Appl Microbiol Biotechnol*, 84: 143-155.
Kalscheuer, R., et al. (2003), "A novel bifunctional wax ester synthase/acyl-coa:diacylglycerol acyltransferase mediates wax ester and triacylglycerol biosynthesis in *Acinetobacter calcoaceticus* ADP1*", *The Journal of Biological Chemistry*, 278(10): 8075-8082.
Karlin, S., et al., (1990), "Methods for assessing the statistical significance of molecular sequence features by using general scoring schemes", *Proc. Natl. Acad. Sci. USA*, 87: 2264-2268.
Kindle, K., et al. (1989), "Stable nuclear transformation of chlamydomonas using the chlamydomonas gene for nitrate reductase", *The Journal of Cell Biology*, 109 (6, Part 1), 2589-2601.
La Fontaine, S., et al. (2002), "Copper-dependent iron assimilation pathway in the model photosynthetic Eukaryote *Chlamydomonas reinhardtii*", *Eukaryotic Cell*, 1(5): 736-757.
La Russa, M., et al., (2012), "Functional analysis of three type-2 DGAT homologue genes for triacylglycerol production in the green microalga *Chlamydomonas reinhardtii*", *Journal of Biotechnology*, 162(1): 13-20.

(56) References Cited

OTHER PUBLICATIONS

Lardizabal, K., et al., (2008), "Expression of *Umbelopsis ramanniana* DGAT2A in seed increases oil in soybean", *Plant Physiology*, 148: 89-96.
Lemmon, M., et al., (2008), "Membrane recognition by phospholipid-binding domains", *Nature Reviews*, 9: 99-111.
Lung, SC., et al., (2006), "Diacylglycerol acyltransferase: a key mediator of plant triacylglycerol synthesis", *Lipids*, 41(12): 1073-1088.
Mendes, A., et al., (2009), "*Crypthecondinium cohnii* with emphasis on DHA production: a review", *J. Appl Phycol.*, 21: 199-214.
Méndez-Alvarez, S., et al. (1994), "Transformation of chlorobium limicola by a plasmid that confers the ability to utilize thiosulfate" *Journal of Bacteriology*,176(23):7395-7397.
Merchant, S., et al. (2011), "TAG, you're It! Chlamydomonas as a reference organism for understanding algal triacylglycerol accumulation", *Current Opinion in Biotechnology*, 23: 1-12.
Miller, R., et al. (2010), "Changes in transcript abundance in *Chlamydomonas reinhardtii* following nitrogen deprivation predict diversion of metabolism", *Plant Physiology*, 154: 1737-1752.
Napier, JA., et al. (2010), "Tailoring plant lipid composition: designer oilseeds come of age", *Current Opinion Plant Biol.*, 13(3): 330-337.
No, D., et al. (1996), "Ecdysone-inducible gene expression in mammalian cells and transgenic mice", *Proc. Natl. Acad. Sci. USA*, 93: 3346-3351.
Oakes, J., et al. (2011), "Expression of fungal *diacylglycerol acyltransferase2* genes to increase kernel oil in maize", *Plant Physiology*, 155: 1146-1157.
Ohnuma M., et al. (2008), "Polyethylene glycol (PEG)-mediated transient gene expression in a red alga, cyanidioschyzon merolae 10D", *Plant Cell Physiol*. 49(1):117-120.
Pearson, W., et al. (1988), "Improved tools for biological sequence comparison", *Proc. Natl. Acad. Sci USA*, 85: 2444-2448.
Perrone, C., et al. (1998), "The chlamydomonas IDA7 locus encodes a 140 kDa dynein intermediate chain required to assemble the I1 inner arm complex", *Molecular biology of the Cell*, 9:3351-3365.
Philip, F., et al. (2002), "Multiple roles of Pleckstrin homology domains in phospholipase Cβ function", *FEBS Letters*, 531: 28-32.
Poulsen, N., et al. (2005), "A new molecular tool for transgenic diatoms control of mRNA and protein biosynthesis by an inducible promoter-terminator cassette", *FEBS Journal*, 272: 3413-3423.
Quinn, J., et al. (2000), "Coordinate cooper- and Oxygen-responsive Cyc6 and Cpx1 expression in *Chlamydomonas* is mediated by the same element" *The Journal of Biological Chemistry*, 275(9): 6080-6089.
Quinn, J., et al. (2003), "Copper response element and Crr1-dependent $Ni^2$—responsive promoter for induced, reversible gene expression in *Chlamydomonas reinhardtii*" *Eukaryotic Cell*, 2(5): 995-1002.
Radakovits, R., et al., (2011), "Genetic engineering of fatty acid chain length in *phaeodactylum tricornutum*" *Metabolic Engineering*, 13: 89-95.
Ramesh, V., et al. (2004), "A simple method for chloroplast transformation in chlamydomonas reinhardtii" *Methods in Molecular Biology*, 274:301-307.
Ravindran, C., et al. (2006), "Electroporation as a tool to transfer the plasmid pRL489 in Oscillatoria MKU 277" *Journal of Microbiological Methods*, 66:174-176.
Rodolfi, L., et al. (2009), "Microalgae for oil: strain selection, induction of lipid synthesis and outdoor mass cultivation in a low-cost photobioreactor", *Biotechnology & Bioengineering*, 102(1): 100-112.
Sandager, L., et al. (2002), "Storage lipid synthesis is non-essential in yeast", *The Journal of Biological Chemistry*, 277(8), 6478-6482.
Saha, S., et al. (2006), "Cytosolic triacylglycerol biosynthetic pathway in oilseeds. Molecular cloning and expression of peanut cytosolic diacylglycerol acyltransferase", *Plant Physiology*, 141: 1533-1543.
Scheffzek, K., et al. (2012), "Pleckstrin homology (PH) like domains—versatile modules in protein-protein interaction platforms", *FEBS Letters*, 586: 2662-2673.
Schroda, M., et al. (2000), "The HSP70A promoter as a tool for improved expression of transgenes in Chlamydomonas", *The plant journal* 21(2):121-131.
Scott, S., et al. (2010), "Biodiesel from algae: challenges and prospects", *Current Opinion in Biotechnology* 21: 1-10.
Siloto, RM, et al, (2009), "Simple methods to detect triacylglycerol biosynthesis in a yeast-based recombinant system", *Lipids*, 44(10): 963-973.
Siloto, RM, et al., (2009), "Directed evolution of acyl-CoA: diacylglycerol acyltransferase: development and characterization of Brassica napus DGAT1 mutagenized libraries", *Plant Physiology and Chemistry*, 47(6): 456-461.
Smith, T., et al., (1981), "Comparison of biosequences", *Advances in Applied Mathematics*, 2: 482-489.
Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.
Stemmer, W., (1994), "DNA shuffling by random fragmentation and reassembly: in vitro recombination for molecular evolution", *Proc. Natl. Acad. Sci. USA*, 91: 10747-10751.
Stone, S., et al. (2009), "The endoplasmic reticulum enzyme DGAT2 is found in mitochondria-associated membranes and has a mitochondrial targeting signal that promotes its association with mitochondria", *Journal of Biological Chemistry*, 284(8): 5352-5361.
Stöveken, T., et al (2008), "Bacterial acyltransferases as an alternative for lipase-catalyzed acylation for the production of oleochemicals and fuels", *Angew Chem Int Ed Engl.*, 47(20): 3688-3694.
Sun, Y., et al. (2006), "Functional complementation of a nitrate reductase defective mutant of a green alga dunaliella viridis by introducing the nitrate reductase gene", *Gene* 377:140-149.
Tan, C., et al. (2005), "Establishment of a micro-particle bombardment transformation system for dunaliella saline", *The Journal of Microbiology* 43:361-365.
Turchetto-Zolet, A., et al., (2011), "Evolutionary view of acyl-CoA diacylglycerol acyltransferase (DGAT), a key enzyme in neutral lipid biosynthesis", *BMC Evolutionary Biology*, 11: 263.
Wagner, M., et al. (2010), "Identification and characterization of an acyl-coa:diacylglycerol acyltransferase 2 (DGAT2) gene from the microalga *O. taurf*", *Plant Physiology and Biochemistry*, 48(6): 407-416.
Walker, T., et al. (2004), "Characterization of the *Dunaliella teritiolecta* RbcS genes and their promoter activity in *Chlamydomonas reinhardtii*", *Plant Cell Reports*, 23: 727-735.
Wältermann, M., et al. (2007), "Key enzymes for biosynthesis of neutral lipid storage compounds in prokaryotes: properties, function and occurrence of wax ester synthases/acyl-CoA: diacylglycerol acyltransferases", *Biochimie*, 89: 230-242.
Wang, P., et al. (2004), "Rapid isolation and functional analysis of promoter sequences of the nitrate reductase gene from *Chlorella ellipsoidea*", *Journal of Applied Phycology*, 16(1): 11-16.
Watt, S., et al. (2008), "urg1: A uracil-regulatable promoter system for fission yeast with short induction and repression times" *PloS one*, 1: e1428.
Weber, W., et al. (2011) "Molecular diversity—the toolbox for synthetic gene switches and networks", *Curr Opin Chem Biol.*, 15(3): 414-420.
Weselake, R., et al. (2008), "Metabolic control analysis is helpful for informed genetic manipulation of oilseed rape (*Brassica napus*) to increase seed oil content", *Journal of Experimental Botany*, 59(13): 3543-3549.
Wijffels, R., et al., (2010), "An outlook on microalgal biofuels", *Science Magazine*, 329(5993): 796-799.
Wurch, L., et al., (2011), "Nutrient-regulated transcriptional responses in the brown tide forming alga *Aureococcus anophagefferens*", *Environ Microbiol*, 13(2): 468-481.
Xut, J., et al., (2008), "Cloning and characterization of an acyl-CoA-dependent diacylglycerol acyltransferase 1 (DGAT1) gene from Tropaeolum majus, and a study of the functional motifs of the DGAT

(56) References Cited

OTHER PUBLICATIONS protein using site-directed mutagenesis to modify enzyme activity and oil content", *Plant Biotechnol J.*, 6(8): 799-818.

Yehudai-Resheff, S., et al. (2007), "Integration of chloroplast nucleic acid metabolism into the phosphate deprivation response in *Chlamydomonas reinhardtii*", *The Plant Cell*, 19: 1023-1038.

Yen, C., et al., (2005), "The Triacylglycerol synthesis enzyme DGAT1 also catalyzes the synthesis of diacylglycerols, waxes, and retinyl esters" *Journal of Lipid Research*, 46: 1501-1511.

Yen, C., et al. (2008), "DGAT enzymes and triacylglycerol biosynthesis", *Journal of Lipid Research*, 49: 2283-2301.

Yu, W., et al. (2011), "Modifications of the metabolic pathways of lipid and triacylglycerol production in microalgae", *Microbial Cell Factories*, 10(91).

Zheng, P., et al., (2008), "A phenylalanine in DGAT is a key determinant of oil content and composition in maize", *Nature Genetics*, 40: 367-372.

International Search Report and Written Opinion issued in PCT/US2012/060435 dated Feb. 27, 2013.

International Search Report and Written Opinion issued in PCT/US2012/068272 dated Mar. 25, 2013.

I0YRH1, UniProtKB submission I0YRH1_9CHLO, Oct. 31, 2012 [online]. [Retrieved on Feb. 17, 2013]. Retrieved from the Internet <URL:http://www.uniprot.org/uniprot/I0YRH1.txt?version=4>.

E1ZTZ7, UniProtKB submission E1ZTZ7_CHLVA, Oct. 31, 2012 [online]. [Retrieved on Feb. 17, 2013]. Retrieved from the Internet <URL:http://www.uniprot.org/uniprot/E1ZTZ7.txt?version=8>.

G9L2I1, UniProtKB submission G9L2I1_MUSPF, Nov. 28, 2012 [online]. [Retrieved on Feb. 17, 2013]. Retrieved from the Internet <URL:http://www.uniprot.org/uniprot/G9L2I1.txt?version=4>.

B4LX14, UniProtKB submission B4LX14_DROVI, Nov. 28, 2012 [online]. [Retrieved on Feb. 17, 2013]. Retrieved from the Internet <URL:http://www.uniprot.org/uniprot/B4LX14.txt?version=29>.

E3X631, UniProtKB submission E3X631_ANODA, Nov. 28, 2012 [online]. [Retrieved on Mar. 5, 2013]. Retrieved from the Internet <URL:http://www.uniprot.org/uniprot/E3X631.txt?version=10>.

Boyle, N.R., et al. "Three acyltransferases and nitrogen-responsive regulator are implicated in nitrogen starvation-induced triacylglycerol accumulation in *Chlamydomonas*", (2012) *The Journal of Biological Chemistry*, 287(19):15811-15825.

Guihéneuf, F., et al. "Cloning and molecular characterization of a novel acy-CoA:diacylglycerol acyltransferase 1-like gene (*PtDGAT1*) from the diatom *Phaeodactylum tricornutum*", (2011) *The FEBS Journal*, 278:3651-3666.

Jing, Y., et al. *No Title*, Submitted (Jul. 2011) to the EMBL/GenBank/DDBJ databases.

Saraste, M., et al. "Pleckstrin homology domains: a fact file", (1995) *Current Opinion in Structural Biology*, 5:403-408.

Wang, T., et al. "Fluorescence quantitative RT-PCR detection of key enzymes of Thalassiosira pseudonana neutral lipid synthesis in different growth periods", Submitted (Jan. 2011) to the EMBL/GenBank/DDBJ databases.

Xu, J., et al. "Cloning and characterization of an acyl-CoA-dependent *diacylglycerol acyltransferase 1* (*DGAT1*) gene from *Tropaeolum majus*, and a study of the functional motifs of the DGAT protein using site-directed mutagenesis to modify enzyme activity and oil content", (2008) *Plant Biotechnology Journal*, 6:799-818.

Xu, J., et al. "Triacylglycerol synthesis by PDAT1 in the absence of DGAT1 activity is dependent on re-acylation of LPC by LPCAT2", (2012) *BMC Plant Biology*, 12:4.

International Preliminary Report on Patentability dated Apr. 30, 2015 issued in PCT Patent Application No. PCT/US2012/060435.

International Preliminary Report on Patentability dated Jun. 18, 2015 issued in PCT Patent Application No. PCT/US2012/068272.

\* cited by examiner

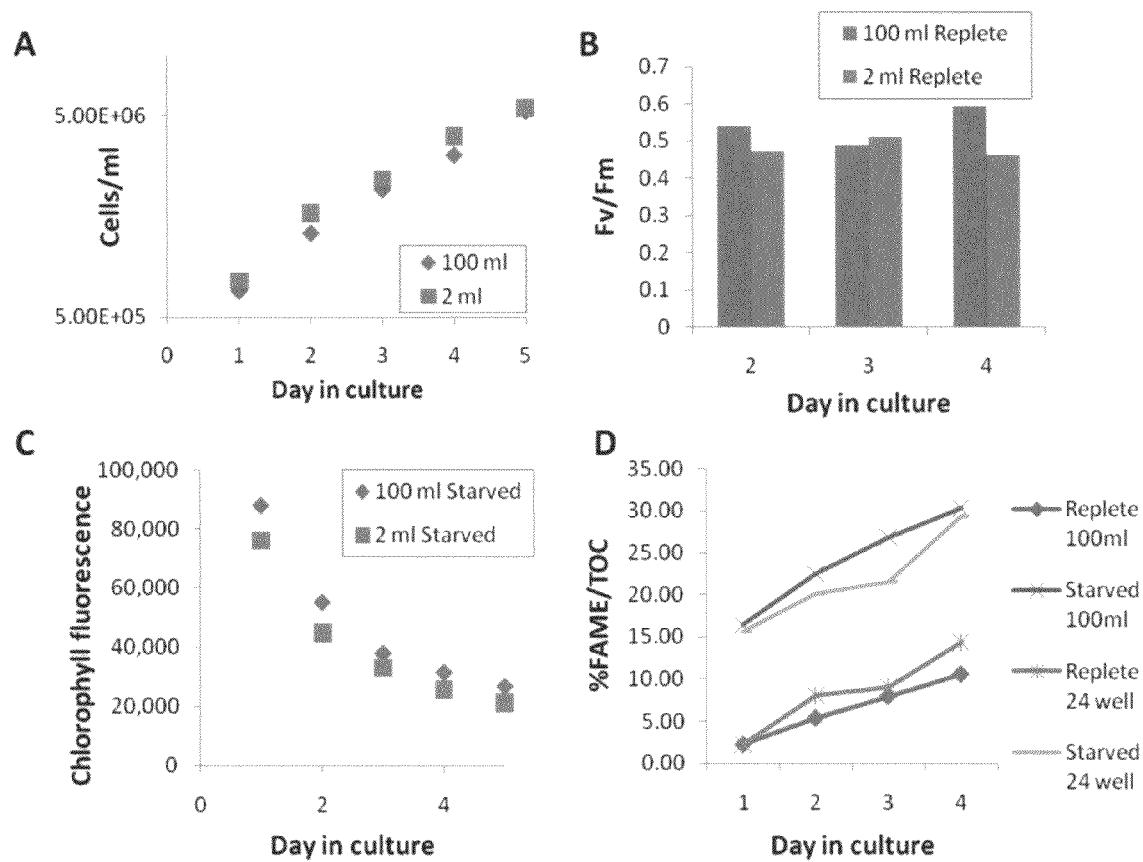
Figure 9 (A-D)

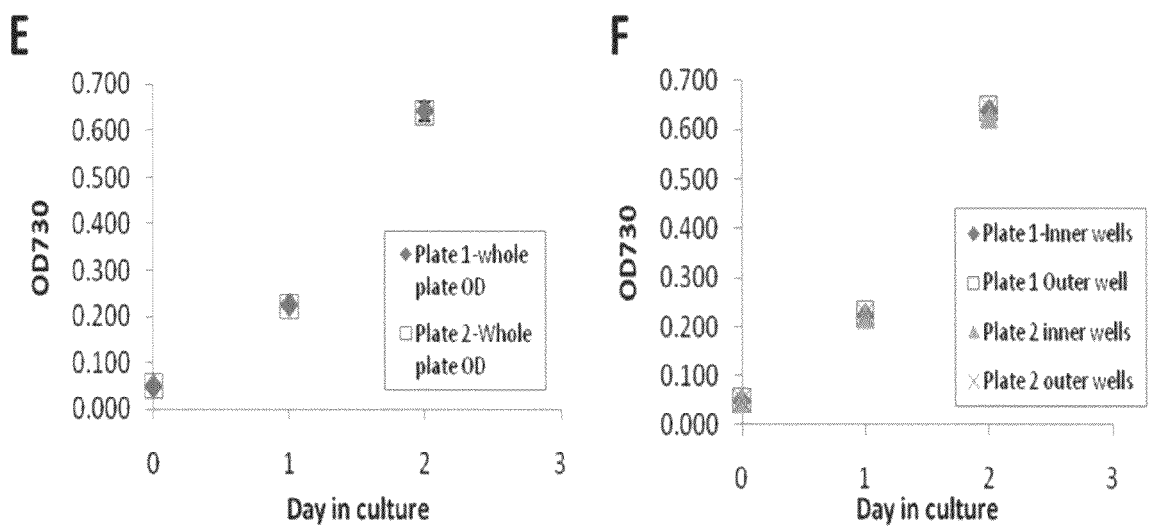
Figure 9 (E,F)

US 9,328,336 B2

DGAT GENES AND METHODS OF USE FOR TRIGLYCERIDE PRODUCTION IN RECOMBINANT MICROORGANISMS

REFERENCE TO A SEQUENCE LISTING

This application contains references to amino acid sequences and/or nucleic acid sequences which have been submitted concurrently herewith as the sequence listing text file "16244-000014-US.txt", file size 96 KiloBytes (KB), created on 14 Sep. 2012. The aforementioned sequence listing is hereby incorporated by reference in its entirety pursuant to 37 C.F.R. §1.52(e)(5).

FIELD

The present invention relates to diacylglycerol acyltransferase (DGAT) genes and the production of triglyceride (TAG) in a recombinant microorganism or host cell engineered to increase/maximize TAG synthesis and to methods of producing TAG using such recombinant microorganisms or host cells. The invention also relates to the targeting of particular proteins to the inner membrane surface of a host-cell chloroplast.

BACKGROUND

Producing renewable sources for a variety of fuels and chemicals is of great importance to a world with increasing demand for such products. While petroleum is a product of decayed plant and other matter that has been incubated beneath the earth's surface for millions of years, some efforts today focus on the direct use of plants and other organisms to generate, e.g., lipids, which can include fatty acids and derivatives thereof, for use in the fuel and chemical industries. Specifically, recent effort has been directed to designing algae to produce lipids for biofuel production because algae can proliferate over a wide range of environmental conditions and because algae do not compete with food crops for arable growth space. See, Hu et al. (2008) *Plant J.* 54, 621-39.

Algal cells are a promising source of biofuels. Wijffels & Barbosa (2010) *Science* 329, 796-99. Their ability to harness solar energy to convert carbon dioxide into carbon-rich lipids already exceeds the abilities of oil-producing agricultural crops, with the added advantage that algae grown for biofuel do not compete with crops for agricultural land (Wijffels & Barbosa, 2010). In order to maximize algal fuel production, new algal strains will need to be engineered for growth and carbon fixation at an industrial scale (Wijffels & Barbosa, 2010).

Triacylglycerol or triglyceride (TAG), a heterogeneous group of molecules with a glycerol backbone and three fatty acids attached by ester bonds, is an excellent molecule for high-concentration metabolic-energy storage. TAG the major form of energy storage in many eukaryotic algae under stress conditions, such as under nutrient limitation or depletion, where nitrogen depletion (where there is essentially no available nitrogen in the culture medium) is particularly effective in increasing TAG production in many eukaryotic algal species. However, culturing algae under nitrogen deficiency simultaneously limits overall lipid productivity of the culture by limiting overall biomass accumulation (Brennan and Owende (2010) *Renewable and Sustainable Energy Reviews* 14: 557-577). Improving the scalability, controllability, and cost-effectiveness of TAG production would be beneficial to the development of renewable energy and chemical sources.

One means of boosting TAG production is to grow algae in a two-step process alternating between nutrient-rich and nutrient-limited conditions. The nutrient-rich growth phase allows the algae to proliferate, while nutrient limitation (e.g., nitrogen depletion) results in the production of storage lipids. See, Rodolfi et al. (2009) *Biotechnol. Bioeng.* 102, 100-12. This process makes TAG production more expensive, because it requires long periods of growth during which the algae are producing little to no TAG.

Another means of boosting TAG production is to grow the algae heterotrophically by supplying extra organic carbon. For example, in various scenarios, organic carbon may be supplied as glycerol, one or more sugars, one or more organic acids, or other reduced carbon sources added to the growth medium. See, Allnutt et al. (WO 2011/026008). This heterotrophic growth technique not only increases the expense of TAG production, it also risks the contamination of the algal cultures with exogenous bacteria or fungi whose growth can be stimulated by the added carbohydrates. See, Scott et al. (2010) *Curr. Opin. Biotechnol.* 21, 277-86.

The biosynthesis pathways leading to the production of TAG have been studied. In the final reaction of the Kennedy pathway, diacylglycerol (DAG), a precursor to both membrane and storage lipids, is covalently linked to a fatty acyl to produce TAG. This reaction is catalyzed by the diacylglycerol acyltransferase (DGAT) enzyme (Kennedy (1961) *Fed. Pro. Fed. Am. Soc. Exp. Biol.* 20, 934-40). There are two distinct gene families in eukaryotic organisms which encode enzymes which catalyze this reaction, DGAT1 and DGAT2, which have little sequence similarity. Evidence from higher plants as well as mammals suggests that the two gene families have different functions, although the exact role of each type of DGAT has not been elucidated, and may differ in different species (Yen et al. (2008) *J. Lipid Res.* 49, 2283-301). A third DGAT gene family known as DGAT3 genes encode soluble DGATs, such as that of peanut (Saha et al. (2006) *Plant Physiol* 141: 1533-1543) and *Arabidopsis* (Hernandez et al. (2012) *Plant Physiol.* Published on Jul. 3, 2012, as DOI: 10.1104/pp. 112.201541). Another member of the extended DGAT family is the diacylglycerol acetyl-CoA transferase that transfers a two carbon acetyl group, rather than a longer acyl chain, to DAG (Durrett et al. (2010) *Proc. National Acad Sci USA* 107: 9464-9469). Additionally, certain prokaryotic species that are able to accumulate neutral lipids include acyltransferases for the production of wax esters or TAG that belong to the "WS/DGAT" family of DGATs (Barney et al. (2012) *Appl. And Environ Microbiol.* 78: 5734-5745).

Although overexpression of DGAT genes was found in several studies to increase TAG accumulation in higher plants, as yet attempts to increase TAG production by overexpression of DGAT genes in eukaryotic algae have been unsuccessful (Courchesne et al. (2009)).

Roberts et al. (U.S. Pub. No. 2010/0255551) and Roberts et al. (U.S. Pub. No. 2010/0184169) report the expression of DGATs derived from *Acinetobacter baylii*, *Streptomyces coelicolor*, and *Alcanivorax borkumensis* in the cyanobacteria *Synechococcus elongatus* and *Synechocystis* PCC 6803.

Benning et al. (U.S. Pub. No. 2010/0192258) disclose DGAT genes from the alga *Chlamydomonas reinhardtii* and report their expression in *Saccharomyces cerevisiæ*.

SUMMARY

The present invention provides novel DGAT genes from a variety of sources (e.g. algal, bacterial, mammalian, and plant), including novel genes encoding localization peptides. The present invention also provides recombinant cells, such as algae, transformed with DGAT genes and their use to produce TAG. Novel methods of TAG production as provided herein that result in increased amounts of TAG being produced by a culture of a recombinant microorganism with respect to the amount produced by a control microorganism can simultaneously reduce the expense and risk of contamination associated with current proposed methods of TAG production.

In one aspect, an isolated DNA molecule is provided which comprises a nucleotide sequence encoding a DGAT that comprises an amino acid sequence selected from the group consisting of an amino acid sequence having at least 80% identity to SEQ ID NO:18; an amino acid sequence having at least 80% identity to SEQ ID NO:24; an amino acid sequence having at least 80% identity to SEQ ID NO:36; an amino acid sequence having at least 80% identity to SEQ ID NO:82; an amino acid sequence having at least 80% identity to SEQ ID NO:84; an amino acid sequence having at least 80% identity to SEQ ID NO:86; and a combination thereof.

Also provided is an isolated DNA molecule which comprises a nucleotide sequence encoding a localization peptide selected from the group consisting of an amino acid sequence having at least 80% identity to SEQ ID NO:74; an amino acid sequence having at least 80% identity to SEQ ID NO:76; and a combination thereof. Additionally, an isolated DNA molecule encoding a localization peptide described herein can be operably linked to a nucleotide sequence encoding a heterologous gene, such as but not limited to an acyltransferase, such as, for example, a phospholipid: diacylglycerol acyltransferase (PDAT), a glycerolphosphate acyltransferase (GPAT), a lysophosphatidic acid acyltransferase (LPAAT), a monoacylglycerol acyltransferase (MGAT), a diacylglycerol acyltransferase (DGAT), a diacylglycerol acetyltransferase (DGAcT), or a combination thereof.

An isolated DNA molecule as provided herein can comprise a nucleotide sequence encoding an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity to any one or more of SEQ ID NOs: 18, 24, 36, 74, 76, 82, 84, and 86.

Also provided herein is an expression cassette. The expression cassette comprises a promoter and a heterologous gene as disclosed herein operably linked to the promoter. The heterologous gene can encode, for example, a DGAT having of an amino acid sequence with at least 80% identity to SEQ ID NO:18 or a functional fragment thereof; an amino acid sequence with at least 80% identity to SEQ ID NO:24 or a functional fragment thereof; an amino acid sequence with at least 80% identity to SEQ ID NO:36 or a functional fragment thereof; an amino acid sequence with at least 80% identity to SEQ ID NO:82 or a functional fragment thereof; an amino acid sequence with at least 80% identity to SEQ ID NO:84 or a functional fragment thereof; and/or an amino acid sequence with at least 80% identity to SEQ ID NO:86 or a functional fragment thereof. Alternatively or additionally, the expression cassette can comprise an isolated DNA molecule encoding a localization peptide as described herein having at least 80% identity to SEQ ID NO:74 and/or SEQ ID NO:76, which can be operably linked to a nucleotide sequence encoding an enzyme such as a PDAT, GPAT, LPAAT, MGAT, DGAT, and/or DGAcT. The expression cassette can be provided in a vector, e.g., an expression vector, which can optionally include one or more of an origin of replication, sequences mediating recombination into a host genome, and a selectable marker.

Further provided herein is a method of targeting an ectopically-expressed protein to a plastid, for example a chloroplast, using a localization peptide as described herein. For example, the method can include targeting an ectopically-expressed protein to the chloroplast envelope, for example, to the inner envelope of a chloroplast, using a localization peptide as described herein. The method comprises transfecting a chloroplast-containing cell with an expression vector comprising an expression cassette comprising a nucleic acid sequence encoding a localization peptide as described herein, for example, a localization peptide having at least 80% identity to SEQ ID NO:74 and/or at least 80% identity to SEQ ID NO:76, operably linked to a nucleic acid sequence encoding a protein for ectopic expression. In particular examples, the ectopically-expressed protein can be selected from the group consisting of a PDAT, a GPAT, an LPAAT, an MGAT, a DGAT, a DGAcT, and a combination thereof; and in a particular embodiment a DGAT comprises or is the ectopically-expressed protein.

Further provided herein is a recombinant eukaryotic alga that includes a non-native gene encoding a diacylglycerol acyltransferase (DGAT), in which the eukaryotic alga produces a greater amount of triglyceride than is produced by a eukaryotic alga substantially identical to the recombinant eukaryotic alga, but lacking a non-native gene encoding a DGAT diacylglycerol acyltransferase. Additionally or alternatively, the recombinant eukaryotic alga that includes a non-native gene encoding a DGAT can produce a greater amount of triglyceride than is produced by a substantially identical eukaryotic alga when the algae are cultured under conditions in which inorganic carbon is substantially the sole source of carbon in the culture medium. Further additionally or alternatively, the recombinant eukaryotic alga that includes a non-native gene encoding a DGAT can produce a greater amount of triglyceride than is produced by a eukaryotic alga substantially identical to the recombinant eukaryotic alga, when the algae are cultured under nitrogen replete conditions. A non-native gene encoding a DGAT can encode any DGAT, for example, a eukaryotic DGAT, which can be a DGAT1, DGAT2, DGAT3, DGAcT, a prokaryotic DGAT or wax synthase (WS) that has DGAT activity (e.g., a prokaryotic WS/DGAT), or a combination thereof. The non-native gene can encode a DGAT that is a variant of a naturally-occurring DGAT, such as a DGAT having at least 80%, at least 85%, at least 90%, or at least 95% amino acid sequence identity to a naturally-occurring DGAT or an active fragment thereof. The non-native gene can additionally or alternatively encode a DGAT that is a truncated variant of a naturally-occurring DGAT, such as an N-terminally or C-terminally truncated variant of a naturally-occurring DGAT or a DGAT having at least 80%, at least 85%, at least 90%, or at least 95% amino acid sequence identity to a naturally-occurring DGAT. Further additionally or alternatively, a recombinant eukaryotic alga can include a non-native gene encoding a DGAT that has at least 80%, at least 85%, at least 90%, or at least 95% amino acid sequence identity to a naturally-occurring DGAT or an active fragment thereof and can further include one or more additional amino acid sequences, such as, but not limited to, one or more amino acid sequences that can direct the DGAT to a location within the cell, such as, for example, a chloroplast or a region thereof, and/or the endoplasmic reticulum or a region thereof.

For example, a recombinant eukartyotic alga as provided herein can include a non-native gene encoding a type-1, type-2, or type-3 DGAT from a eukaryote, such as, for example, a fungus, yeast, protozoan, animal, alga, or plant, or a variant thereof having at least 80%, at least 85%, at least 90%, or at least 95% amino acid sequence identity to the naturally-occurring DGAT1, DGAT2, DGAT3, or an active fragment thereof, and which can include a deletion, for example, a truncation, with respect to the naturally-occurring DGAT amino acid sequence, and/or can include one or more additional sequences, such as, but not limited to, a cellular localization sequence. In some examples, the DGAT1, DGAT2, or DGAT3 encoded by the non-native gene comprises a sequence at least 80%, at least 85%, at least 90%, or at least 95% identical to SEQ ID NO:2, SEQ ID NO:4, SEQ ID NO:18, SEQ ID NO:24, SEQ ID NO:36, SEQ ID NO:78, SEQ ID NO:80, SEQ ID NO:82, SEQ ID NO:84, SEQ ID NO:86, and/or an active portion thereof. Alternatively or in addition, a recombinant eukartyotic alga as provided herein can include a non-native gene encoding a wax synthase/diacylglycerol transferase (WS/DGAT) from a prokaryote or a variant thereof having at least 80%, at least 85%, at least 90%, or at least 95% amino acid sequence identity to the naturally-occurring prokaryotic WS/DGAT or an active fragment thereof, and which can include a deletion, for example, a truncation, with respect to the naturally-occurring DGAT amino acid sequence, and/or can include one or more additional sequences, such as, but not limited to, a cellular localization sequence. In some examples, the prokaryotic WS/DGAT encoded by the non-native gene comprises a sequence at least 80%, at least 85%, at least 90%, or at least 95% identical to SEQ ID NO:40, SEQ ID NO:46, SEQ ID NO:50, SEQ ID NO:56, and/or an active portion thereof.

In a further aspect, a recombinant microorganism or host cell, such as a recombinant algal cell, comprising a non-native gene encoding a DGAT, wherein the DGAT comprises an amino acid sequence having at least 80% identity to SEQ ID NO:4, SEQ ID NO:18, SEQ ID NO:24, SEQ ID NO:36, SEQ ID NO:40, SEQ ID NO:46, SEQ ID NO:50, SEQ ID NO:56, SEQ ID NO:82, SEQ ID NO:84, SEQ ID NO:86, and/or to an active fragment of any thereof. For example, the non-native gene can encode a DGAT having an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NO: 4, 18, 24, 36, 46, 56, 82, 84, and 86. In some examples, the DGAT comprises or is a type 2 DGAT (DGAT2). The recombinant microorganism that includes a non-native gene encoding a DGAT can produce a greater amount of at least one lipid than a substantially identical microorganism lacking the non-native DGAT gene. For example, the recombinant microorganism that includes a non-native gene encoding a DGAT can produce a greater amount of TAG in a twenty-four hour, three day, and/or seven day time period than a substantially identical microorganism lacking the non-native DGAT gene and/or lacking the amino acid sequence that can direct the DGAT to a location within the cell. Further, the recombinant microorganism that includes a non-native gene encoding a DGAT can be a eukaryotic microalga, and preferably can produce a greater amount of lipid than a substantially identical microorganism lacking the non-native DGAT gene and/or lacking the amino acid sequence that can direct the DGAT to a location within the cell under photoautotrophic culture conditions. Additionally or alternatively, the recombinant eukaryotic microalga can produce a greater amount of lipid than a substantially identical microorganism lacking the non-native DGAT gene and/or lacking the amino acid sequence that can direct the DGAT to a location within the cell under nutrient replete culture conditions, or when cultured under nitrogen-replete conditions. Preferably, the recombinant eukaryotic microalga can produce a greater amount of lipid than a substantially identical microorganism lacking the non-native DGAT gene and/or lacking the amino acid sequence that can direct the DGAT to a location within the cell under photoautotrophic nutrient replete culture conditions and/or under photoautotrophic nitrogen replete culture conditions.

A recombinant eukaryotic algal cell as described herein can be any eukaryotic microalga, and in some examples is of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*. For example, the algal cell can be a *Nannochloropsis* cell.

Also provided is a method for producing TAG in a recombinant eukaryotic algal cell. The method comprises culturing a recombinant eukaryotic algal cell as described herein that comprises a non-native gene encoding a DGAT under culture conditions such that DGAT encoded by the non-native gene is expressed to produce TAG. In some examples, the culture conditions can be nitrogen replete. Additionally or alternatively, the culture conditions can be nutrient replete. Further additionally or alternatively, the culture conditions can be substantially or entirely photoautotrophic. Still further additionally or alternatively, the recombinant algal cells described herein can produce a greater amount of TAG under nitrogen replete conditions than is produced by a control algal cell substantially identical to the recombinant algal cell in all respects and cultured under the substantially same conditions, except that the control algal cell does not include a non-native gene encoding a DGAT and/or does not include an amino acid sequence that can direct the DGAT to a location within the cell. In some examples, the recombinant eukaryotic algal cell can be proliferating and generating TAG at levels higher than the TAG levels generated by a non-transfected control eukaryotic algal cell cultured under substantially the same conditions. For example, the recombinant eukaryotic algal cell can generate at least 50% more lipid in comparison to a non-transfected control cell or at least two fold, at least five fold, and/or at least ten fold the amount of TAG produced by a non-transfected control cell in a twenty-four hour period, a three day period, and/or a seven day period. The DGAT expressed can be encoded by any DGAT gene, and can be configured in an expression cassette optionally containing a nucleic acid sequence encoding a localization sequence as described herein (e.g. SEQ ID NOs:74 and/or 76, and/or sequences having at least 80% identity thereto). In certain examples, the DGAT expressed can have an amino acid sequence having at least 80% identity to SEQ ID NO:4, SEQ ID NO:18, SEQ ID NO:24, SEQ ID NO:36, SEQ ID NO:40, SEQ ID NO:46, SEQ ID NO:50, SEQ ID NO:56, SEQ ID NO:82, SEQ ID NO:84, and/or SEQ ID NO:86. For example, an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NOs: 4, 18, 24, 36, 46, 50, 56, 82, 84, and 86. In some examples, the DGAT can comprise or be a type 2 DGAT or a type 3 DGAT.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 is a graphical representation of the results of experiments comparing 2 mL and 100 mL cultures of *Nannochloropsis gaditana* cells grown in PM023 nutrient replete ("replete") or PM027 nitrogen-deficient ("starved") medium over four days. The cell density (FIG. 9A), photosynthetic efficiency (FIG. 9B), mean chlorophyll fluorescence (FIG. 9C), and lipid content (FIG. 9D) for 2 mL and 100 mL cultures is plotted versus days in culture. The optical density $OD_{730}$ was measured for each 2 mL culture in a 24 well plate, averaged and compared to a second plate to determine inter-well variability (FIG. 9E) and intra-well variability (FIG. 9F).

DETAILED DESCRIPTION

Definitions

Figure 1:
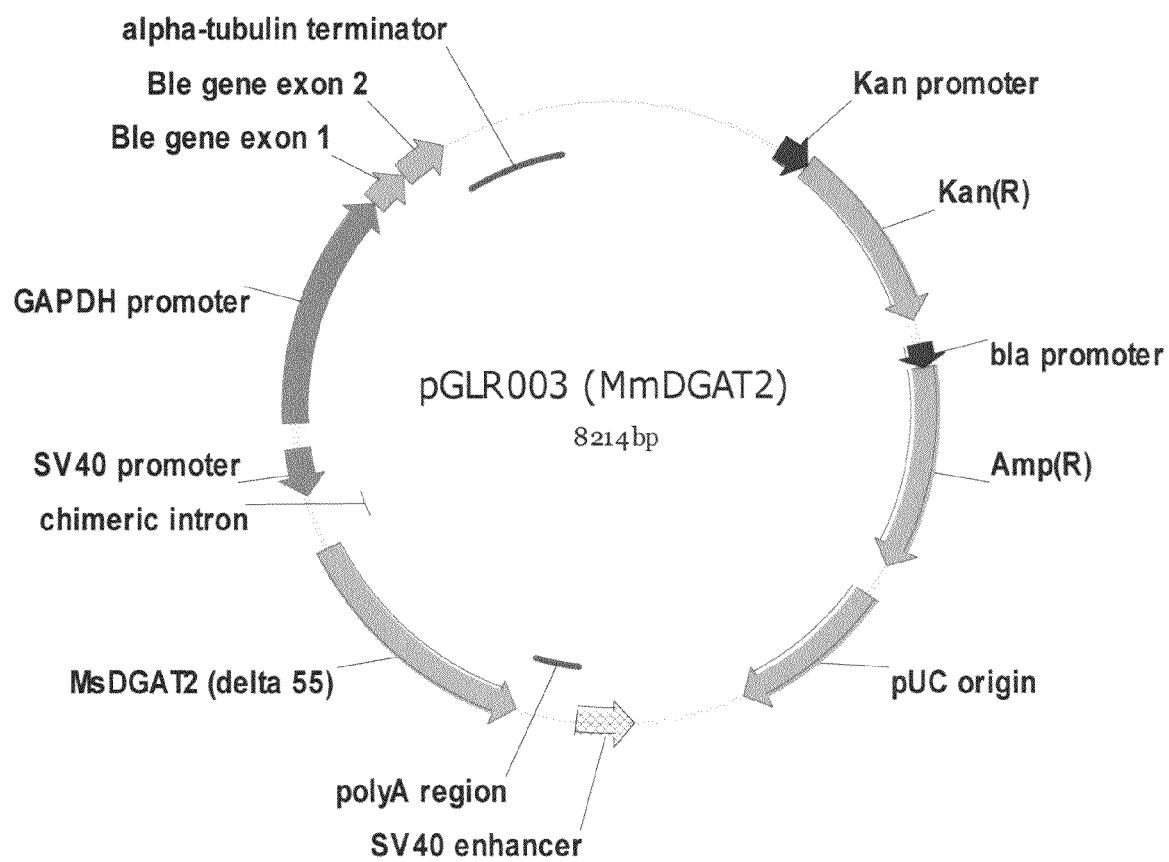
FIG. 1 is a plasmid map of the expression vector pGLR003, a vector containing a ble selectable marker and MmDGAT2Δ55 (SEQ ID NO:3) under control of SV40 promoter/terminator.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences). Genes may further comprise the regulatory sequences required for their expression. Genes can be obtained from a variety of sources, including cloning from a source of interest or synthesizing from known or predicted sequence information, and may include sequences designed to have desired parameters.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

A nucleic acid molecule may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, or insertional mutation) or having decreased expression due to alteration of gene regulatory sequences.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The term "heterologous" gene or nucleic acid sequence as used herein, refers to a gene or sequence from a different species than the species of the host organism it is introduced into. When referring to a gene regulatory sequence (such as, for example, a promoter) or protein localization sequence, "heterologous" means the regulatory sequence or localization sequence is from a different source than the nucleic acid sequence (e.g., protein coding sequence) or protein region with which it is juxtaposed in a nucleic acid construct or engineered protein.

The term, "expression cassette" as used herein, refers to a nucleic acid construct that encodes a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

The term "transgene" as used herein, refers to an exogenous gene, or a gene under the control of a promoter not normally known to control the transcription of said gene in nature.

The term "ortholog" of a gene or protein as used herein, refers to its functional equivalent in another species.

The term "operably linked," as used herein, denotes a configuration in which a control sequence is placed at an appropriate position relative to the coding sequence of a polynucleotide sequence such that the control sequence directs the expression of the coding sequence of a polypeptide and/or functional RNA). Thus, a promoter is in operable linkage with a nucleic acid sequence if it can mediate transcription of the nucleic acid sequence. When introduced into a host cell, an expression cassette can result in transcription and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense, or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "photosynthetic organism," as used herein, is any prokaryotic or eukaryotic organism that can perform photosynthesis. Photosynthetic organisms include higher plants (i.e., vascular plants), bryophytes, algae, and photosynthetic bacteria. The term "algae" includes, but is not limited to, a species of Bacillariophyceae (diatoms), Bolidomonas, Chlorophyceae (green algae), Chrysophyceae (golden algae), Cyanophyceae (cyanobacteria), Eustigmatophyceae (picoplankton), Glaucocystophytes, Pelagophytes, Phaeophyceae (brown algae), Prasinophyceae (pico-plankton), Raphidophytes, Rhodophyceae (red algae), Synurophyceae and Xanthophyceae (yellow-green algae). The term "algae" includes microalgae. The term "microalgae" as used herein refers to microscopic, single-celled algae species including, but not limited to, eukaryotic single-celled algae of the Bacillariophyceae, Chlorophyceae, and Eustigmatophyceae classes. The term "photosynthetic bacteria" includes, but is not limited to, cyanobacteria, green sulfur bacteria, purple sulfur bacteria, purple non-sulfur bacteria, and green non-sulfur bacteria.

The terms "selectable marker", "selectable marker gene," or "reporter gene," as used herein, include any gene that confers a phenotype on a cell in which it is expressed to facilitate the identification and/or selection of cells that are transfected or transformed with a nucleic acid construct of the invention. The term also includes gene products that effectuate said phenotypes. Examples of selectable markers include antibiotic resistance factors such as amikacin (aphA6), ampicillin (amp$^R$), atrazine (psbA), blasticidin (bls, bsr, bsd), bleomicin or phleomycin (ZEOCIN™) (ble), chloramphenicol (cat), dichlorophenyl dimethyl urea (DCMU) (psbA), G418 (GENETICIN™) (neo), gentamycin (aac3 or aacC4), hygromycin B (aphIV, hph, hpt), kanamycin (nptII), methotrexate (DHFR mtx$^R$), penicillin and other β-lactams (β-lactamases), streptomycin or spectinomycin (aadA, spec/strep), and tetracycline (tetA, tetM, tetQ); herbicides, such as aminotriazole, amitrole, aryloxyphenoxy propionates, bipyridyliums, bromoxynil, cyclohexandione oximes dalapon, dicamba, difunone, diketonitriles, fluridone, glufosinate, glyphosate, halogenated hydrobenzonitriles, 4-hydroxypyridines, imidazolinones, isoxasflutole, isoxazoles, isoxazolidinones, p-nitrodiphenylethers, norflurazon, oxadiazoles, m-phenoxybenzamides, N-phenyl imides, protoporphyrionogen oxidase inhibitors, pyridazinones, pyrazolinates, sulfonylureas, 1,2,4-triazol pyrimidine, triketones, urea; herbicide resistance factors such as acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, superoxide dismutase (sod); metabolic factors such as arg7, his3, hisD, hisG, manA, nit1, trpB, xylA, a dihydrofolate reductase gene, a mannose-6-phosphate isomerase gene, a nitrate reductase gene, or an ornithine decarboxylase gene; a gene that confers toxicity to insects such as the Bt cry genes; a negative selection factor such as thymidine kinase; or toxin resistance factors such as a 2-deoxyglucose resistance gene.

A reporter gene can encode a visual marker or enzyme that produces a detectable signal, such as cat, lacZ, uidA, xylE, an alkaline phosphatase gene, an α-amylase gene, an α-galactosidase gene, a β-lactamase gene, a horseradish peroxidase gene, a luciferin/luciferase gene, an R-locus gene, a tyrosinase gene, or a gene encoding the cyan, green, enhanced green, red, or yellow fluorescent proteins or any of their variants, including codon-optimized, rapidly folding, increased stability and enhanced fluorescence variants.

A "recombinant" or "engineered" nucleic acid molecule is a nucleic acid molecule that has been altered through human manipulation. As non-limiting examples, a recombinant nucleic acid molecule that: 1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. The heterologous or recombinant nucleic acid molecule can be integrated into the recombinant/genetically engineered organism's genome or in other instances are not integrated into the recombinant/genetically engineered organism's genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in both directions off of opposite strands). A promoter may be a constitutive promoter, a repressible promoter, or an inducible promoter. Non-limiting examples of promoters include, for example, the T7 promoter, the cytomegalovirus (CMV) promoter, the SV40 promoter, and the RSV promoter. Examples of inducible promoters include the lac promoter, the pBAD (araA) promoter, the Tet promoter (U.S. Pat. Nos. 5,464,758 and 5,814,618), and the Ecdysone promoter (No et al. (1996) Proc. Natl. Acad. Sci. 93, 3346-51).

The term "heterologous" when used in reference to a polynucleotide, a gene, a nucleic acid, a polypeptide, or an enzyme refers to a polynucleotide, gene, a nucleic acid, polypeptide, or an enzyme not derived from the host species. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked. Similarly, when referring to a protein localization sequence of an engineered protein, "heterologous" means that the localization sequence is derived from a protein different from that into which it is incorporated by genetic engineering.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-402 and Karlin (1990), Proc. Natl. Acad. Sci. USA 87, 2264-68), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-29. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-19), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; and/or variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

The term "secreted" includes movement of polypeptides or fatty acid products produced by the recombinant microorganisms or methods of the invention to the periplasmic space or extracellular milieu. "Increased secretion" includes secretion in excess of the naturally-occurring amount of secretion, e.g., that is at least 1%, at least 2%, at least 3%, at least 4%, at least 5%, at least 6%, at least 7%, at least 8%, at least 9%, or at least 10%, or at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, or more, as compared to the naturally-occurring level of secretion.

Some embodiments of the present invention provide for the "insertion," e.g., the addition, integration, incorporation, or introduction, the activation, or up-regulation of certain nucleic acid molecules or particular polynucleotide sequences, with or without additional regulatory sequences, within microorganisms or host cells in order to affect the activity, such as the expression of an enzyme, of certain nucleic acid molecules or particular polynucleotide sequences. In certain embodiments, a microorganism of interest may be engineered by site directed homologous recombination to insert a particular gene of interest or a promoter that affects the expression of a particular gene or set of genes.

In additional embodiments of the present invention recombinant microorganisms in which the nucleic acid molecules or particular polynucleotide sequences are partially, substantially, or completely deleted, silenced, inactivated, or down-regulated in order to affect the activity for which they encode, such as the expression of an enzyme, are provided. Genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, the generic category of enzymes known as "diacylglycerol acyltransferase" (abbreviated as "DGAT") includes the specific category of enzymes known as "diacylglycerol acetyltransferase" (abbreviated as "DGAcT").

Nucleic Acid Molecules

The nucleic acid molecules and encoded polypeptides described herein can be used in any of the methods of the invention, and may be included in any of the expression cassettes, vectors, or recombinant microorganisms of the invention. Nucleic acid molecules comprising sequences that encode DGATs are provided for use in host microorganisms and methods for producing TAG. A nucleic acid molecule as disclosed herein can be isolated and/or purified.

Diacylglycerol acyltransferases (DGATs) are members of the O-acyltransferase superfamily, which esterify either sterols or diacylglycerols in an oleoyl-CoA-dependent manner. The DGAT enzyme performs the final step in TAG biosynthesis by transferring an acyl group from acyl-coenzyme-A to the sn-3 position of 1,2-diacylglycerol (DAG) to form TAG. Eukaryotes have two types of DGAT, abbreviated as DGAT1 and DGAT2, that belong to different gene families and share little homology. Eukaryotic DGAT1 polypeptides typically contain a FYxDWWN (SEQ ID NO:87) amino acid sequence motif, as well as a histidine (or tyrosine)-serine-phenylalanine (H/YSF) tripeptide motif, as described in Guo et al. (2001) *J. Lipid Res.* 42:1282-91. DGAT2 polypeptides typically include a HPHG, EPHSV, or, as found in SEQ ID NO:36, provided herein, PPHGV. A third type of DGAT, known as DGAT3, has been identified in peanut (Saha et al. (2006) *Plant Physiol.* 141: 1533-1543) and *Arabidopsis* (Hernandez et al. (2012) *Plant Physiol.* Published on Jul. 3, 2012, as DOI:10.1104/pp. 112.201541). Further considered as a DGAT useful for expression in microoranisms as disclosed herein is a diacylglycerol acetyltransferase (DGAcT) as has been described in *Eonymous* (Durrett et al. (2010) *Proc Natl Acad Sci USA* 107: 9464-9469).

In contrast, some prokaryotes that accumulate neutral lipids have genes encoding acyltransferase enzymes that form wax esters or TAG known as "WS/DGATs" (e.g., *Acinetobacter baylii, A. baumanii,* and *M. avium,* and *M. tuberculosis* CDC1551, (see, e.g., Daniel et al., *J. Bacteriol.* 186:5017-5030, 2004; and Kalscheuer et al. (2003) *J. Biol. Chem.* 287:8075-8082).

For example, the isolated nucleic acid molecule as provided herein can encode a polypeptide having DGAT activity, in which the polypeptide comprises an amino acid sequence having:
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:2;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:4;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:18;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:24;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:36;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:40;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:46;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:50;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:56;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:78;
  at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:80;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:82;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:84;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:86;

and/or to a functional fragment of any of the provided amino acid sequences.

Assays for determining the activity of DGATs are known in the art and include, in addition to in vivo expression to evaluate increased production of TAG (e.g., the Examples provided herein that detect TAG production by gas chromatography, HPLC, or Nile Red flourescence detection), or in vivo or in vitro assays that measure TAG production using radiolabeled substrates or detection of TAG by staining of thin layer chromatograms (see, for example, Cases et al. (1998) *Proc Natl Acad Sci USA* 95: 13018-13023; Cases et al. (2001) *J. Biol. Chem.* 276: 38870-38876; Durrett et al. (2010) *Proc Natl Acad Sci USA* 107: 9464-9469; Beopoulos et al. (2012) *Appl Microbiol. Biotechnol.* 93: 1523-1537).

An isolated or recombinant nucleic acid molecule encoding a DGAT can comprise a nucleic acid sequence that encodes a polypeptide having DGAT activity that has at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a prokaryotic DGAT (e.g., a WS/DGAT), such as but not limited to *Mycobacterium smegmatis* DGAT (Genbank accession ABK74273, gene identifier 118173377; SEQ ID NO:50) and orthologs thereof in other prokaryotic species, or the bacterial DGAT of *Alcanivorax borkumensis* (Genbank accession YP_694462, gene identifier 110835603; SEQ ID NO:40) and orthologs in other bacterial species, the bacterial DGAT (SEQ ID NO:46) that is highly homologous to the *Marinobacter hydrocarbonoclasticus* WS/DGAT (Genbank accession ABM17275, gene identifier 120322960) and orthologs in other bacterial species, and/or the bacterial DGAT of *Rhodococcus opacus* (Genbank accession GQ923886, gene identifier 261411835; SEQ ID NO:56) and orthologs in other bacterial species. For example, in some instances an isolated or recombinant nucleic acid molecule encoding a DGAT can comprise a nucleic acid sequence that encodes a polypeptide having DGAT activity that has at least 85%, at least 90%, at least 95%, or at least 99% sequence identity to the amino acid sequence of a prokaryotic DGAT, such as but not limited to *Mycobacterium smegmatis* DGAT (Genbank accession ABK74273, gene identifier 118173377; SEQ ID NO:50) and orthologs thereof in other prokaryotic species, or the bacterial DGAT of *Alcanivorax borkumensis* (Genbank accession YP_694462, gene identifier 110835603; SEQ ID NO:40) and orthologs in other bacterial species, a bacterial *Marinobacter* DGAT (e.g. SEQ ID NO:46) and orthologs in other bacterial species, and/or the bacterial DGAT of *Rhodococcus opacus* (Genbank accession GQ923886, gene identifier 261411835; SEQ ID NO:56) and orthologs in other bacterial species.

Further, isolated or recombinant nucleic acid molecule encoding a DGAT can comprise a nucleic acid sequence that encodes a polypeptide having DGAT activity that has at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a eukaryotic DGAT (e.g., a DGAT1, DGAT2, DGAT3, or DGAcT), such as but not limited to a DGAT2 of *Mus musculus* (Genbank accession NP_080660, gene identifier 16975490; SEQ ID NO:2), a DGAT2 of *Nannochloropsis gaditana* (SEQ ID NOs:18, 24, and 36), a DGAT3 of *Arachis hypogaea* (Genbank accession AY875644, gene identifier 62084564; SEQ ID NO:80), a DGAcT of *Euonymus alatus* (Genbank accession GU594061, gene identifier 294992377; SEQ ID NO:78), and/or to a functional fragment thereof.

Additional DGAT1 genes that may find use in the microorganisms and methods of the invention can include those encoding DGAT1 enzymes of animals, higher plants, algae, or fungii, such as, for example, those encoding DGAT1 enzymes of *Homo sapiens* (NP_036211.2; GI:145864459); *Danio rerio* (NP_956024.1; GI:41054343); *Arabidopsis thaliana* (Accession Q9SLD2; GI:75206653); *Brassica juncea* (AAY40784.1; GI:63376226); *Zea mays* (ABV91586.1; GI:157885767); *Yarrowia lipolytica* (XP504700); and *Paracoccidiodioides brasiliensis* (EEH17170.1 GI:225678886). Also included are DGAT1 genes encoding DGAT1 enzymes having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to these enzymes, orthologs in other species, and/or active fragments thereof.

Further nonlimiting examples of DGAT2 genes include those encoding DGAT2 enzymes from, without limitation animals, higher plants, algae, or fungii, such as, for example, those encoding DGAT2 enzymes of *Arabidopsis thaliana* (Q9ASU1.1; GI:75167729); *Brassica napus* (AAD40881.1; GI:5225382); *Ostreococcus tauri* (Wagner et al. (2010) *Plant Physiol and Biochem.* 48: 407-416); *Chlamydomonas* (La Russa et al. (2012) *J. Biotechnol.* "Functional analysis of three type-2 DGAT homologue genes for triacylglycerol production in the green microalga *Chlamydomonas reinhardtii*" dx.doi.org/10.1016/j.jbiotec 0.2012.04.006, available online 19 Apr. 2012). Also included are DGAT2 genes encoding DGAT2 enzymes having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to these enzymes, their orthologs in other species, and/or active fragments thereof.

Additional examples of DGAT3 genes include those encoding DGAT3 enzymes of *Arabidopsis* and *Rhodotorula glutinis* (ABC41546.1; GI:83702260), and *Ricinus communis* (XP_002519339.1; GI:255556610). Also included are DGAT3 genes encoding DGAT3 enzymes having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to these enzymes, and/or active fragments thereof.

Additionally or alternatively, the invention encompasses nucleic acid molecules encoding truncations of a DGAT where one or more amino acids have been deleted from the protein. For example, the encoded polypeptide can lack at least 1, at least 2, at least 3, at least 4, at least 5, at least 6, at least 7, at least 8, at least 9, at least 10, at least 20, at least 30, at least 40, at least 50, at least 60, at least 70, or at least 80 amino acids from the N- and/or C-terminus and can have an amino acid sequence at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or about 100% identical to the corresponding amino acid sequence of SEQ ID NOs: 2, 4, 18, 24, 36, 40, 46, 50, 56, 78, 80, 82, and/or 84. In some examples, the deleted sequences may include targeting sequences, for example, at least a portion of a chloroplast transit peptide, at least a portion of a mitochondrial targeting sequence, at least a portion of an endoplasmic reticulum targeting sequence, etc. By way of nonlimiting example, in some instances an isolated or recombinant nucleic acid molecule encoding a DGAT can comprise a nucleic acid sequence that encodes a polypeptide having DGAT activity that has at least 85%, at least 90%, at least 95%, or at least 99% sequence identity to the amino acid sequence of a truncated *Mus musculus* DGAT that lacks a domain to target the enzyme to the mitochondria or endoplasmic reticulum (SEQ ID NO:4).

Further, the invention provides nucleic acid molecules encoding polypeptides to target proteins (i.e. localization peptides) to the inner envelope membrane of chloroplasts. Such isolated nucleic acid molecule as provided herein can encode a localization polypeptide, in which the polpeptide comprises an amino acid sequence having:

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:74;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:76;

and/or to a functional fragment of any of the provided amino acid sequences.

For example, the nucleic acid molecules encoding localization peptides can comprise a nucleic acid sequence that encodes a polypeptide that has at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of the amino-terminus of a putative chloroplast inner envelope glucose-6-phosphate/phosphate antiporter or to one or more of the transmembrane domains thereof (e.g., SEQ ID NOs:74 and 76). The localization sequence can optionally be derived from a gene, such as a chloroplast envelope transporter gene, or a eukaryotic algal species. Additionally, the nucleic acid molecules encoding these transport peptides can be fused in frame to a nucleic acid molecule encoding an acyltransferase, such as, for example, a DGAT, a DGAcT, a glycerolphosphate acyltransferase (GPAT), a lysophosphatidic acid acyltransferase (LPAAT), and/or a monoacylglycerol acyltransferase (MGAT). The chloroplast targeting sequence can in some examples direct the protein that it is incorporated into to an inner envelope membrane of a chloroplast. For example, a nucleic acid molecule encoding a DGAT of *Euonymus alatus* can be fused to a nucleic acid molecule encoding one transmembrane domain (e.g., SEQ ID NO:82 and/or peptide sequences having at least 80% identity thereto) or two transmembrane domains (e.g., SEQ ID NO:84 and/or peptide sequences having at least 80% identity thereto) of a putative chloroplast inner envelope glucose-6-phosphate/phosphate antiporter.

Alternatively or in addition, a nucleic acid molecule that includes a sequence encoding an acyltransferase (e.g., a DGAT, DGAcT, GPAT, LPAAT, or MGAT) can further include a fused, in-frame nucleotide sequence that encodes a targeting peptide that directs a protein (such as, for example, an acyltransferase) to the endoplasmic reticulum. The peptide sequence for targeting a protein to the endoplasmic reticulum may optionally be a sequence derived from an algal protein (e.g., an algal BiP protein). For example, a nucleotide sequence encoding a DGAT can be operably linked to a nucleotide sequence encoding an ER targeting peptide having at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:30 or to another ER targeting sequence, such as an ER targeting sequence from a eukaryotic gene or algal gene, for example an ER targeting sequence from a BiP protein of any organism, such as but not limited to an alga. In nonlimiting examples, a nucleotide sequence encoding a DGAT, such as any disclosed herein, can be operably linked to a nucleotide sequence encoding an ER targeting peptide, such as SEQ ID NO:30 or an ER targeting peptide having at least 40% identity thereto. In an illustrative example, a nucleic acid molecule encoding a DGAT of *M. Musculus* can be fused to a nucleic acid molecule encoding an ER targeting domain (SEQ ID NO:86).

Additionally or alternatively, any of nucleic acid molecules encoding localization peptides can be operably linked a nucleotide sequence encoding a glycerolphosphate acyltransferase (GPAT), a lysophosphatidic acid acyltransferase (LPAAT), a monoacylglycerol acyltransferase (MGAT), a diacylglycerol acyltransferase (DGAT), and/or a diacylglycerol acetyltransferase (DGAcT).

The invention provides DGAT genes encoding fragments and variants of naturally-occurring DGATs. A substitution, insertion or deletion can adversely affect the protein when the altered sequence substantially inhibits a biological function associated with the protein. In certain embodiments, a variant of a DGAT may have activity that is reduced by not more than about 1%, not more than about 2%, not more than about 3%, not more than about 4%, not more than about 5%, not more than about 6%, not more than about 7%, not more than about 8%, not more than about 9%, not more than about 10%, not more than about 15%, not more than about 20%, not more than about 30%, not more than about 40%, or not more than about 50%, in comparison to the activity of the DGAT from which the variant is derived (e.g., any of SEQ ID NOs: 2, 4, 18, 24, 36, 40, 46, 50, 56, 78, 80, 82, and/or 84). In some embodiments, the amount of a TAG produced by a host cell expressing the DGAT variant is not less than about 99%, not less than about 98%, not less than about 97%, not less than about 96%, not less than about 95%, not less than about 94%, not less than about 93%, not less than about 92%, not less than about 91%, not less than about 90%, not less than about 85%, not less than about 80%, or not less than about 75% of the amount or the fatty acid product produced by a host cell expressing the DGAT from which the variant is derived (e.g., any of SEQ ID NOs: 2, 4, 18, 24, 36, 40, 46, 50, 56, 78, 80, 82, 84, and/or 86).

The invention also provides fragments and variants of a DGAT that have increased activity in comparison to the reference polypeptides. In certain embodiments, the DGAT fragment or variant may have activity that is increased by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000% in comparison to the activity of the DGAT from which the variant is derived. In certain embodiments, the amount of TAG produced by a host cell expressing the fragment or variant is at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000% of the amount of TAG made by a host cell expressing the DGAT from which the fragment or variant is derived.

The invention described herein also relates to fragments of the isolated nucleic acid molecules described herein encompassing a portion of a nucleotide sequence described herein which is from at least 20 contiguous nucleotides to at least 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g. nucleic acid molecules which specifically hybridize to a nucleotide sequence encoding polypeptides described herein and encode a DGAT). Hybridization probes include synthetic oligonucleotides which bind in a base-specific manner to a complementary strand of nucleic acid. Suitable probes include polypeptide nucleic acids, as described in Nielsen (1991) *Science*, 254, 1497-1500.

Such nucleic acid molecules can be detected and/or isolated by specific hybridization e.g. under high stringency conditions. "Stringency conditions" for hybridization is a term of art that refers to the incubation and wash conditions, e.g. conditions of temperature and buffer concentration, which permit hybridization of a particular nucleic acid to a second nucleic acid; the first nucleic acid may be perfectly complementary, i.e. 100%, to the second, or the first and second may share some degree of complementarity, which is less than perfect, e.g. 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology (2011) John Wiley & Sons). The exact conditions which determine the stringency of hybridization depend not only on ionic strength, e.g. 0.2×SSC, 0.1×SSC of the wash buffers, temperature, e.g. 23° C., 42° C., 68° C., etc. and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause (1991) *Methods in Enzymology*, 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

The nucleic acid molecules of the invention can optionally comprise additional non-coding sequences such as non-coding 3' and 5' sequences (including, e.g., regulatory sequences) that may be homologous or heterologous to a DGAT gene. Alternatively or in addition, any of the provided nucleic acid molecules can optionally further comprise an additional nucleic acid sequence of at least 50, at least 60, at least 70, at least 80, at least 90, at least 100, at least 150, at least 200, at least 250, at least 300, at least 350, at least 400, at least 450, at least 500, at least 550, at least 600, at least 700, at least 800, at least 900, at least 1000, or at least 1500 nucleotides from a photosynthetic organism. The nucleic acid molecules and polypeptides described herein can be used in any of the methods of the invention, and may be included in any of the vectors or recombinant microorganisms of the invention. Nucleic acid molecules comprising sequences that encode DGAT are provided for use in host microorganisms and methods for producing TAG.

Other Modifications

The invention also provides further variants of the nucleotide sequences of the invention. In some embodiments, the nucleotide sequence variants encode fragments or variants of the polypeptides as described herein. In some embodiments, the nucleotide sequence variants are naturally-occurring. In other embodiments, the nucleotide sequence variants are non-naturally-occurring, such as those induced by various mutagens and mutagenic processes. In certain embodiments, the nucleotide sequence variants are a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-91, and Stemmer (1994) *Proc. Natl. Acad. Sci. USA* 91, 10747-51. Chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

For optimal expression of a recombinant protein, in certain instances it may be beneficial to employ coding sequences that produce mRNA with codons preferentially used by the host cell to be transformed ("codon optimization"). Thus, for enhanced expression of transgenes, the codon usage of the transgene can be matched with the specific codon bias of the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some examples, only a portion of the codons is changed to reflect a preferred codon usage of a host microorganism. In certain examples, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain examples, the non-native nucleic acid sequence encoding a DGAT is codon optimized for expression in a photosynthetic microorganism, e.g., a *cyanobacterium* or a eukaryotic microalga. In some aspects, the nucleic acid molecules of the invention encode fusion proteins that comprise a DGAT. For example, the nucleic acids of the invention may comprise polynucleotide sequences that encode the amino-terminus of a putative chloroplast inner envelope glucose-6-phosphate/ phosphate antiporter or a portion thereof, glutathione-S-transferase (GST) or a portion thereof, thioredoxin or a portion thereof, maltose binding protein or a portion thereof, poly-histidine (e.g. $His_6$), poly-HN, poly-lysine, a hemagglutinin tag sequence, HSV-Tag and/or at least a portion of HIV-Tat fused to the DGAT-encoding sequence.

Nucleic Acid Constructs

The invention also provides constructs comprising a nucleic acid sequence encoding a DGAT that can further include one or more sequences that regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that may be operably linked to the gene of interest (e.g., a DGAT gene) in an expression construct or "expression cassette." In some examples of the foregoing, the promoter is regulatable, e.g., inducible. In other examples of the foregoing, the promoter may be constitutive. The promoter in some examples can be an algal promoter or derived from an algal promoter.

In examples where the nucleic acid construct does not contain a promoter in operable linkage with the nucleic acid sequence encoding the gene of interest (e.g., a DGAT gene) the nucleic acid sequence can be transformed into the cells such that it becomes operably linked to an endogenous promoter by, e.g., homologous recombination, site specific integration, and/or vector integration. In some examples, genomic host sequences included in a nucleic acid construct for mediating homologous recombination into the host genome can include gene regulatory sequences, for example, a promoter sequence, that can regulate expression of a DGAT gene of the nucleic acid construct. In such embodiments, the transgene(s) of the construct can become operably linked to a promoter that is endogenous to the host microorganism. In some embodiments, the endogenous promoter(s) are regulatable, e.g., inducible. Alternatively the DGAT gene can be operably linked to an endogenous promoter that is constitutive and/or active under nitrogen replete conditions.

A promoter operably linked to a nucleic acid sequence encoding a DGAT may be a promoter that is heterologous with respect to the DGAT gene. Promoters considered for use in regulating acyltransferase genes in eukaryotes can include, without limitation, inducible promoters such as a GAL, MET, Lys, or Leu promoter, or a nmt1 thiamine-repressible promoter, a uracil regulatable promoter (e.g., Watt et al. (2008) *PLoS One* 3: e1428) for example from a yeast or fungus, or a Tet-On or Tet-Off promoter. Other eukaryotic promoters as they are known in the art can also be employed, such as the SV40 promoter and the Cauliflower Mosaic Virus (CaMV) promoter, active fragments thereof, or hybrid promoters that include fragments of known eukaryotic promoters such as the SV40, CaMV, and nopaline synthase promoters.

In some embodiments of the foregoing invention, the promoter may be an inducible promoter, i.e., a promoter that mediates transcription of an operably linked gene in response to a particular stimulus. Such promoters may be advantageous, e.g., to minimize any deleterious effects on the growth of the host cell and/or to maximize production of TAG. An inducible promoter can be responsive to, e.g., light or dark or high or low temperature, and/or can be responsive to specific compounds. The inducible promoter may be a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/ or BTH (U.S. Pat. No. 5,689,044), or the like, or some combination thereof. An inducible promoter can also be responsive to light or dark (U.S. Pat. No. 5,750,385, U.S. Pat. No. 5,639,952), metals (Quinn et al. (2003) *Eukaryot. Cell* 2, 995-1002) or temperature (U.S. Pat. No. 5,447,858; Abe et al. (2008) *Plant Cell Physiol.* 49, 625-32; Shroda et al. (2000) *Plant J.* 21, 121-31). The foregoing list is exemplary and not limiting. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

Inducible promoters from eukaryotic algae include a NR promoter (ammonia regulated; Wang et al. (2004) *J. Appl. Phycol.* 16: 11-16), nia promoter (U.S. Pat. No. 7,642,405), CYC6 (copper inducible, nickel and cobalt repressible) or CA1 promoter ($CO_2$-regulated; Ferrante et al. (2008) *PLos One* 3: e3200), as well as an algal Pnr (nitrogen-regulated) promoter (Poulsen and Kroger (2005) *FEBS J.* 3413-3423), an algal inorganic phosphate transporter promoter (Wurch et al. (2011) *Environ. Microbiol.* 113: 468-481), or other phosphate-status regulated promoter from algae, e.g, a PNP or PSR promoter (Yehudai-Resheff et al. (2007) *The Plant Cell* 19: 1023-1038). Further examples of promoters that may be induced by nitrogen limitation or depletion include but are not limited to: ammonium or ammonia transporter gene promoters (see, for example, Wurch et al. (2011) *Environ Microbiol.* 13: 468-481); glutamine synthetase transporters (e.g., Miller et al (2010) *Plant Physiology* 154: 737-52) or other promoters of genes upregulated at the transcriptional level during nitrogen depletion, including those disclosed in co-pending U.S. patent application Ser. No. 13/536,345, entitled "Regulation of Toxin and Antitoxin Genes for Biological Containment" filed Jun. 28, 2012, or active fragments of any thereof. The promoter can alternatively or in addition be regulated by phosphate depletion, and can be, for example, a PNPase gene promoter (Yehudai-Reseheff et al. (2007) *The Plant Cell* 19: 1023-1038); an inorganic phosphate transporter gene promoter (Wurch et al. (2011) *Environ Microbiol.* 13: 468-481), a phosphate permease gene promoter, or any disclosed in co-pending U.S. patent application Ser. No. 13/536,345, entitled "Regulation of Toxin and Antitoxin Genes for Biological Containment" filed Jun. 28, 2012, or an active fragment thereof. Candidate copper depletion-regulated promoters include those of CTR-type copper ion transporter genes (Castruita et al. (2011) *The Plant Cell* 23: 1273-1292), as well as CYC6 and CPX1 algal promoters (Quinn et al. (2000) *J. Biol. Chem.* 275: 6080-6089). Promoters regulated by iron deficiency may include, for example, the FOX1 gene or the FTR1 gene (La Fontaine et al. (2002) *Eukaryotic Cell* 1: 736-757).

Specifically considered are promoters of the genes known to be transcribed under nitrogen replete conditions. For example, promoters used to regulate DGAT genes can be active under conditions where the algae are proliferating, e.g., promoters that are active in the absence of nutrient limitation, such as, for example the *Nannochloropsis* promoters disclosed in co-pending U.S. patent application Ser. No. 13/486, 930, entitled "Promoters and Terminators for Use in Eukaryotic Cells" filed Jun. 1, 2012, as well as in co-pending U.S. patent application Ser. No. 13/536,345, entitled "Regulation of Toxin and Antitoxin Genes for Biological Containment" filed Jun. 28, 2012. Additional examples of algal promoters include the *Nannochloropsis oceanica* vcp promoter sequence, which is regulated by light-exposure, (U.S. 2009/ 317,904); the a light-responsive fcpA promoter from *Phæodactylum tricornutum* (U.S. Pat. No. 6,027,900); the *Chlamydomonas* psaD promoter (Fisher and Rochaix (2001) *Mol Genet Genet.* 265: 888-894), as well as RuBisCo small sub-unit (ssu) promoters (Walker et al. (2004) *Plant Cell Reports* 23:727-735; Chen et al. (2008) *J. Phycol.* 44:768-776); the *Cyclotella cryptica* acc promoter, and *Chlorella* viral promoters (U.S. Pat. No. 6,252,140; U.S. Pat. No. 6,316,224). Also considered are promoters that are associated with orthologous genes in other species. For example, a gene of one algal species that is transcribed under nutrient replete or nitrogen replete conditions can be used to identify an orthologous gene in a second algal species, and the promoter of the gene in the second species can be isolated and tested for its activity under the desired culture conditions.

The examples or promoters provided are not limiting with regard to the promoters that may be used in constructs for expression acyltransferases such as DGATs. Specifically considered are active fragments of promoters provided herein or disclosed in the art and promoters that comprise multimers of promoters or promoter fragments, as well as hybrid promoters such as but not limited to promoters that may include sequences of two or more different algal promoters (e,g, the HSP70-RBCS promoter (Schroda et al. (2000) *Plant J.* 21: 121-131)), or hybrid promoters that may comprise algal and non-algal sequences, such as, for example, at least a portion of an SV40 promoter or CaMV promoter juxtaposed with at least a portion of an algal promoter. A promoter may comprise multimers of a sequence, including multimers of a hybrid promoter sequence.

A promoter used to regulate a DGAT or acyltransferase gene in a eukaryote can also be a synthetic promoter, for example, a promoter that includes a DNA binding domain that can be recognized and bound by an engineered transcription factor positioned upstream of a minimal promoter that is operable in the host microorganism. The microorganism can include an exogenous gene encoding a synthetic transcription factor that binds the synthetic promoter. The synthetic transcription factor can include, in addition to a DNA binding domain that recognizes the synthetic promoter, an activation domain (e.g., VP16, CREB, GAL10, GCN4) and a regulatory domain, where the regulatory domain may bind one or more compounds that can be added to the culture medium to induce or repress transcription (Weber and Fussenegger (2011) *Curr Opinion in Chem. Biol.* 15: 414-420).

Likewise, a wide variety of transcriptional terminators can be used for expression vector construction. Nonlimiting examples of possible terminators can include, but are not limited to terminators associated with an algal GAPDH gene or a tubulin gene (e.g., SEQ ID NO:8), as well as those disclosed in co-pending U.S. patent application Ser. No. 13/486,930, entitled "Promoters and Terminators for Use in Eukaryotic Cells" filed Jun. 1, 2012.

In addition to a DGAT gene, one or more additional genes can optionally be included in a recombinant microorganism as provided herein, where the one or more additional genes may include, for example, one or more genes encoding enzymes or proteins of the fatty acid synthesis pathway and/ or one or more genes encoding enzymes or proteins that may enhance TAG synthesis, one or more genes that may enhance photosynthesis or carbon-fixation, and/or one or more reporter genes or selectable markers. For example, the construct or expression cassette may further comprise a heterologous protein encoding sequence, for example, encoding a glycerolphosphate acyltransferase (GPAT), a lysophosphatidic acid acyltransferase (LPAAT), and/or a monoacylglycerol acyltransferase (MGAT).

The present invention also provides for nucleotide constructs comprising a nucleotide sequence encoding a localization peptide as already described herein. The nucleotide sequence encoding a localization peptide can be fused in frame with any heterologous gene for ectopic expression in a recombinant microorganism. In one aspect, the nucleotide sequence encoding a localization peptide is fused in frame with a DGAT-encoding sequence. As nonlimiting examples the localization peptide can direct a polypeptide to the endoplasmic reticulum or a region thereof, or to a chloroplast or a region thereof. In a particular aspect, the nucleotide sequence encoding a localization peptide is fused in frame with a nucleotide sequence encoding an amino acid having at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one or more of SEQ ID NOs:2, 4, 18, 24, 36, 40, 46, 50, 56, and 78.

An isolated nucleic acid construct of the present invention can include the sequences disclosed herein that encode a DGAT or other polypeptide in a vector, such as, but not limited to, an expression vector. A vector can be a nucleic acid that has been generated via human intervention, including by recombinant means and/or direct chemical synthesis, and can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism. A vector can be an expression vector that includes one or more specified nucleic acid "expression control elements" that permit transcription and/or translation of a particular nucleic acid in a host cell. The vector can be a plasmid, a part of a plasmid, a viral construct, a nucleic acid fragment, or the like, or a combination thereof.

The vector can be a high copy number vector, a shuttle vector that can replicate in more than one species of cell, an expression vector, an integration vector, or a combination thereof. Typically, the expression vector can include a nucleic acid comprising a gene of interest operably linked to a promoter in an "expression cassette," which can also include, but is not limited to, a localization peptide encoding sequence, a transcriptional terminator, a ribosome binding site, a splice site or splicing recognition sequence, an intron, an enhancer, a polyadenylation signal, an internal ribosome entry site, and similar elements. Additionally, the present invention can involve recombinant microorganisms transformed with an isolated nucleic acid comprising a gene of interest under control of a heterologous promoter. Alternatively, if the vector does not contain a promoter operably linked with an isolated nucleic acid comprising a gene of interest, the isolated nucleic acid can be transformed into the microorganisms or host cells such that it becomes operably linked to an endogenous promoter by homologous recombination, site specific integration, and/or vector integration.

In some examples, the present invention additionally provides recombinant microorganisms or host cells transformed with an isolated nucleic acid comprising a gene of interest that is operably linked to one or more expression control elements. In some instances, it can be advantageous to express the protein at a certain point during the growth of the recombinant microorganism, e.g., to minimize any deleterious effects on the growth of the recombinant microorganism and/or to maximize production of TAG. In such instances, one or more exogenous genes introduced into the recombinant microorganism or host cell can be operably linked to an inducible promoter, which mediates transcription of an operably linked gene in response to a particular stimulus.

Transformation vectors can additionally or alternately include a selectable marker. Transformed cells can be selected based upon the ability to grow in the presence of the antibiotic and/or other selectable marker under conditions in which cells lacking the resistance cassette or auxotrophic marker could not grow. Further, a non-selectable marker may be present on a vector, such as a gene encoding a fluorescent protein or enzyme that generates a detectable reaction product.

A vector comprising an isolated nucleic acid comprising a gene of interest can also be an integration vector that includes one or more sequences that promote integration of the gene of interest or a gene expression cassette into the genome of the host microorganism or host cell. For example, an integration vector can include at least one sequence of at least 20, at least 30, at least 40, at least 50, at least 100, at least 200, at least 300, at least 400, at least 500, or at least 600 nucleotides with homology to a sequence in the genome of the host organism to allow integration of the gene of interest or gene expression cassette into the genome of the host microorganism or host cell to occur via homologous recombination. In some examples, the gene or gene expression cassette is flanked by sequences homologous to a region of the host chromosome to promote integration of the gene of interest or gene expression cassette into the host chromosome. Alternatively or in addition, an integration vector can include one or more sequences that promote site-specific recombination or random integration such as, but not limited to, sequences recognized by recombinases, integrases, or transposases. In some embodiments, the integration vector can further include a gene encoding a recombinase, integrase, or transposase.

Microorganisms and Host Cells and Cultures

A recombinant microorganism or host cell as provided herein comprises a non-native gene encoding a DGAT, wherein the recombinant microorganism produces TAG. For example, a recombinant microorganism or host cell as provided herein can include a non-native gene encoding a DGAT and can produce a greater amount of triglyceride than is produced by a control recombinant microorganism or host cell substantially identical to the recombinant microorganism or host cell, but lacking a non-native gene encoding a diacylglycerol acyltransferase. The recombinant microorganism or host cell may produce more TAG than a control recombinant microorganism or host cell under nitrogen replete conditions.

Recombinant microorganisms or host cells may be of prokaryotic or eukaryotic origin, including, without limitation, fungi, heterokonts, algae, eubacteria, archaebacteria, green nonsulfur bacteria, purple nonsulfur bacteria, or cyanobacteria.

Non-photosynthetic microorganisms and host cells such as fungi and non-algal stramenophiles are considered as hosts that can include non-native DGAT genes. Oleaginous yeasts, including but not limited to *Aspergillus niger, Yarrowia lipolytica, Cryptococcus curvatus, Cryptococcus terricolus, Candida species, Lipomyces starkeyi, Lipomyces lipofer, Endomycopsis vernalis, Rhodotorula glutinis,* and *Rhodotorula gracilis* or other fungi, including but not limited to species of *Aspergillus, Trichoderma, Neurospora, Fusarium,*

*Humicola, Rhizomucor, Kluyveromyces, Pichia, Mucor, Myceliophtora, Penicillium, Phanerochaete, Chrysosporium, Saccharomyces,* and *Schizosaccharomyces,* are also encompassed as microorganisms and host cells. Further considered are *Labyrinthulomycete* species (e.g., *Thraustichytrium, Ulkenia,* and *Schizochytrium* species).

In some embodiments, the microorganism or host cell can be a bacterium, such as, but not limited to, an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* or *Zymomonas* species. Photosynthetic bacteria, including for example, green sulfur bacteria, purple sulfur bacteria, green nonsulfur bacteria, purple nonsulfur bacteria, or cyanobacteria can be used.

Recombinant host cells can be photosynthetic organisms. Photosynthetic organisms include higher plants (i.e., vascular plants), bryophytes, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pico-plankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria).

Cyanobacterial species that can be used for production of TAG include, without limitation, *Agmenellum, Anabaena, Anabaenopsis, Anacystis, Aphanizomenon, Arthrospira, Asterocapsa, Borzia, Calothrix, Chamaesiphon, Chroococcus, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Glœobacter, Glœocapsa, Glœothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus.* For example, the recombinant photosynthetic microorganism can be a *Cyanobium, Cyanothece,* or *Cyanobacterium* species, or further alternatively, the recombinant photosynthetic microorganism can be a *Glœobacter, Lyngbya* or *Leptolyngba* species. Alternatively, the recombinant photosynthetic microorganism can be a *Synechococcus, Synechocystis,* or *Thermosynechococcus* species. A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced.

Eukaryotic microalgae for use in the invention, include without limitation, *Achnanthes, Amphiprora, Amphora, Ankistrodesmus, Asteromonas, Bœkelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Glœothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochytrium, Skeletonema, Spyrogyra, Stichococcus, Tetraselmis, Viridiella,* or *Volvox* species. In a particular aspect, *Nannochloropsis* is used as the host cell, i.e. a recombinant algal cell.

In one aspect, provided herein is a recombinant eukaryotic alga that includes a non-native gene encoding a diacylglycerol acyltransferase (DGAT), in which the eukaryotic alga produces a greater amount of TAG than is produced by a eukaryotic alga substantially identical to the recombinant eukaryotic alga, but lacking a non-native gene encoding a diacylglycerol acyltransferase. The recombinant eukaryotic alga that includes a non-native gene encoding a diacylglycerol acyltransferase (DGAT) can produce a greater amount of TAG than is produced by a substantially identical eukaryotic alga when the algae are cultured under conditions in which inorganic carbon is substantially the sole source of carbon in the growth medium. Additionally, the recombinant eukaryotic alga that includes a non-native gene encoding a diacylglycerol acyltransferase (DGAT) can produce a greater amount of TAG than is produced by a eukaryotic alga substantially identical to the recombinant eukaryotic alga, when the algae are cultured under nitrogen replete conditions. For example, a culture of a recombinant eukaryotic alga can be maintained under nutrient replete conditions during the production period, and the culture can produce TAG during a culture period in which the cells of the culture are dividing.

A non-native gene encoding a DGAT can encode any DGAT, for example, a eukaryotic DGAT, which can be a DGAT1, DGAT2, DGAT3, DGAcT, and/or a prokaryotic DGAT or wax synthase (WS) (e.g., a prokaryotic WS/DGAT) that has DGAT activity. The non-native gene can encode a DGAT that is a variant of a naturally-occurring DGAT, such as a DGAT having at least 80%, at least 85%, at least 90%, or at least 95% amino acid sequence identity to a naturally-occurring DGAT or an active fragment thereof. The non-native gene can encode a DGAT that is a truncated variant of a naturally-occurring DGAT, such as an N-terminally or C-terminally truncated variant of a naturally-occurring DGAT or a DGAT having at least 80%, at least 85%, at least 90%, or at least 95% amino acid sequence identity to a naturally-occurring DGAT. Additionally or alternatively, recombinant eukaryotic alga can include a non-native gene encoding a DGAT that has at least 80%, at least 85%, at least 90%, or at least 95% amino acid sequence identity to a naturally-occurring DGAT or an active fragment thereof and can further include one or more additional amino acid sequences, such as, but not limited to, one or more amino acid sequences that can direct the DGAT to a location within the cell, such as, for example, a plastid or a region thereof and/or the endoplasmic reticulum or a region thereof.

DGAT genes utilized according to the present invention may be isolated from any organism, including eukaryotic and prokaryotic organisms, and can be any disclosed herein. Eukaryotic organisms having a DGAT gene are well-known in the art, and include various animals (e.g., mammals, fruit flies, nematodes), plants, parasites, and fungi (e.g., yeast such as *S. cerevisiae* and *Schizosaccharomyces pombe*). Examples of prokaryotic organisms include certain actinomycetes, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of actinomycetes that have one or more genes encoding a DGAT activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having a DGAT activity include members of the genera *Acinetobacter*, such as *A. calcoaceticus, A. baumanii*, and *A. baylii*. In certain embodiments, a DGAT enzyme is isolated from *Acinetobacter baylii* sp. ADP1, a gram-negative triglyceride forming prokaryote, which contains a well-characterized DGAT (AtfA).

In further examples, a recombinant eukaryotic alga as provided herein can include a non-native gene encoding a type-1 or a type-2 DGAT from a eukaryote, such as, for example, a fungus, yeast, protozoan, animal, alga, or plant, or a variant thereof having at least 80%, at least 85%, at least 90%, or at least 95% amino acid sequence identity to the naturally-occurring DGAT1, DGAT2, or DGAT3 or an active fragment thereof, and can include a deletion, for example, a truncation, with respect to the naturally-occurring DGAT amino acid sequence, and/or can include one or more additional sequences, such as, but not limited to, a cellular localization sequence. In some examples, the DGAT1, DGAT2, or DGAT3 encoded by the non-native gene comprises a sequence at least 80%, at least 85%, at least 90%, or at least 95% identical to SEQ ID NO:2, SEQ ID NO:4, SEQ ID NO:18, SEQ ID NO:24, SEQ ID NO:36, SEQ ID NO:78, SEQ ID NO:80, SEQ ID NO:82, SEQ ID NO:84, SEQ ID NO:86, and/or an active portion thereof. Alternatively or in addition, a recombinant eukaryotic alga as provided herein can include a non-native gene encoding a wax synthase/diacylglycerol transferase (WS/DGAT) from a prokaryote or a variant thereof having at least 80%, at least 85%, at least 90%, or at least 95% amino acid sequence identity to the naturally-occurring prokaryotic WS/DGAT or an active fragment thereof, and can include a deletion, for example, a truncation, with respect to the naturally-occurring DGAT amino acid sequence, and/or can include one or more additional sequences, such as, but not limited to, a cellular localization sequence. In some examples, the prokaryotic WS/DGAT encoded by the non-native gene comprises a sequence at least 80%, at least 85%, at least 90%, or at least 95% identical to SEQ ID NO:40, SEQ ID NO:46, SEQ ID NO:50, SEQ ID NO:56, and/or an active portion thereof.

The recombinant host cell may comprise, e.g., any of the nucleic acid sequences encoding a DGAT described herein and may comprise any of the nucleic acid sequences encoding a localization peptide described herein (e.g., SEQ ID NOs:30, 74, and/or 76). Further, the recombinant host cells may comprise, e.g., any of the vectors described herein.

In some aspects, the nucleic acid sequence encoding the DGAT gene is heterologous with respect to the recombinant host cell, and can be a DGAT gene derived from any species, including plant, animal, or microbial species.

Additionally or alternatively, the DGAT gene may be homologous with respect to the host organism. For example, the non-native DGAT gene may be a DGAT gene that is native to the host microorganism and is introduced into the recombinant microorganism in an expression cassette that allows regulated expression or overexpression of the endogenous DGAT gene. Additionally, the DGAT gene may be endogenous to the microorganism and a heterologous promoter may be introduced into the host microorganism such that it becomes juxtaposed with and operably linked to the endogenous DGAT gene.

The recombinant microorganism can comprise a non-native gene encoding a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:2, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:4, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:18, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:24, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:36, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:40, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:46, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:50, a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:56,
- a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:78,
- a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:80,
- a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:82,
- a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:84,
- a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:86, and/or
- a functional fragment of any one of the DGAT listed sequences.

Additionally, the recombinant microorganism can comprise a non-native gene encoding the DGAT of SEQ ID NOs: 2, 4, 18, 24, 36, 40, 46, 50, 56, 78, 80, 82, 84, and/or 86.

Alternatively, the recombinant microorganism can comprise a non-native gene encoding a DGAT with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NOs: 2, 4, 18, 24, 36, 40, 46, 50, 56, 78, 80, 82, 84 and/or 86; and/or can encode a DGAT with at least 90%, at least 95%, at least 96%, at least 97%, at least 98%, or at least 99% sequence identity to SEQ ID NOs: 2, 4, 18, 24, 36, 40, 46, 50, 56, 78, 80, 82, 84, and/or 86.

Illustrative examples of recombinant microorganisms that express a non-native DGAT gene include recombinant microorganisms such as but not limited to *Nannochloropsis gaditana* that express a non-native gene encoding a DGAT having at least 85% identity, for example at least 90% or at least 95% identity to SEQ ID NOs: 2, 4, 18, 24, 36, 40, 46, 50, 56, 78, 80, 82, 84, and/or 86.

In a further example, the recombinant microorganism comprises a non-native gene encoding a type 2 DGAT with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 18, 24, and/or 36.

In some examples, the recombinant microorganism comprises a non-native gene encoding a DGAT with at least 30%, at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleotide sequence of SEQ ID NOs:1, 3, 17, 23, 35, 39, 45, 49, 55, 77, 79, 81, 83, and/or 85, and/or to a fragment of the nucleotide sequence that encodes a functional fragment of the DGAT. In some aspects, the recombinant host cell is a photosynthetic host cell, and the non-native nucleic acid sequence encoding the DGAT is codon optimized for expression in the host cell.

Additionally or alternatively, the recombinant microorganism can comprise a non-native gene, in addition to the non-native DGAT, which encodes a polypeptide for the production of a lipid, such as, for example, a non-native gene encoding an enzyme for the production of fatty acids, fatty acid derivatives, and/or glycerolipids. in the production of a fatty acid product not normally produced by the microorganism. For example, a recombinant microorganism as disclosed herein can include a non-native gene encoding a DGAT and can further include a non-native gene encoding an enzyme that participates in the production of glycerolipids, including, but not limited to, a glycerolphosphate acyltransferase (GPAT), a lysophosphatidic acid acyltransferase (dehydrogenase) (LPAAT), a phosphatidic acid phosphatase (PAP), a monoacylglycerol acyltransferase (MGAT), and/or another DGAT.

In further examples, the recombinant microorganism produces a greater amount of TAG than is produced by a control algal cell. For example the recombinant algal cell comprising a DGAT as described herein results in a higher production level of TAG by the recombinant microorganism than the production level in a control microorganism, where the control microorganism is cultured under substantially the same conditions and is substantially identical to the microorganism expressing the non-native DGAT gene in all respects, with the exception that the control microorganism does not express a non-native DGAT gene. In particular examples, the recombinant microorganism can be a photosynthetic microorganism such as a recombinant algal cell.

In some aspects, the amount of TAG produced by a culture of the recombinant microorganism expressing a non-native DGAT gene is at least 10%, at least 15%, at least 20%, at least 25%, at least 30%, at least 40%, at least 50%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, at least 600%, at least 625%, at least 650%, at least 675%, at least 700%, at least 725%, at least 750%, at least 775%, at least 800%, at least 825%, at least 850%, at least 875%, at least 900%, at least 925%, at least 950%, at least 975%, or at least 1000% greater than the amount of TAG produced by a control host cell that does not express the non-native DGAT gene.

In certain aspects, the recombinant microorganism can produce more TAG when compared to a control host cell under nitrogen replete conditions. Additionally, in certain examples, the recombinant microorganism can produce a greater amount of TAG after about one, or two or three days of culturing under nitrogen replete conditions.

Additionally, a culture of a recombinant photosynthetic microorganism as described herein is provided. The culture can produce a greater amount of TAG than is produced by a control culture substantially identical in all respects except that the recombinant photosynthetic microorganism of the control culture does not include or does not express the non-native gene encoding a DGAT. Preferably, a culture of the recombinant photosynthetic microorganism that includes a non-native gene encoding a DGAT (and optionally a non-native gene encoding a polypeptide that participates in the production of a lipid) produces a greater amount of fatty acid product, for example TAG, than is produced by a culture of an otherwise substantially identical recombinant photosynthetic microorganism that lacks the non-native gene encoding a DGAT. For example, a photoautotrophic culture of the recombinant photosynthetic microorganism that includes a non-native gene encoding a DGAT (and optionally a non-native gene encoding a polypeptide that participates in the production of a lipid) can preferably produce a greater amount of a fatty acid product, for example TAG, than is produced by a photoautotrophic culture of an otherwise identical photosynthetic microorganism that lacks the non-native gene encoding the DGAT. Additionally or alternatively, a culture of the recombinant photosynthetic microorganism can achieve a higher cell density while producing TAG under photoautotrophic conditions, e.g., using inorganic (non-reduced) carbon as the carbon source for production of the fatty acid product such as TAG.

Transformation of Microorganisms and Host Cells

A vector comprising an isolated nucleic acid comprising a gene of interest can be introduced into a host cell via conventional transformation and/or transfection techniques. The terms "transformation," "transfection," "conjugation," and "transduction," as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

Host cells such as plants for use in the invention can be transformed by any feasible means, including, without limitation, the use of *Agrobacterium*, particle gun-mediated transformation, laser-mediated transformation, or electroporation. Algae and photosynthetic bacteria can be transformed by any suitable methods, including, as nonlimiting examples, natural DNA uptake (Chung et al. (1998) *FEMS Microbiol. Lett.* 164, 353-61; Frigaard et al. (2004) *Methods Mol. Biol.* 274, 325-40; Zang et al. (2007) *J. Microbiol.* 45, 241-45), conjugation, transduction, glass bead transformation (Kindle et al. (1989) *J. Cell Biol.* 109, 2589-601; Feng et al. (2009) *Mol. Biol. Rep.* 36, 1433-39; U.S. Pat. No. 5,661,017), silicon carbide whisker transformation (Dunahay et al. (1997) *Methods Mol. Biol.* 62, 503-09), biolistics (Dawson et al. (1997) *Curr. Microbiol.* 35, 356-62; Hallmann et al. (1997) *Proc. Natl. Acad. USA* 94, 7469-74; Jakobiak et al. (2004) *Protist* 155, 381-93; Tan et al. (2005) *J. Microbiol.* 43, 361-65; Steinbrenner et al. (2006) *Appl Environ. Microbiol.* 72, 7477-84; Kroth (2007) *Methods Mol. Biol.* 390, 257-67; U.S. Pat. No. 5,661,017) electroporation (Kjaerulff et al. (1994) *Photosynth. Res.* 41, 277-83; Iwai et al. (2004) *Plant Cell Physiol.* 45, 171-75; Ravindran et al. (2006) *J. Microbiol. Methods* 66, 174-76; Sun et al. (2006) *Gene* 377, 140-49; Wang et al. (2007) *Appl. Microbiol. Biotechnol.* 76, 651-57; Chaurasia et al. (2008) *J. Microbiol. Methods* 73, 133-41; Ludwig et al. (2008) *Appl. Microbiol. Biotechnol.* 78, 729-35), laser-mediated transformation, or incubation with DNA in the presence of or after pre-treatment with any of poly(amidoamine) dendrimers (Pasupathy et al. (2008) *Biotechnol. J.* 3, 1078-82), polyethylene glycol (Ohnuma et al. (2008) *Plant Cell Physiol.* 49, 117-20), cationic lipids (Muradawa et al. (2008) *J. Biosci. Bioeng.* 105, 77-80), dextran, calcium phosphate, or calcium chloride (Mendez-Alvarez et al. (1994) *J. Bacteriol.* 176, 7395-97), optionally after treatment of the cells with cell wall-degrading enzymes (Perrone et al. (1998) *Mol. Biol. Cell* 9, 3351-65). *Agrobacterium*-mediated transformation can also be performed on algal cells, for example after removing or wounding the algal cell wall (e.g., WO 2000/62601; Kumar et al. (2004) *Plant Sci.* 166, 731-38). Biolistic methods are particularly successful for transformation of the chloroplasts of plant and eukaryotic algal species (see, for example, Ramesh et al. (2004) *Methods Mol. Biol.* 274, 301-07; Doestch et al. (2001) *Curr. Genet.* 39, 49-60; U.S. Pat. No. 7,294,506; WO 2003/091413; WO 2005/005643; and WO 2007/133558, all incorporated herein by reference in their entireties).

Methods of Peptide Targeting/Localization

The invention also encompasses methods of targeting a peptide for expression in the chloroplast. This can be achieved by fusing a nucleic acid coding for a localization peptide with at least 80% sequence identity to SEQ ID NO:74 and/or SEQ ID NO:76 in frame with a nucleic acid coding for desired peptide to be expressed, and then expressing this fused nucleic acid in a cell of interest. As used herein, a fused nucleic acid can be "expressed" by means described elsewhere herein and by other means well known to those skilled in the art.

SEQ ID NO:74 comprises the first transmembrane domain of a putative chloroplast inner envelope glucose-6-phosphate/phosphate antiporter from *Nannochloropsis gaditana*. SEQ ID NO:76 comprises the first and second transmembrane domains of a putative chloroplast inner envelope glucose-6-phosphate/phosphate antiporter from *Nannochloropsis gaditana*. While the invention is not bound by any one theory, it is hypothesized that a protein bearing one or both of these transmembrane domains, also known as localization or targeting sequences, at its amino terminus is thus directed by intracell transport machinery to the inner membrane surface of a chloroplastic membrane.

In some examples, the protein to which the localization sequence is fused can be a PDAT, a GPAT, a LPAAT, a MGAT, and/or a DGAT. Additionally or alternatively, the protein to which the targeting sequence is fused can be a DGAcT. While the invention is not bound by any one theory, it is believed that the chloroplastic environment is rich in substrate pools for acetyl coenzyme A, so TAG production can be enhanced by targeting a DGAcT to an inner-chloroplastic environment.

Methods of Producing Triglyceride (TAG)

The invention also encompasses methods of producing TAG by culturing the recombinant microorganisms and host cells described herein, under conditions in which TAG is produced. The methods can further comprise isolating TAG. Additionally, the expression of a polypeptide encoded by the nucleic acid molecules described herein can be induced in the recombinant microorganism to produce the TAG. In some examples, the TAG production occurs during nitrogen-replete culture conditions. Additionally or alternatively, the TAG production occurs during photoautotrophic culture conditions. Additionally or alternatively, the TAG production occurs while the host organism is actively growing and dividing.

As discussed previously, the presention invention further provides for a culture comprising the recombinant microorganisms producing TAG. Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. Non-limiting examples of selected and/or controlled conditions can include the use of a defined medium (with known characteristics such as pH, ionic strength, nitrogen concentration, and/or carbon source), specified temperature, oxygen tension, carbon dioxide levels, growth in a bioreactor, or the like, or combinations thereof. In some embodiments, the microorganism or host cell can be grown heterotrophically, using a reduced carbon source, or mixotrophically, using both light and a reduced carbon source. Additionally or alternatively, the microorganism or host cell can be cultured photoautotrophically. When growing photoautotrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. Under conditions in which inorganic carbon is substantially the sole source of carbon, if an organic carbon molecule or compound is provided in the culture medium, it generally cannot be taken up and/or metabolized by the cell for energy and/or typically is not present in an amount sufficient to provide sustainable energy for the growth of the cell culture. However, microorganisms growing heterotrophically do utilize organic carbon provided in the culture medium. Thus, the present invention includes a process for converting a carbon source to TAG comprising contacting the carbon source with a recombinant microorganism or host cell of the invention. In some aspects the carbon source is an inorganic carbon source and in other aspects the carbon source is an organic carbon source.

Microorganisms and host cells that can be useful in accordance with the methods of the present invention can be found in various locations and environments throughout the world. Without wishing to be bound by theory, it is observed that, perhaps as a consequence of their isolation from other species and their evolutionary divergence, the particular growth medium for optimal growth and generation of lipid and/or other hydrocarbon constituents can vary. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx) (visited May 4, 2012); Culture Collection of Algae and Protozoa (www.ccap.ac.uk) (visited May 4, 2012); and Katedra Botaniky (botany.natur.cuni.cz/algo/caup-media.html) (visited May 4, 2012).

In some embodiments, the nitrogen content of the medium can be "replete", that is, the level of nitrogen is not limiting to culture propagation. The amount of nitrogen required in a replete nitrogen culture medium can vary depending on the algal strain and other culture conditions, but preferably is at least about 0.25 mM, at least 0.5 mM, or at least 0.8 mM, such as at least 1 mM, at least 2 mM, at least 3 mM, at least 4 mM, at least 5 mM, at least 6 mM, at least 7 mM, or at least 8 mM nitrogen, which is preferably supplied as ammonia and/or nitrate, but can be supplied as any utilizable nitrogen source compound. In some embodiments, the culture medium can be nitrogen replete and can lack a supplementary organic carbon source. In some embodiments, the culture medium can be nutrient replete, where no nutrients (not including a carbon source) are limiting for culture propagation, and the culture medium can lack a supplementary organic carbon source.

In some examples, a culture medium used during at least a portion of the production period may be nitrogen limited but not necessarily nitrogen depleted. For example, the amount of nitrogen provided in the culture medium might permit culture proliferation but be less than the amount required for optimal growth (e.g., optimal rates of biomass accumulation or cell division). A "nitrogen deplete" medium does not include a nitrogen source that can be utilized by the microorganism for growth or culture propagation. A microorganism cultured in a nitrogen deplete medium experiences nitrogen starvation conditions.

The culture methods can include inducing expression of a particular gene described herein for the production of TAG, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the recombinant microorganisms or host cells can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use as food, microorganisms or host cells are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Microorganisms and host cells can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth. For TAG production, photosynthetic microorganisms or host cells can additionally or alternately be cultured in shake flasks, test tubes, vials, microtiter dishes, petri dishes, or the like, or combinations thereof.

Additionally or alternatively, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo) bioreactor do not constitute a dangerous and/or lethal dose with respect to the growth and/or survival of the microorganisms.

The methods include culturing a recombinant microorganism, such as a photosynthetic microorganism, such as, for example, an algae, that expresses a protein as described herein to produce TAG, in which the method results in production of at least 0.1%, at least 0.5%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 300%, at least 400%, at least 500%, at least 600%, at least 700%, at least 800%, at least 900%, or at least 1000% more than the amount of the TAG produced by an otherwise substantially identical microorganism not including the protein(s), cultured under identical conditions. Additionally or alternatively, the methods include producing at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, or at least 950 mg, per liter of culture of TAG by culturing the recombinant microorganisms described herein.

TAG can be recovered from culture by recovery means known to those of ordinary skill in the art, such as by whole culture extraction, for example, using organic solvents. In some cases, recovery of TAG can be enhanced by homogenization of the cells. For example, lipids such as TAG can be isolated from algae by extraction of the algae with a solvent at elevated temperature and/or pressure, as described in the co-pending, commonly-assigned U.S. patent application Ser. No. 13/407,817 entitled "Solvent Extraction of Products from Algae", filed on 29 Feb. 2012, which is incorporated herein by reference in its entirety. Further, when TAG is sufficiently released or secreted from the microorganisms into the culture medium, the recovery method can be adapted to recover efficiently only the released TAG, only the TAG produced and stored within the microorganisms, or both the produced and released TAG.

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Additionally or alternatively, the present invention can include one or more of the following embodiments.

EMBODIMENTS

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Embodiment 1

An isolated DNA molecule comprising a nucleotide sequence encoding a diacylglycerol acyltransferase that comprises an amino acid sequence selected from the group consisting of an amino acid sequence having at least 80% identity to SEQ ID NO:18; an amino acid sequence having at least 80% identity to SEQ ID NO:24; and an amino acid sequence having at least 80% identity to SEQ ID NO:36.

Embodiment 2

An isolated DNA molecule comprising a nucleotide sequence encoding a diacylglycerol acetyltransferase that comprises an amino acid sequence selected from the group consisting of an amino acid sequence having at least 80% identity to SEQ ID NO:82 and an amino acid sequence having at least 80% identity to SEQ ID NO:84.

Embodiment 3

An isolated DNA molecule comprising a nucleotide sequence encoding a localization peptide selected from the group consisting of an amino acid sequence having at least 80% identity to SEQ ID NO:74 or an amino acid sequence having at least 80% identity to SEQ ID NO:76.

Embodiment 4

An isolated DNA molecule according to Embodiment 3, wherein the nucleotide sequence encoding the localization polypeptide is operably linked to a nucleotide sequence encoding a glycerolphosphate acyltransferase (GPAT), a lysophosphatidic acid acyltransferase (LPAAT), a monoacylglycerol acyltransferase (MGAT), a diacylglycerol acyltransferase (DGAT), or a diacylglycerol acetyltransferase (DGAcT).

Embodiment 5

An expression cassette comprising a promoter operably linked to a DNA molecule according to Embodiment 1.

Embodiment 6

An expression cassette comprising a promoter operably linked to a DNA molecule according to Embodiment 2.

Embodiment 7

An expression cassette comprising a promoter operably linked to a DNA molecule according to Embodiment 3.

Embodiment 8

An expression cassette comprising a promoter operably linked to a DNA molecule according to Embodiment 3, wherein the DNA molecule of Embodiment 3 is operably linked to a heterologous protein encoding sequence.

Embodiment 9

The expression cassette of Embodiment 8, wherein the heterologous protein encoding sequence is a diacylglycerol acyltransferase encoding sequence.

Embodiment 10

A method of targeting an ectopically-expressed protein to an inner envelope surface of a chloroplast, the method comprising transfecting a chloroplast-containing cell with an expression vector comprising the expression cassette of Embodiment 8.

Embodiment 11

The method of Embodiment 10, wherein the ectopically-expressed protein is selected from the group consisting of a diacylglycerol acyltransferase (DGAT), a diacylglycerol acetyltransferase (DGAcT), a glycerolphosphate acyltransferase (GPAT), a lysophosphatidic acid acyltransferase (LPAAT), and a monoacylglycerol acyltransferase (MGAT).

Embodiment 12

The method of Embodiment 11, wherein the ectopically-expressed protein is a diacylglycerol acyltransferase.

Embodiment 13

A recombinant eukaryotic photosynthetic microorganism comprising a non-native gene encoding a DGAT, wherein the recombinant eukaryotic photosynthetic microorganism produces a greater amount of triglyceride than a control eukaryotic photosynthetic microorganism that is substantially identical to the recombinant photosynthetic eukaryotic microorganism in all respects except that the control eukaryotic photosynthetic microorganism lacks the gene encoding a DGAT.

Embodiment 14

The recombinant eukaryotic photosynthetic microorganism of Embodiment 13, wherein the recombinant eukaryotic photosynthetic microorganism produces a greater amount of triglyceride under nitrogen replete conditions in which inorganic carbon is substantially the sole source of carbon in the culture medium.

Embodiment 15

The recombinant eukaryotic photosynthetic microorganism of Embodiment 13, wherein the DGAT is a DGAT1, a DGAT2, a DGAT3, a WS/DGAT, or a DGAcT.

Embodiment 16

The recombinant eukaryotic photosynthetic microorganism of Embodiment 15, wherein the DGAT comprises a heterologous localization sequence that targets the DGAT to the chloroplast or endoplasmic reticulum.

Embodiment 17

A recombinant algal cell comprising a non-native gene encoding a diacylglycerol acyltransferase, wherein the diacylglycerol acyltransferase comprises an amino acid sequence having at least 80% identity to SEQ ID NO:4, SEQ ID NO:18, SEQ ID NO:24, SEQ ID NO:36, SEQ ID NO:40, SEQ ID NO:46, SEQ ID NO:56, SEQ ID NO:82; SEQ ID NO:84; and SEQ ID NO:86.

Embodiment 18

The recombinant eukaryotic photosynthetic microorganism of Embodiment 13, wherein the non-native gene encodes a diacylglycerol acyltransferase selected from the group consisting of an amino acid sequence having at least 80% identity to SEQ ID NO:18; an amino acid sequence having at least 80% identity to SEQ ID NO:24; and an amino acid sequence having at least 80% identity to SEQ ID NO:36.

Embodiment 19

The recombinant eukaryotic photosynthetic microorganism of Embodiment 13, wherein the recombinant eukaryotic photosynthetic microorganism is a recombinant algal cell of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

Embodiment 20

The recombinant algal cell of Embodiment 19, wherein the recombinant algal cell is a *Nannochloropsis* species.

Embodiment 21

The recombinant eukaryotic photosynthetic microorganism of Embodiment 13, wherein the recombinant eukaryotic photosynthetic microorganism produces a greater amount of triglyceride under nitrogen replete conditions than is produced by a control eukaryotic photosynthetic microorganism substantially identical to the recombinant eukaryotic photosynthetic microorganism in all respects and cultured under substantially the same conditions, except that the control eukaryotic photosynthetic microorganism does not include a non-native gene encoding a diacylglycerol acyltransferase.

Embodiment 22

The recombinant eukaryotic photosynthetic microorganism of Embodiment 21, wherein the recombinant eukaryotic photosynthetic microorganism produces a greater amount of triglyceride after one day of culturing under nitrogen replete conditions than is produced by a control eukaryotic photosynthetic microorganism substantially identical to the recombinant eukaryotic photosynthetic microorganism in all respects and cultured under substantially the same conditions, except that the control eukaryotic photosynthetic microorganism does not include a non-native gene encoding a diacylglycerol acyltransferase.

Embodiment 23

A method for producing a triglyceride in a recombinant eukaryotic photosynthetic microorganism, the method comprising culturing a recombinant eukaryotic photosynthetic microorganism according to Embodiment 13 under culture conditions such that diacylglycerol acyltransferase encoded by the non-native gene is expressed to produce a triglyceride.

Embodiment 24

The method of Embodiment 23, wherein the culture conditions are nitrogen replete.

Embodiment 25

The method of Embodiment 24, wherein the culture conditions are substantially or entirely photoautotrophic.

Embodiment 26

The method of Embodiment 23, wherein the recombinant eukaryotic photosynthetic microorganism produces a greater amount of triglyceride under nitrogen replete conditions than is produced by a control eukaryotic photosynthetic microorganism substantially identical to the recombinant eukaryotic photosynthetic microorganism in all respects and cultured under the substantially same conditions, except that the control eukaryotic photosynthetic microorganism does not include a non-native gene encoding a diacylglycerol acyltransferase.

Embodiment 27

The method of Embodiment 23, wherein the recombinant eukaryotic photosynthetic microorganism is a recombinant algal cell of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halo cafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

Embodiment 28

The method of Embodiment 27, wherein the recombinant algal cell is a *Nannochloropsis* cell.

Embodiment 29

The method of Embodiment 23, wherein the recombinant eukaryotic photosynthetic microorganism is proliferating and generating triglyceride at levels higher than the triglyceride levels generated by a non-transfected control microorganism-cultured under substantially the same conditions.

Embodiment 30

The method of Embodiment 29, wherein the recombinant eukaryotic photosynthetic microorganism generates triglyceride in nitrogen replete conditions at levels at least 70% greater in comparison to a non-transfected control microorganism.

Embodiment 31

The method of Embodiment 29, wherein the recombinant eukaryotic photosynthetic microorganism generates triglyceride in nitrogen replete conditions at levels at least two fold greater in comparison to a non-transfected control microorganism.

Embodiment 32

The method of Embodiment 23, wherein the non-native gene encodes a diacylglycerol acyltransferase having at least 80% identity to SEQ ID NO:18; or having at least 80% identity to SEQ ID NO:24; or having at least 80% identity to SEQ ID NO:36.

Embodiment 33

The method of Embodiment 23, wherein the non-native gene encodes a diacylglycerol acyltransferase having at least 80% identity to SEQ ID NO:4.

Embodiment 34

A method for producing triglyceride in an algal cell, the method comprising culturing an algal cell comprising the DNA molecule of Embodiment 9 under culture conditions such that DGAT is expressed.

Embodiment 35

The method of Embodiment 34, wherein the algal cell is a *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox*.

Embodiment 36

The method of Embodiment 35, wherein the algal cell is a *Nannochloropsis* cell.

Embodiment 37

The method of Embodiment 34, wherein the culture conditions are nitrogen replete.

Embodiment 38

The method of Embodiment 37, wherein the culture conditions are substantially or entirely photoautotrophic.

Embodiment 39

The method of Embodiment 34, wherein the algal cell proliferates and generates triglyceride at levels higher in comparison to a non-transfected control cell under the culture conditions.

Embodiment 40

The method of Embodiment 39, wherein the algal cell generates triglyceride in nitrogen replete conditions at levels at least two fold greater in comparison to a non-transfected control cell.

EXAMPLES

The invention as described above can be readily understood by reference to the following examples, which are included for purposes of illustration of certain aspects and embodiments of the present invention, and are not intended to limit the invention.

Example 1

Construction of a Vector Containing MmDGAT2Δ55 Under Control of SV40 Promoter

The type 2 DGAT ("DGAT2") from *Mus musculus* (Accession no. NP_080660; SEQ ID NO:2) is an endoplasmic-reticulum and oil-body associated enzyme responsible for the majority of synthesis of triglyceride (TAG) in cytosolic oil bodies (Stone et al. (2009) *J. Biol Chem* 284(8): 5352-5361). The knock-out of this gene in *M. musculus* leads to a lethal phenotype, whereas the type 1 DGAT ("DGAT1") is dispensable (Yen et al. (2008) *J. Lipid Res.* 49: 2283-2301). A *Nannochloropsis*-codon-optimized gene was synthesized (DNA 2.0, Menlo Park, Calif.) (SEQ ID NO:3) encoding a truncated version of the *M. musculus* DGAT2 lacking the N-terminal 55 amino acids (MmDGAT2Δ55; SEQ ID NO:4). These N-terminal amino acids were hypothesized to encode a mitochondrial localization sequence (Stone et al., 2009) which may be expendable for expression of the enzyme in *Nannochloropsis*. PCR primers MsDGAT2 F2 (SEQ ID NO:13) and MsDGAT2 R1 (SEQ ID NO:14) were used to amplify a truncated variant of MmDGAT2 in which the first 55 amino acids encoding an ER and mitochondrial targeting sequence were omitted. The truncated MmDGAT2Δ55 gene (SEQ ID NO:3), was cloned into a vector designed for replication and selection in *E. coli* (pUC origin, kanamycin resistance) that included the bleomycin resistance gene (ble) (SEQ ID NO:5; protein sequence SEQ ID NO:6) linked to the GAPDH promoter from *Phaeodactylum tricornutum* (SEQ ID NO:7) and an alpha tubulin gene terminator from *Thalassiosira pseudonana* (SEQ ID NO:8). The vector also included the SV40 promoter (SEQ ID NO:9), followed by a chimeric intron (SEQ ID NO:10), which was followed by the MmDGAT2Δ55 gene (SEQ ID NO:3), which was followed by a SV40 polyA region (SEQ ID NO:11), and then an SV40 late enhancer (SEQ ID NO:12). The MmDGATΔ55 expression vector is depicted in FIG. 1.

PCR amplifications were performed with the Phusion polymerase (NEB) and gel-purified (Zymoclean Gel DNA Recovery Kit, Zymo Research) after confirmation on 1% agarose (ReadyAgarose Gel, TAE, BioRad). Primers were synthesized by Integrated DNA Technologies, Inc. Plasmid isolations were done with the QIAprep Spin Miniprep Kit (Qiagen). *E. coli* transformations used either TOP10 or Mach1 competent cells (Invitrogen) and transformed cells were grown on LB+chloramphenicol (50 µg/mL), LB+kanamycin (50 µg/mL), or LB+carbenicillin (100 ng/µL) as appropriate.

Example 2

Transformation of *Nannochloropsis* with GL729 MmDGAT2 Constructs and PCR Screening of Transformants Media used for the growth of *Nannochloropsis* included the following:

PM023:

35 g/L Instant Ocean Salts (Aquatic Eco Systems, Apopka, Fla.), 7.1 mM $NH_4Cl$, 0.32 mM $NaH_2PO_4$, 10 mM MOPS pH 8.0, 1× Guillard's F/2 trace metals solution (Final concentration in medium: 11.65 nM Ferric chloride.$6H_2O$; 11.7 nM Disodium EDTA.$2H_2O$; 39.3 nM Cupric sulfate.$5H_2O$, 26 nM Sodium molybdate.2H$_2$O, 76.5 nM Zinc Sulfate.7H$_2$O, 42 nM Cobalt chloride.6H$_2$O, 910 nM Manganese Chloride.4H$_2$O).

PM027:

PM023 media, omitting NH$_4$Cl.

PM010:

35 g/L Instant Ocean Salts, 1× Guillard's F/2 marine water enrichment solution (from 50× stock from Sigma-Aldrich, St. Louis, Mo., cat. No. G0154; final concentrations of components in media: 882.5 nM Sodium nitrate; 32 µM Sodium phosphate monobasic; 20.5 nM Biotin; 42 nM Cobalt chloride.6H$_2$O; 40 nM Cupric sulfate.5H$_2$O; 11.65 nM Ferric chloride.6H$_2$O; 11.713 nM Disodium EDTA.2H$_2$O; 909.5 nM Manganese chloride.4H$_2$O; 24.8 nM Sodium molybdate.2H$_2$O; 296.5 nM Thiamine.HCl; 3.7 nM Vitamin B$_{12}$; 76.5 nM Zinc sulfate.7H$_2$O).

PM024:

35 g/L Instant Ocean Salts, 10× Guillard's F/2 marine water enrichment solution (from 50× stock from Sigma-Aldrich, St. Louis, Mo., cat. No. G0154; final concentrations of components in media: 8.825 mM Sodium nitrate; 320 µM Sodium phosphate monobasic; 205 nM biotin; 420 nM Cobalt chloride.6H$_2$O; 400 nM Cupric sulfate.5H$_2$O; 116.5 nM Ferric chloride.6H$_2$O; 117.13 nM Disodium EDTA.2H$_2$O; 9.095 µM Manganese chloride.4H$_2$O; 248 nM Sodium molybdate.2H$_2$O; 2.965 µM Thiamine.HIC1; 37 nM Vitamin B$_{12}$; 765 nM Zinc sulfate.7H$_2$O).

PM064:

35 g/L Instant Ocean Salts, 5× Guillard's F/2 marine water enrichment solution (from 50× stock from Sigma-Aldrich, St. Louis, Mo., cat. No. G0154; final concentrations of components in media: 4.412 mM Sodium nitrate; 16 µM Sodium phosphate monobasic; 102.5 nM Biotin; 210 nM Cobalt chloride.6H$_2$O; 200 nM Cupric sulfate.5H$_2$O; 58.25 µM Ferric chloride.6H$_2$O; 58.5 µM Disodium EDTA.2H$_2$O; 4.54 µM Manganese chloride.4H$_2$O; 124 nM Sodium molybdate.2H$_2$O; 1.48 µM Thiamine.HIC1; 18.5 nM Vitamin B$_{12}$; 382 nM Zinc sulfate.7H$_2$O).

All transformants were grown in the presence of Zeocin (5 µg/mL) unless noted otherwise.

The pGLR003 vector construct (FIG. 1) containing a ble selectable marker and the MmDGAT2Δ55 gene under the control of the SV40 promoter was linearized and introduced by electroporation into a *Nannochloropsis gaditana* wild-type strain obtained from the Center for Culture of Marine Phytoplankton (CCMP, catalog number 1894). Briefly, two 2 L shake flasks that each included a 500 mL volume of *N. gaditiana* culture were grown to a cell density of $0.9 \times 10^7$ cells/mL. The cells were centrifuged for 10 min. at 25° C. and 2500×g. They were resuspended in 385 mM sorbitol to a concentration of $1.1 \times 10^{10}$ cells/mL. Approximately 500 ng of linearized DNA was mixed into 100 µL of cell suspension and transferred to a 2 mm gap cuvette (BioRad). Electroporation was performed on a BioRad GenePulser set to 50 µF capacitance, 500 ohms resistance, and 2.2 kV. Immediately after the electroporation, 1 mL of 385 mM sorbitol was gently mixed into the transformed cell suspension and the cells were allowed to sit at room temperature for a few minutes. The cell mixture was then transferred to 10 mL of PM024 liquid media and allowed to recover overnight at room temperature at 25° C. in dim light (5 µE m$^{-2}$ s$^{-1}$). The cell mixture was then centrifuged at 2500×g at 25° C. for 10 minutes, decanted, and resuspended in PM024 to a final volume of approximately 600 µL. Resuspended cells (300 µL) were spread using sterile 4 mm glass beads onto PM024 plates containing 5 µg/mL zeocin to select for transformants. Colonies were observed after 24 days of selection.

Three colonies were picked to test for the presence of the MmDGAT2Δ55 gene. The colonies were patched onto fresh PM24+ zeocin plates and cultured in liquid media under selection, and gDNA was prepared from the three transgenic clones as well as the wild-type. The presence of a DNA fragment containing MmDGAT2Δ55 was verified using PCR with transgenic cells as the template. PCR genotyping was done using the primers MsDGAT2 geno F1 (SEQ ID NO:15) and MsDGAT2 geno R1 (SEQ ID NO:16) and the following thermocycler conditions: 94° C. for 5 minutes; 30 cycles of: 94° C. for 30 seconds, 60° C. for 30 seconds, 72° C. for 15 seconds; followed by 72° C. for 5 minutes, then a 4° C. hold. A 488 by fragment could be amplified from all three clones selected for PCR testing (designated 3A#1, 3A#2, and 4A#1), but did not occur as a PCR product in the reaction using wild-type (nontranformed) cells.

Example 3

TAG Production by *Nannochloropsis* Transformants

To determine the effect of the MmDGAT2 transgene on TAG production, the clones were grown in 30 mL cultures in 250 mL shake flasks under 40-50 µE m$^{-2}$ s$^{-1}$ shaking at 115 rpm and 25° C. in the presence of ambient 1% CO$_2$. The cells were grown in nitrogen-replete media (PM064), a condition that does not normally lead to TAG production during the exponential growth phase. 5 mL of the inoculation cultures were sampled and submitted for TAG analysis as timepoint t−1. Cultures were then seeded in triplicate at $0.2 \times 10^7$ cells/mL. After 3 days (t1), 10 mL aliquots of each culture were removed, centrifuged briefly, and resuspended in water for a total volume of approximately 500 µL for TAG analysis. The remaining cultures were diluted to approximately $0.1 \times 10^7$ cells/mL so that the cells remained in exponential growth phase. 10 mL of each culture was sampled again at day 7 (t2) in the same manner.

To determine TAG content of the cells, neutral lipids were extracted with hexane and analyzed by HPLC. Briefly, for each sample (three cultures were analyzed for each transformant), 5 mLs of culture was centrifuged for 10 min at 4750 rpm. The supernatant was decanted, and 0.4 mL of water was added to the pellet to provide a cell suspension of approximately 0.5 mL. The cell suspension was transferred to a 4 mL glass vial which had a Teflon lined cap. Glass beads (212-300 µM, 0.5 mL) were added to each of the cell suspensions, after which 50 µL of 50% H$_2$SO$_4$ and 100 µL of 5M NaCl were added. Bead beating was performed for 5 min at 1000 rpm, then 2 mL of hexane was added to each sample, and bead beating was repeated for 5 min at 1000 rpm. The samples were loaded onto a multi-tube vortexer and shaken for 30 min at 1000 rpm, and then vortexed for 30 sec at 2500 rpm. 0.5 mL of the organic layer was transferred to an HPLC vial, and 50 µL of internal standard solution (1 mg/mL 6-ketocholestanol in toluene) was added to each vial. Standards were from NuCheck, Sigma-Aldrich, or Supelco. The vials were capped and vortexed briefly (5 sec at 2500 rpm) prior to HPLC analysis. The HPLC was run at a flow rate of 2 mL/min on a Chromegasphere SI-60 150 mm×4.6 mm, 10 µm column (ES Industries), with a column compartment set at 40° C. The injection volume was 25 µL with a draw and eject speed of 200 µL/min. Eluent A was hexane and Eluent B was a 80:10:10:1 mixture of hexane, isopropanol, ethyl acetate, and 10% formic acid in isopropanaol, run as a gradient program as follows: 2% B at 0.0 min; 2% B at 1.0 min; 35% B at 8.0 min; 98% B at 8.5 min; 98% B at 11.5 min; 2% B at 11.6 min; stop time: 11.6 min; 5 min post time. The detector was ELSD at 30° C. and 3.5 bar $N_2$, with a gain of 5.

The productivity of the inoculation cultures is provided in Table 1, which demonstrates that the transgenic isolates produced between 17 and 28 micrograms per mL of TAG during the cultivation period, while under the nitrogen-replete growth conditions, whereas nontransformed *N. gaditiana* cells ("wt neg. control") did not produce detectable TAG. This was the first observation of differential TAG accumulation between the transgenic algae and nontransformed wild-type.

TABLE 1

TAG production by algal transformants and nontransformed wild type control

| Sample ID | TAG (µg/mL) | cells/mL |
|---|---|---|
| GL729-03A#1 t-1 | 27.6 | 2.78E+07 |
| GL729-03A#2 t-1 | 21.6 | 1.94E+07 |
| GL729-04A#1 t-1 | 17.2 | 1.38E+07 |
| wt neg. control t-1 | 0.0 | 1.41E+07 |

Figure 2:
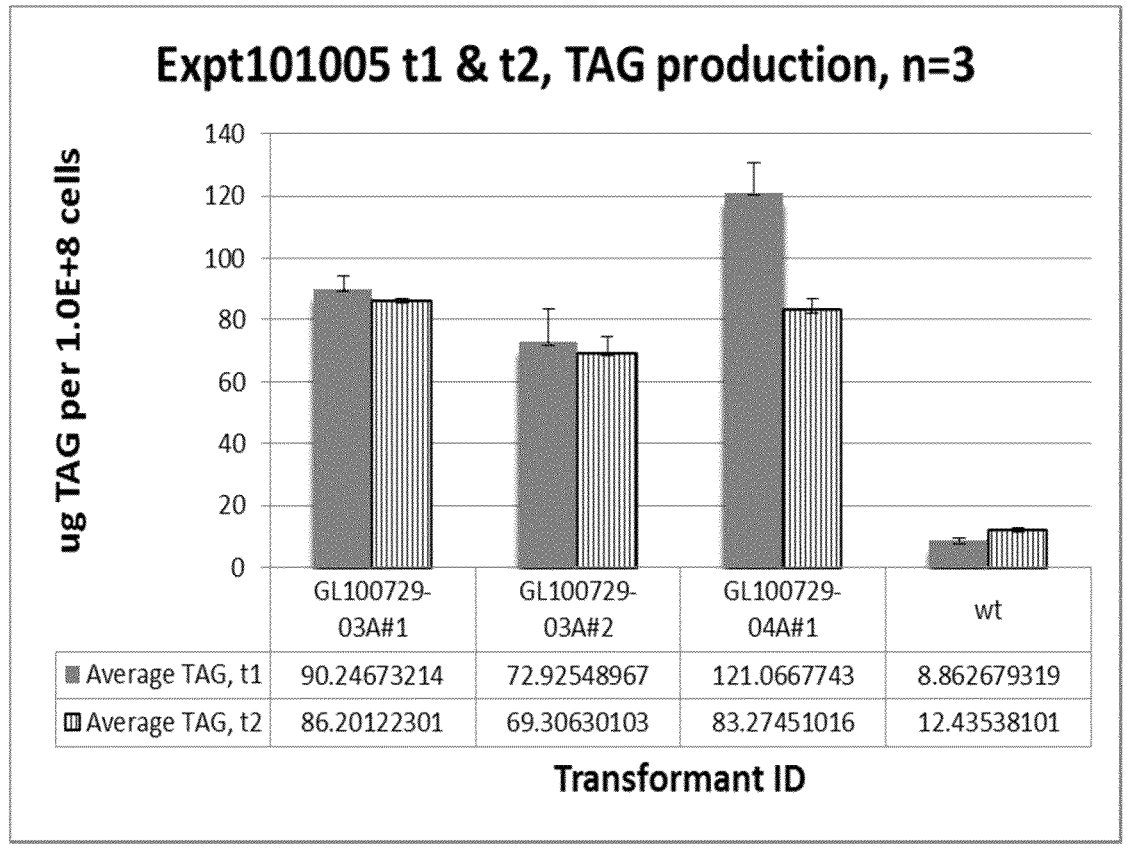
FIG. 2 is a graphical representation of the results from a controlled test for constitutive expression of the MmDGAT2Δ55gene. TAG accumulation in triplicate cultures in nitrogen-replete media was sampled during the exponential growth phase. The levels of TAG detected in the experimental transgenic strains at both t1 (day 3) and t2 (day 7) show significant increase in μg of TAG per cell compared to nontransformed wild-type control.

These results were observed again at days 3 and 7 of the shake flask cultures. As seen in FIG. 2 and Table 2, the levels of TAG detected in the experimental transgenic strains at both t1 (day 3) and t2 (day 7) show a very significant increase in µg TAG per cell with respect to wild type, during a time frame in which the cells were increasing in number.

TABLE 2

Propagation of transformed and nontransformed (wt) algae in production cultures

| Strain ID | Average cells/mL, t1 | Average cells/mL, t2 |
|---|---|---|
| GL100729-03A#1 | 2.97E+06 | 5.34E+06 |
| GL100729-03A#2 | 2.79E+06 | 5.03E+06 |
| GL100729-04A#1 | 4.03E+06 | 9.57E+06 |
| wild type control | 1.05E+07 | 7.84E+06 |

Example 4

TAG Accumulation in Nitrogen-Deprived MmDGAT2Δ55 Isolates

Figure 3:
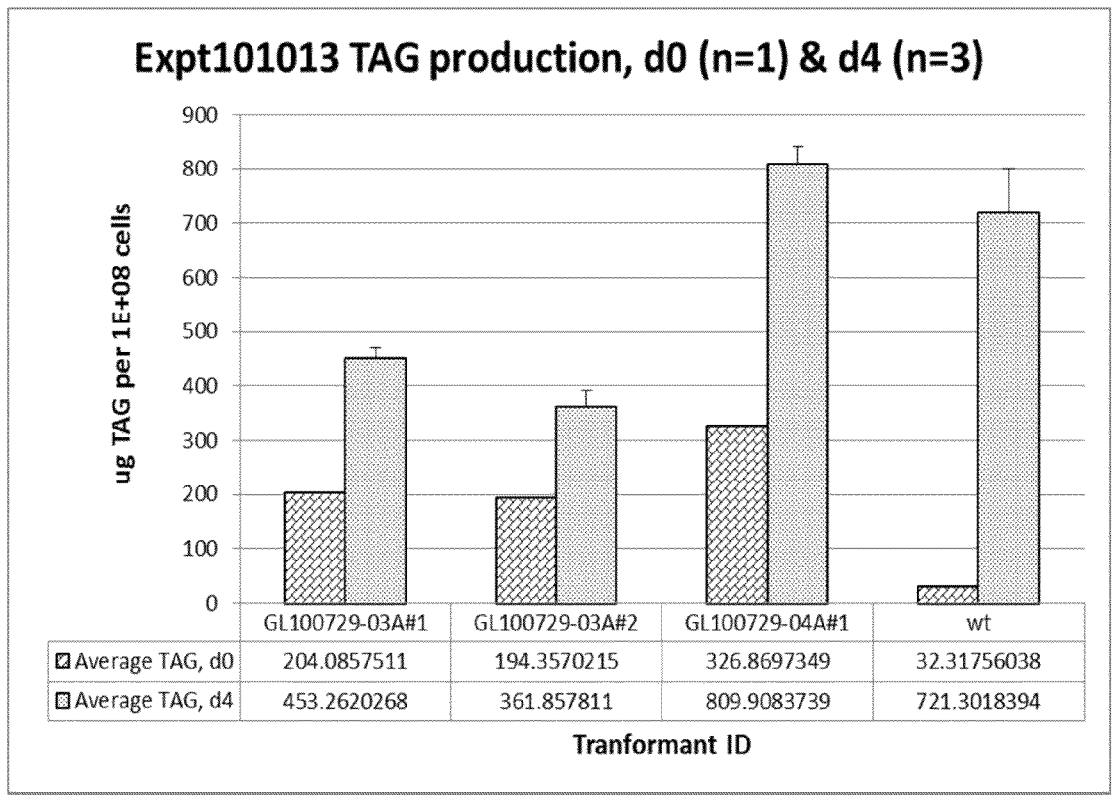
FIG. 3 is also a graphical representation of the results from a controlled test for constitutive expression of the MmDGAT2Δ55gene. TAG accumulation was sampled in triplicate cultures in nitrogen-minus media (PM27) during the exponential growth phase. At day zero levels of TAG detected in the experimental transgenic strains showed significantly higher levels of TAG per cell compared to wild-type and the GL100729-04A#1 transformant produced TAG at a level at least as high as that of wild-type cells four days after the onset of nitrogen deprivation.

TAG accumulation in the transgenic isolates was also measured after growth of the cultures in nitrogen-minus media when TAG synthesis is normally induced in wild type *Nannochloropsis*. Triplicate samples of each transformant were cultured in PM027 N-minus media as 20 mL cultures in 250 mL shake flasks at 80-100 µE $m^{-2} s^{-1}$, 25° C., and 1% ambient $CO_2$, with shaking at 115 rpm. At day zero, cells were centrifuged and transferred from N+(PM023) to N−(PM027) media. Immediately after transfer of the strains from nitrogen-replete to nitrogen-free media, the levels of TAG detected in the experimental transgenic strains again showed significantly higher levels of TAG per cell as compared to wild type (FIG. 3). The wild type at d0 in this experiment was observed to have a higher level of TAG as compared to the levels found in the nitrogen-replete conditions (FIG. 2). This may be due to the increase in irradiance as higher light intensity has been shown to increase lipid accumulation, perhaps due to light stress. After four days in nitrogen-free media, however, the wild type TAG levels increased dramatically and were approximately 2-fold higher than the TAG levels of the transformants GL100729-03A#1 and GL100729-03A#2. The GL100729-04A#1 transformants however produced TAG at a level at least as high as that of wild type cells four days after the onset of nitrogen deprivation (FIG. 3).

Example 5

Growth of MmDGAT2Δ55 Transformants in Nitrogen-Replete Media

Figure 4:
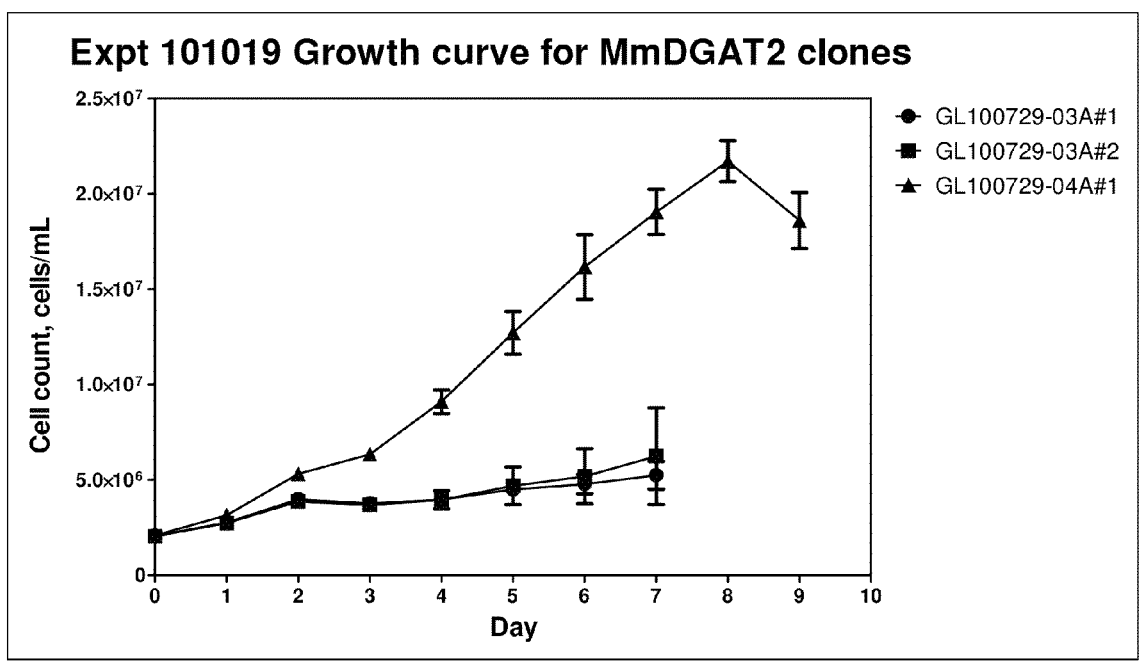
FIG. 4 is a graphical representation of growth curves generated to confirm that cell cultures were sampled during exponential growth phase in FIG. 2 above. Although GL100729-04A#1 was in log phase when sampled for FIG. 4, the other two clones may have been in linear phase at that time. Cultures for 03A#1 and 03A#2 were aborted at day 7.
Figure 5:
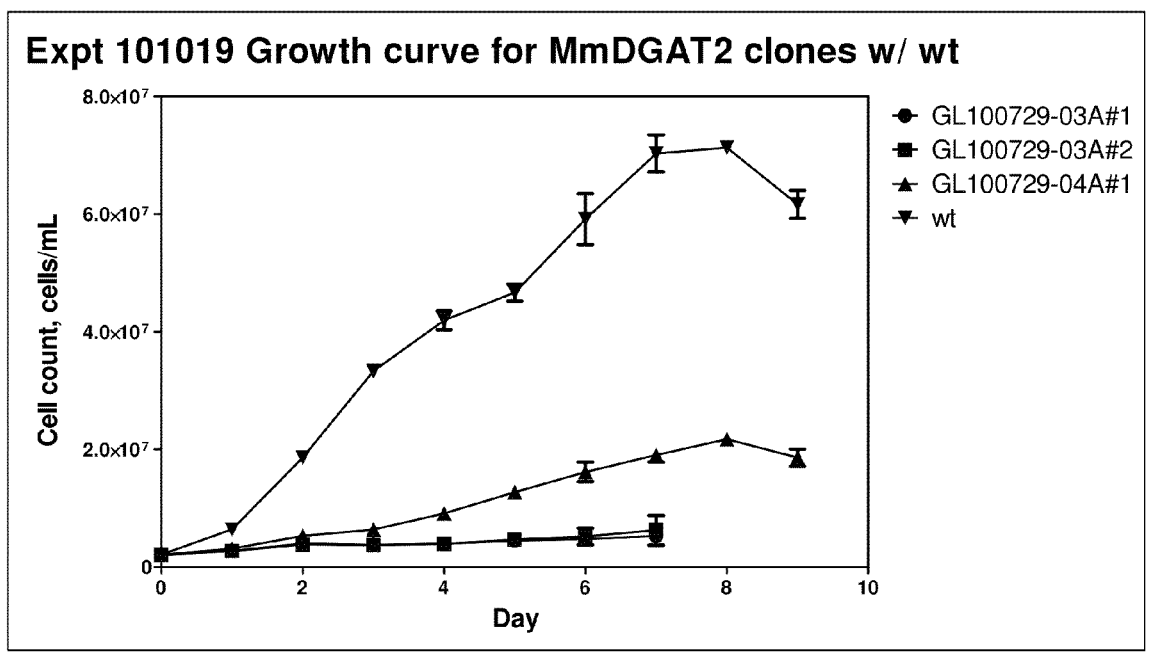
FIG. 5 is a graphical representation providing the same data as FIG. 4 above but with the addition of the growth curve for wild-type alongside the MmDGAT2Δ55 clones for comparison. Growth conditions were the same for all cultures except media for the wild-type cultures did not contain Zeocin because the wild-type strain is not Zeocin resistant.

To confirm that cell cultures were indeed sampled during the exponential growth phase in the experiment of Example 3 (FIG. 2), triplicate cultures were again grown at 80-100 µE/m2/s, 25° C., 1% ambient $CO_2$, with shaking at 115 rpm. Cell counts of samples grown in nitrogen-replete media (35 g/L Instant Ocean, 1× Guillard's F/2 marine water enrichment solution (Sigma, cat. No. G0154)) were taken daily. FIG. 4 demonstrates that GL729-04A#1 continues to divide through eight days of culture growth, whereas the other two DGAT-2 transformants, GL729-03A#1 and GL729-03A#2 do not show significant growth after the second day in culture (cultures for 03A#1 and 03A#2 were aborted at day 7). The graph provided in FIG. 5 provides the same data of the transformant cultures grown in nitrogen-replete media as is shown in the graph of FIG. 4, but also includes the growth curve for wild type cells alongside the MmDGAT2 transformants for comparison. Growth conditions were the same for all cultures, except that the media for the wild type cultures did not contain zeocin since the wild type strain is not zeocin resistant.

Cell samples were taken on day 1 of the growth experiment, stained with 2 µM BODIPY 505/515 at room temperature, and observed under the microscope. GL729-03A#1, 03A#2, and 04A#1 all showed more lipid body staining than wild type cells. In addition, cell size was measured using a Coulter Counter. GL729-04A#1, the high lipid producer, was found to have a markedly larger mean cell diameter than wild type, 4.1 micron versus 3.5 micron, respectively. The other two transgenic clones had very similar cell diameters to wild-type.

Example 6

Cloning of MmDGAT2Δ55 and *Nannochloropsis gaditana* DGATs

Figure 6:
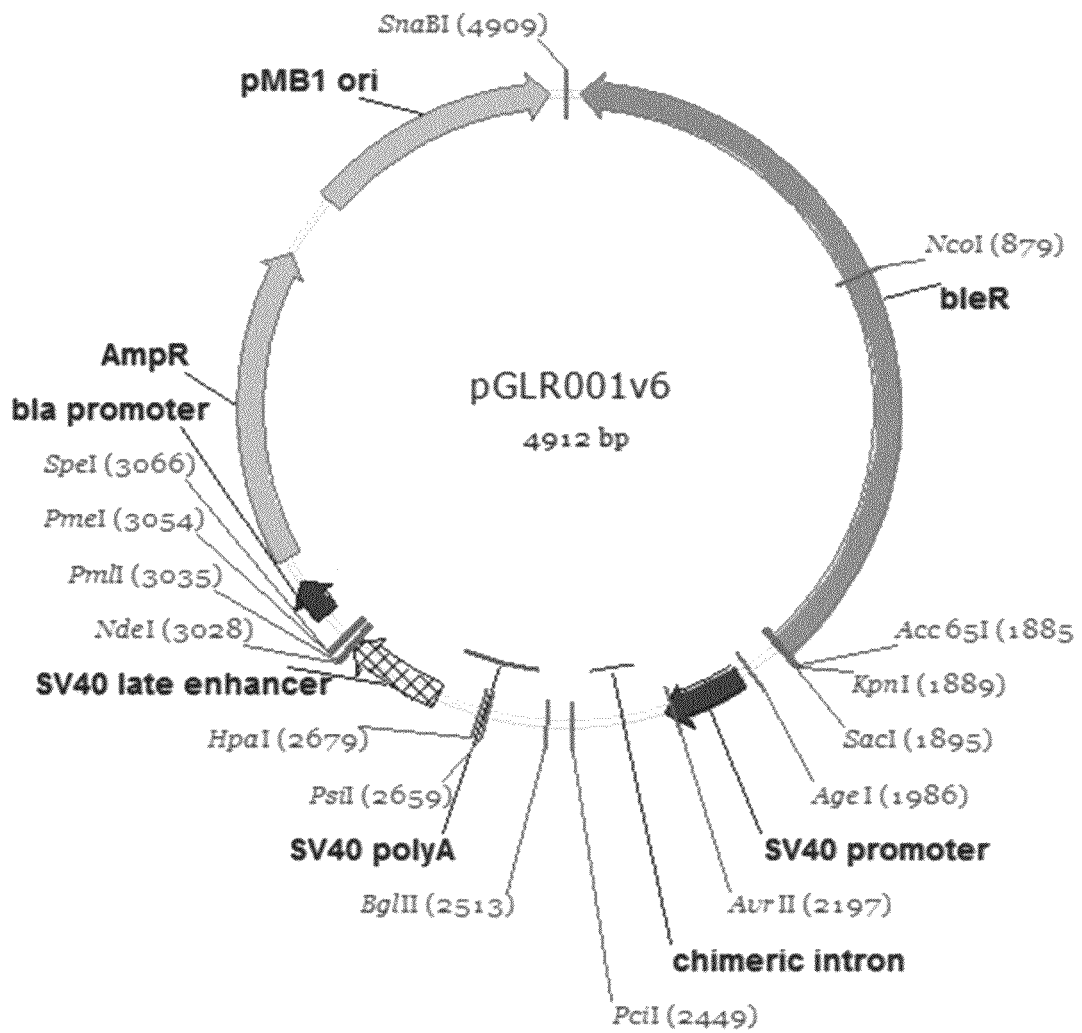
FIG. 6 is a plasmid map of the expression/shuttle vector pGLR001v6. Vector pGLR001 was generated for cloning of DGAT genes from *Nannochloropsis* and *Mus musculus*.

Vector pGLR001 was generated for cloning of DGAT genes from *Nannochloropsis gaditana* as well as *Mus musculus*. A map of this vector is provided in FIG. 6. The bleomycin resistance gene (ble) (SEQ ID NO:5; protein sequence SEQ ID NO:6) in this vector was positioned downstream of the GAPDH promoter from *Phaeodactylum tricornutum*

(SEQ ID NO:7) and upstream of alpha tubulin gene terminator from *Thalassiosira pseudonana* (SEQ ID NO:8).

The *N. gaditana* DGAT2 gene "Ng7DGAT" (SEQ ID NO:17) encoding a type 2 DGAT (SEQ ID NO:18) was cloned from cDNA. First strand cDNA synthesis using a 45° C. reaction temperature was performed on wild-type *N. gaditana* RNA according to the manufacturer's protocol (First Strand cDNA Synthesis Kit, Fermentas). The Ng7DGAT gene was amplified by PCR using primers 7DGAT F1 (SEQ ID NO:19) and 7DGAT R1 (SEQ ID NO:20) based on the *Nannochloropsis* genome sequence and subcloned into the pCR4 vector (Invitrogen) for sequencing. The gene was then amplified using 7DGAT F2 (SEQ ID NO:21) and 7DGAT R2 (SEQ ID NO:22) and cloned into the *Nannochloropsis* expression vector pGLR001 (FIG. 6) which had been double digested with PciI and BglII. The final construct GLR826-02#1 was linearized with PvuI and phenol-chloroform purified prior to transformation.

Attempts to clone the Ng2DGAT gene (SEQ ID NO:23) encoding another type 2 DGAT of *Nannochloropsis* (SEQ ID NO:24) using the above first strand cDNA were unsuccessful, so double stranded cDNA was generated using the same template RNA and the InFusion SMARTer Directional cDNA Library Construction Kit (Clontech) according to the manufacturer's protocol. The Ng2DGAT gene was amplified by PCR using primers 2DGAT F1 (SEQ ID NO:25) and 2DGAT R1 (SEQ ID NO:26) and subcloned into the pCR4 vector (Invitrogen) for sequencing. The gene was then amplified using 2DGAT F2 (SEQ ID NO:27) and 2DGAT R2 (SEQ ID NO:28) and cloned into the *Nannochloropsis* expression vector pGLR001 (FIG. 6) which had been double digested with PciI and BglII. The final construct GL903-04#4 was linearized with PvuI and phenol-chloroform purified prior to wild-type *N. gaditana* transformation.

The linearized constructs for "ER+MmDGAT2Δ55" (SEQ ID NO:85, encoding the ER+MmDGAT2Δ55 polypeptide of SEQ ID NO:86) that included a sequence encoding the *P. tricornutum* Bip ER targeting signal (Apt, 2002; SEQ ID NO:29; peptide sequence provided as SEQ ID NO:30) upstream of the *Nannochloropsis*-codon-optimized MmDGAT2Δ55 coding sequence (SEQ ID NO:3), as well as the constructs for MmDGAT2Δ55, Ng2DGAT, and Ng7DGAT, were transformed into wild-type *Nannochloropsis* as described. Colonies were genotyped by PCR using the primers MsDGAT2genoF1 (SEQ ID NO:15) and MsDGAT2genoR1 (SEQ ID NO:16); 2DGATgenoF2 (SEQ ID NO:31) and 2DGATgenoR2 (SEQ ID NO:32); and 7DGATgenoF2 (SEQ ID NO:33) and 7DGATgenoR2 (SEQ ID NO:34); respectively.

TABLE 3

Primers for cloning mouse and *Nannochloropsis* DGAT genes

| Primer name | Primer sequence |
| --- | --- |
| MsDGAT2 F2 | 5'-CAAGCTTGCCGCCAACATGGTGACGTGGCTCAACC-3' (SEQ ID NO: 13) |
| MsDGAT2 R1 | 5'-GCCCCGACTCTAGAAGATCTTTATTACAACTCGTCGTCGTTGAC-3' (SEQ ID NO: 14) |
| MsDGAT2 geno F1 | 5'-CCCGGAACTACATCTTTGGCTAC-3' (SEQ ID NO: 15) |
| MsDGAT2 geno R1 | 5'-GTGGAAAATGCAGGGAGCGAAC-3' (SEQ ID NO: 16) |
| 7DGAT F1 | 5'-ATGGTGCTTGGGGAGGGCAAA-3' (SEQ ID NO: 19) |
| 7DGAT R1 | 5'-CTTCAAAACAGATGCAGCTCC-3' (SEQ ID NO: 20) |
| 7DGAT F2 | 5'-CAAGCTTGCCGCCAACATGGTGCTTGGGGAGGGCAAA-3' (SEQ ID NO: 21) |
| 7DGAT R2 | 5'-GCCCCGACTCTAGAAGATCTCTTCAAAACAGATGCAGCTCC-3' (SEQ ID NO: 22) |
| 2DGAT F1 | 5'-ATGACTGCCTTCTTTCGGCGTAG-3' (SEQ ID NO: 25) |
| 2DGAT R1 | 5'-TCACGAAATCGCCACGAACTCTTC-3' (SEQ ID NO: 26) |
| 2DGAT F2 | 5'-CAAGCTTGCCGCCAACATGACTGCCTTCTTTCGGCGTAG-3' (SEQ ID NO: 27) |
| 2DGAT R2 | 5'-GCCCCGACTCTAGAAGATCTTCACGAAATCGCCACGAACTCTTC-3' (SEQ ID NO: 28) |
| 2DGAT geno F2 | 5'-GGGAGTCGACCTGCCTTG-3' (SEQ ID NO: 31) |
| 2DGAT geno R2 | 5'-GAAGACGAGAGAGTAAAAGACTTGGATG-3' (SEQ ID NO: 32) |
| 7DGAT geno F2 | 5'-CATGGGATCATGCCGCACTC-3' (SEQ ID NO: 33) |
| 7DGAT geno R2 | 5'-CAAATACCCCAGGGCGATAGTATAG-3' (SEQ ID NO: 34) |

Ten clones from each transformation were genotyped. A 488 bp fragment corresponding to the MmDGAT2 gene was amplified from all 10 clones of 110-01 and 110-02. For both Ng2DGAT and Ng7DGAT, genotyping primers were designed within two distinct exons so that they would amplify across an exon in genomic DNA. In clones containing the transgene, both the fragment from the genomic DNA and a shorter band from the construct based on the cDNA should be present. For 110-13, 2 bands were observed for all clones except #3. Two bands were amplified from all 10 clones tested for 114, indicating the presence of both the transgene and the endogenous DGAT.

Six unique clones were inoculated for 114-13 (Ng2DGAT) and 7 unique clones each for 101014-01 (ER+ MmDGAT2Δ55), −02 (MmDGAT2Δ55), and −14 (Ng7DGAT) and were tested alongside triplicate wild-type samples and duplicate samples of GL729-04A#1 (MmDGAT2Δ55). 30 mL cultures were grown in 250 mL shake flasks with nitrogen-replete media (35 g/L Instant Ocean, 5× Sigma Guillard's F/2 marine water enrichment solution (Sigma, cat. No. G0154) under 80 µE m$^{-2}$ s$^{-1}$ shaking at 115 rpm and 25° C. in the presence of ambient 1% $CO_2$. After 2 days, the cells were harvested and analyzed for triglyceride content as provided above, except that the gradient program was as follows: 0.0 min, 2% B; 1.0 min, 2%; 5.0 min, 25%; 5.5 min 98%; 8.99 min, 98%; 9 min, 2%; stop time: 9 min; post time, 4 min.

Figure 7:
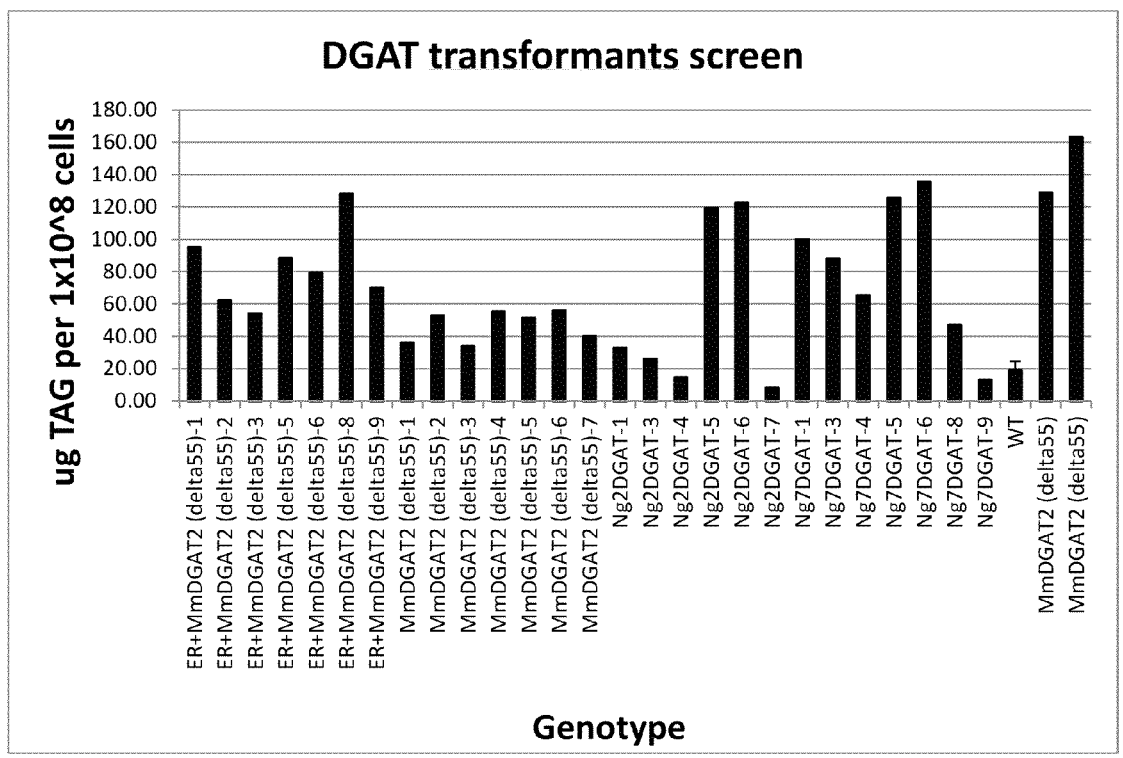
FIG. 7 is a graphical representation of TAG accumulation per $1 \times 10^8$ cells for each transformant screened in Example 6 herein.

Although the clones displayed wide variability in TAG productivity (FIG. 7), the majority of the clones produced more TAG than did wild-type *N. gaditana* (shown third from the right), and some of the clones produced at least five-fold the amount of TAG produced by wild-type cells after two days of culture in nitrogen replete media.

Example 7

Cloning of Algal and Microbial DGAT Genes

Microbial DGAT genes listed in Table 4 (below) were synthesized by DNA 2.0 or Genewiz except for the *Marinobacter hydrocarbonoclasticus* WS1 "FF" gene which was PCR amplified from metagenomic DNA extracted from a water sample taken from a pond at Pacific Aquafarms located north of the Salton Sea in southern California. DGAT genes were sub-cloned into *Nannochloropsis* shuttle vector GLR001 (FIG. 6) and the yeast shuttle vector p416TEF (Mumberg et al. (1995) Gene 156: 119-122). *Nannochloropsis* DGAT2 genes Ng2DGAT (SEQ ID NO:23), Ng7DGAT (SEQ ID NO:17), and Ng10DGAT (SEQ ID NO:35) were PCR amplified from *N. gaditana* cDNA and cloned into the p416TEF vector first and then sub-cloned into *Nannochloropsis* shuttle vector GLR001. All microbial and *Nannochloropsis* DGATs were sub-cloned/cloned (using the BPS cloning kit) in *E. coli* and selected for on 100 µg/mL carbenicillin LB agar plates. Positive clones were screened using colony PCR and inoculated in 3 mL LB 100 µg/mL carbenicillin and grown at 37° C. overnight and were plasmid prepped. Plasmids were electroporated into yeast strains and selected for on uracil drop-out agar plates.

TABLE 4

Primers used for cloning microbial and *Nannochloropsis* DGAT genes

| Gene name | Primer sequences ** |
|---|---|
| *Alcanivorax borkumensis* DGAT YP_694462.1 (SEQ ID NO: 40) | "Ab_AtfA1_GLR001_PciI_F" AGCGGCCGCAAGCTTGCCGCCAATGAAAGCCTTAAGTCCAGTGG (SEQ ID NO: 37) "Ab_AtfA1_GLR001_PciI_R" GACCGACGTACCTCTGAGTGACATGCTATTTGATCCCAGCTCCAAT C (SEQ ID NO: 38) |
| *Marinobacter Hydrocarbonclasticus* WS1 "FF" (SEQ ID NO: 46) | "Mh_WS1_GLR001_PciI_F" AGCGGCCGCAAGCTTGCCGCCAATGACGCCCCTGAATCCCACTGA C (SEQ ID NO: 41) "Mh_WS1_GLR001_PciI_R" GACCGACGTACCTCTGAGTGACATGTTACAGACCGGCGTTGAGCTC C (SEQ ID NO: 42) "WS1_416TEF_F" TCTAATCTAAGTTTTCTAGAACTAGTGGATCCCCCGCCACCATGAC GCCCCTGAATCCCACTGAC (SEQ ID NO: 43) "WS1_416TEF" GAGGTCGACGGTATCGATAAGCTTGATATCGAATTCCTGCAGCCCT TACTATTACAGACCGGCGTTGAGCTCC (SEQ ID NO: 44) |
| *Mycobacterium smegmatis* WS/DGAT AB K74273.1 (SEQ ID NO: 50) | "Ms_WS_DGAT_GLR001_PciI_F" AGCGGCCGCAAGCTTGCCGCCAATGAACCGCATGCAACTC (SEQ ID NO: 47) "Ms_WS_DGAT_GLR001_PciI_R" GACCGACGTACCTCTGAGTGACATGTTAAGCGCCAGTGGCGGTTTC (SEQ ID NO: 48) |
| *Rhodococcus opacus* Atf1 GQ923886.1 (SEQ ID NO: 56) | "Ro_Atf1_416TEF_F" TCTAATCTAAGTTTTCTAGAACTAGTGGATCCCCCGCCACCATGAC CCAGACGGACTTCATGTCG (SEQ ID NO: 51) "Ro_Atf1_416TEF_R" GAGGTCGACGGTATCGATAAGCTTGATATCGAATTCCTGCAGCCCT TACTATCACGAGGCCACGACCACC (SEQ ID NO: 52) "Ro_Atf1_GLR001_PciI_F" AGCGGCCGCAAGCTTGCCGCCAATGACCCAGACGGACTTCATG (SEQ ID NO: 53) Ro_Atf1_GLR001_PciI_R GACCGACGTACCTCTGAGTGACATGTCACGAGGCCACGACCACCCT C (SEQ ID NO: 54) |

TABLE 4-continued

Primers used for cloning microbial and *Nannochloropsis* DGAT genes

```
Gene name       Primer sequences **

Nannochloropsis "DGAT10_GLR001_PciI_F"
gaditana        AGCGGCCGCAAGCTTGCCGCCAAATGGAAGATGAGGACCGCTTG
DGAT10          (SEQ ID NO:57)
(SEQ ID NO: 36) "DGAT10_GLR001_PciI_R"
                GACCGACGTACCTCTGAGTGACATGTTACTACTTAATAAGGAGTTT
                CTTGTCAGG (SEQ ID NO: 58)
                "DGAT10_416TEF_F"
                TCTAATCTAAGTTTTCTAGAACTAGTGGATCCCCCGCCACCATGGA
                AGATGAGGACCGCTTG (SEQ ID NO: 59)
                "EH_DGAT10_416TEF_R"
                GAGGTCGACGGTATCGATAAGCTTGATATCGAATTCCTGCAGCCCT
                TACTACTACTTAATAAGGAGTTTCTTGTCAGG (SEQ ID NO: 60)

Nannochloropsis "DGAT2_GLR001_PciI_F"
gaditana        AGCGGCCGCAAGCTTGCCGCCAAATGGCTGCCTTCTTTCGGCGTAG
DGAT2           GAATG (SEQ ID NO: 61)
(SEQ ID NO: 24) "DGAT2_GLR001_PciI_R"
                GACCGACGTACCTCTGAGTGACATGCTACGAAATCGCCACGAACTC
                TTCCGGGCGTG (SEQ ID NO: 62)

Nannochloropsis "DGAT7_GLR001_PciI_F"
gaditana        AGCGGCCGCAAGCTTGCCGCCAAATGGTGCTTGGGGAGGGCAAAA
DGAT7           AAAC (SEQ ID NO: 63)
(SEQ ID NO: 18) "DGAT7_GLR001_PciI_R"
                GACCGACGTACCTCTGAGTGACATGCTAAAACAGATGCAGCTCCCG
                GTC (SEQ ID NO: 64)
```

* Primer names that include "GLR001" have *Nannochloropsis* shuttle vector sequences and primer names including "416TEF" have yeast shuttle vector sequences; start and stop codons are in bold.

Example 8

DGAT Gene Complementation in a Double DGAT Knock-Out Yeast Strain

In order to determine whether microbial DGAT can function in eukaryotic strains, the five microbial DGAT described above were cloned behind the constitutively-expressed translation elongation factor 1 alpha (TEF1) promoter constructed onto the 416TEF yeast shuttle vector.

The original BY4741 mat a yeast strain containing the dga1 knockout was obtained by SGI from Stanford University *Saccharomyces* Genome Deletion Project collection (available at the world wide web address: www-sequence.stanford.edu/group/yeast_deletion_project/strain_a_mating-_type.txt). A PCR product-based homologous recombination deletion strategy was used for deletion of the lro1 gene (encoding another acyltransferase that may contribute to triglyceride synthesis) using the HIS3 marker to interrupt the lro1 gene. Nucleic acid sequence "arms" consisting of sequence extending 100 bp upstream and 100 by downstream of the lro1 gene were attached to the histidine marker which were then PCR-amplified and gel purified. The construct that included the HIS3 marker flanked by lro1 gene upstream and downstream sequences was introduced into yeast cells and lro1 gene knock-outs were selected for on histidine drop-out agar plates. The genotype of the double DGAT knock-out strain used in the experiments was: BY4741 MATα his3 Δ1 leu2Δ0 met15Δ0 ura3 Δ0 dga1×Δ:kanMX4 lro1−Δ:HIS3.

To transform the double knock-out with the DGAT constructs, a 5 mL primary culture of yeast was grown overnight at 30° C. in YEPD media that included 100 µg/mL kanamycin. A 50 mL secondary culture was started at an $OD_{600}$ of 0.25 and was grown for approximately 6 hours at 30° C. to an $OD_{600}$ of 1.5. The culture was harvested in a centrifuge (2000×g 4° C. for 8 minutes) and resuspended 10 mL of YPD/HEPES (made 10 mL YPD and 2 mL of 1M HEPES pH 8.0), after which 250 µL of 1M DTT was added and the culture was incubated for 15 minutes at 30° C. without shaking. The culture was brought up to a volume of 50 mL using ice cold (4° C.) $ddH_2O$. The yeast cells were harvested (4° C. 2000×g, 8 minutes) and resuspended in 25 mL ice cold water and centrifuged. The supernatant was removed and the cells were resuspended in 500 µL ice-cold sorbitol. Aliquot of cells (100 µL) were added to 2 mm electrocuvettes to which 6 µL of plasmid DNA/PCR product (500 ng-1 µg) was added. The electroporator was set to 1.25 kV capacitance of 25 µF and a resistance of 200-800 ohms. 400 µL of 1M sorbitol was immediately added and the cells were incubated for 1 hour at 30° C. (no shaking). The cell suspension was then centrifuged and resuspended in 150 µL of 1M sorbitol and plated on uracil or leucine drop out media agar plates. Yeast colonies appeared three days later and the colonies were streaked onto 10 µg/mL Nile Red-containing plates of drop-out agar for selection of plasmid-containing cells.

Yeast cells expressing the *Marinobacter* DGAT FFWS1 gene (SEQ ID NO:45, encoding the wax synthase/DGAT SEQ ID NO:46) or that included an empty vector control were also plated on uracil drop-out agar containing 10 µg/mL Nile Red and incubated for 3 days at 30° C. The *Marinobacter* DGAT FFWS1 expressing strain demonstrated Nile Red staining on the streaked plate that was significantly greater than that of the empty vector control strain.

Concurrently, 25 mL liquid drop-out media cultures spiked with 1% oleic acid were grown for three days and 5 mL aliquots of these cultures were centrifuged, grown for additional two days without oleic acid, and submitted for TAG analysis.

For analysis of TAG production by thin layer chromatography (TLC), one mL of the double knock-out yeast cultures that included either a gene encoding the *Marinobacter* DGAT (FFWS1; SEQ ID NO:46) or a gene encoding the *Nannochloropsis* DGAT Ng#10 (Ng10DGAT; SEQ ID NO:36), the double DGAT knock out strain (DGA1LRO1), or wild-type yeast (BY4741). One milliliter aliquots of the cultures were centrifuged and resuspended in 500 μL 3:1 Chloroform: methanol and the mixtures were bead-beaten for 10 minutes in the Geno-grinder to lyse the yeast cells. Two microliters of the chloroform:methanol extract were spotted on the thin layer plate. The solvent system was 90:10:1 hexane:diethyl ether:acetic acid and the chromatograph was run for 15 minutes in a TLC chamber. The TLC plate was then dried and placed in an iodine vapor chamber for 20 minutes to visualize lipid spots. When cell extracts were analyzed to detect TAG content in the double DGAT knockout yeast strains (DGA1LRO1), the strain that included an empty vector control did not show a spot migrating with the triolein standard (std), whereas the yeast strain that included a construct encoding *Marinobacter* DGAT (FFWS1; SEQ ID NO:46), *Nannochloropsis* DGAT Ng#10 (Ng10DGAT; SEQ ID NO:36), and "wild-type" yeast with functional DGATs (strain BY4741) did show a lipid migrating at the same distance as the triolein standard, with the extract from the strain expressing the *Marinobacter* DGAT (FFWS1; SEQ ID NO:46) showing noticeably more TAG.

Figure 8:
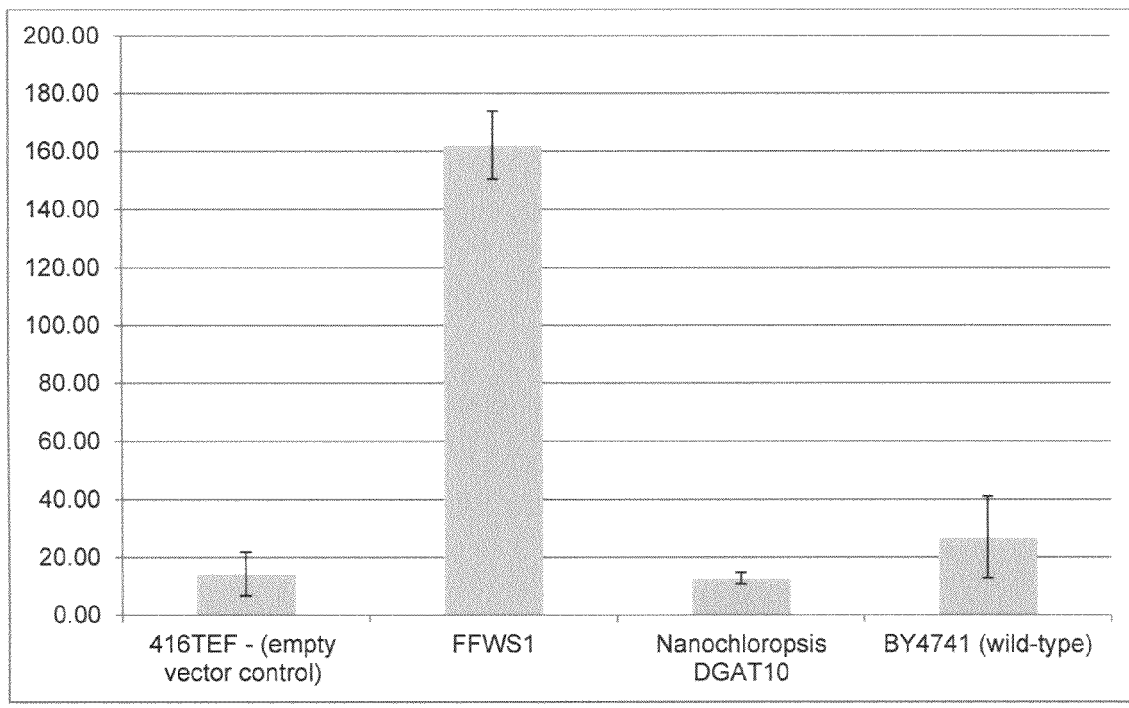
FIG. 8 is a graphical representation of DGAT expression increasing TAG content (μg/mL) in yeast. Thin layer chromatography (TLC) was used to detect TAG content in yeast expressing: (1) empty vector control in the double knockout strain (DGA1LR01), (2) *Marinobacter* DGAT (FFWS1), (3) *Nannochloropsis* DGAT Ng#10 (NanoDGAT10), and (4) "wild-type" yeast with functional DGATs (BY4741). See Example 8 herein.

TAG analysis of yeast including the empty vector (416TEF—empty vector control), yeast including a construct that included the *Marinobacter* DGAT (FFWS1) gene (SEQ ID NO:45), yeast including a construct that included the *Nannochloropsis* DGAT Ng#10 gene (SEQ ID NO:35), and "wild-type" yeast with functional endogenous DGATs (BY4741) demonstrated expression of the microbial *Marinobacter* WS/DGAT gene (SEQ ID NO:45) was particularly effective for production of TAGs in eukaryotic cells (FIG. 8).

phosphate antiporter were amplified using Phusion polymerase (Finnzyme) with the primers pairs M010 (SEQ ID NO:72) and M004 (SEQ ID NO:66), to produce an N-terminal fusion containing the first transmembrane domain ("fragment 1"; SEQ ID NO:73; protein sequence SEQ ID NO:74), or M010 (SEQ ID NO:72) and M005 (SEQ ID NO:67) to produce an N-terminal fusion containing the first two transmembrane domains (fragment 2; SEQ ID NO:75; protein sequence SEQ ID NO:76) (see Table 5). The open reading frames for the *Euonymus* diacylglycerol acetyltransferase gene (EaDGAcT, genbank ID: GU594061; SEQ ID NO:77; protein sequence SEQ ID NO:78) and Peanut soluble DGAT (AhDGAT, genbank ID:AY875644; SEQ ID NO:79; protein sequence SEQ ID NO:80) were synthesized by DNA 2.0 (Menlo Park, Calif. 94025) and cloned into the PJ201 plasmid. AhDGAT was amplified with the primer pair M009 (SEQ ID NO:71) and M002 (SEQ ID NO:65) to produce "fragment 3" for cloning into the plasmid PE-1261 as described below. An EaDGAcT amplicon ("fragment 4") intended for fusion with fragment 1 was amplified using the primer pair M006 (SEQ ID NO:68) and M008 (SEQ ID NO:70); for the EaDGAcT amplicon (fragment 5) intended for fusion with fragment TMD-2, amplification used the primer pair M007 (SEQ ID NO:69) and M008 (SEQ ID NO:70).

TABLE 5

Primers used in cloning DGAT genes.

| Primer name | Primer sequence | generated fragment |
|---|---|---|
| M002 | 5'-CGACTCTAGAAGATCTTTATTCATTAGTACTTTCCTGATT-3' SEQ ID NO: 65 | 3 |
| M004 | 5'-TCTTGATGAGCATCCATCATCCACGGCAGCGGCAGCA-3' SEQ ID NO: 66 | 1 |
| M005 | 5'-TCTTGATGAGCATCCATCATGATCCCAAAAAGCCACAAAG-3' SEQ ID NO: 67 | 2 |
| M006 | 5'-TGCTGCCGCTGCCGTGGATGATGGATGCTCATCAAGAA-3' SEQ ID NO: 68 | 4 |
| M007 | 5'-CTTTGTGGCTTTTTGGGATCATGATGGATGCTCATCAAGA-3' SEQ ID NO: 69 | 5 |
| M008 | 5'-CGACTCTAGAAGATCTTCAATTTCCACACACAAACC-3' SEQ ID NO: 70 | 4, 5 |
| M009 | 5'-GCTTGCCGCCAACATGGAGGTTTCAGGCGCCGT-3' SEQ ID NO: 71 | 3 |
| M010 | 5'-GCTTGCCGCCAACATGAGACTATTGGTACTTGGTCT-3' SEQ ID NO: 72 | 1, 2 |

Example 9

Cloning of Peanut (*Arachis hypogaea*) and Burning Bush (*Euonymus alatus*) DGAT Genes for Transformation into Wild-Type *Nannochloropsis gaditana*

N-terminal fragments of an *N. gaditana* gene encoding a putative chloroplast inner envelope glucose-6-phosphate/

For cloning *Nannochloropsis* shuttle vector GLR001 (FIG. 6), the vector was isolated from 10 mL of culture and linearized by restriction digestion with PciI and BglII. The BPS Bioscience cloning kit was used according to manufacturer's instructions to assemble the desired plasmids using the following vector/fragment combinations: (i) linearized vector and fragment 3 for PE-1391, (ii) linearized vector and fragments 1, 4 for PE-1392, and (iii) linearized vector and fragments 2, 5 for PE-1393. Sequences for the desired vectors were confirmed for the entire open reading frames inserted into the vector.

Transformation of *Nannochloropsis*

*Nannochloropsis gaditana* cells were grown in PM064 media and harvested at a concentration between $1-3 \times 10^7$ cells/mL. Cells were centrifuged at 2500×g for 10 minutes at 25° C. to pellet the cells. Cells were resuspended in a sterile solution of 385 mM sorbitol, and centrifuged. Cells were washed two more times in sorbitol to remove all traces of media. The cell pellet was resuspended in sorbitol to a final concentration of 1×10$^{10}$ cells/mL. Linearized plasmid DNA was aliquoted into microfuge tubes at a concentration between 0.5-5 µg DNA, and 100 mL of cell mixture was mixed with the DNA. The mixture was transferred to chilled electroporation cuvettes with a gap distance of 2 mm. The electroporator was set to 50 µF capacitance, 500 ohms resistance and 2.2 kV voltage. Following electroporation, samples were resuspended in 1 mL of sorbitol and incubated on ice for a few minutes. Cells were transferred to 15 mL conical tubes containing 10 mL of fresh media, and allowed to recover overnight in dim light (~5 µE). The next day, cells were plated on PM024 plates containing 5 µg/mL zeocin at a concentration between 5-7×10$^8$ cells/mL. Plates were incubated under constant light (~80 µE) until colonies appeared (~2-3 weeks). Typically, 12-20 clones were picked from transformation plates, restreaked to a patch on a selection plate. Clones chosen to be further assayed were confirmed to have both the ble gene and the exogenous DGAT gene by PCR.

Nannochloropsis Cell Culture

Nannochloropsis patch plates were scraped using a sterile 1 µL loop and inoculated into 2.5 mL media and grown at 25° C. shaking at 200 rpm on an orbital shaker with a 0.75 inch throw. Cells were incubated in an atmosphere containing 1% $CO_2$ and ~170 µE, constant light. For nitrogen starvation experiments, an extra loop of cells from the plate was inoculated into each nitrogen deficient well, as those cells were not expected to divide much in nitrogen deficient conditions. 300 µL of sample was removed each day on and an OD, cell count, chlorophyll fluorescence were measured.

Measuring Cell Density

Individual cells were counted and assayed for chlorophyll fluorescence using an Accuri cytometer. Alternatively, cell cultures were diluted to be less than an absorbance of 0.5 at 730 nm ($OD_{730}$) and measured for the absorbance at 730 nm. If cells were measured in 96 well clear bottom plate, a correction factor of 0.9 was applied to make it equivalent to measurement in a cuvette.

Analytical Quantitation

Samples were prepared for measurement of TAG (triacylglycerol) and FAME (Fatty Acid Methyl Ester) content. Briefly, 2 mL of whole culture was submitted for TOC and FAME measurements, while 5 mL of whole culture was pelleted and submitted for TAG analysis. TAG was analyzed as described in Example 6, above.

Example 10

Comparison of *Nannochloropsis* Grown in 100 mL and 2 mL Cultures

To validate the use of 2 mL cultures in multiwall plates for testing the physiology and productivity of algal strains, *Nannochloropsis gaditana* cells were grown in PM023 nutrient replete ("replete") or PM027 nitrogen-deficient ("starved") medium in 2 mL and 100 mL cultures for 5 days at 25° C., 170 µE light and 1% $CO_2$, and assayed for cell density (FIG. 9A), photosynthetic efficiency (FIG. 9B), and mean chlorophyll fluorescence (FIG. 9C). In addition, lipid content of the cells grown in nitrogen replete or nitrogen deficient media for 4 days was determined (FIG. 9D). The optical density $OD_{730}$ was measured for each 2 mL culture in a 24 well plate, averaged and compared to a second plate to determine inter-well variability (FIG. 9E) and intra-well variability (FIG. 9F). The figures demonstrate that for all parameters tested, 2 mL cultures in multiwall plates closely track 100 mL cultures.

Example 11

Correlation of Nile Red Staining and TAG Content in *Nannochloropsis gaditana*

Figure 10:
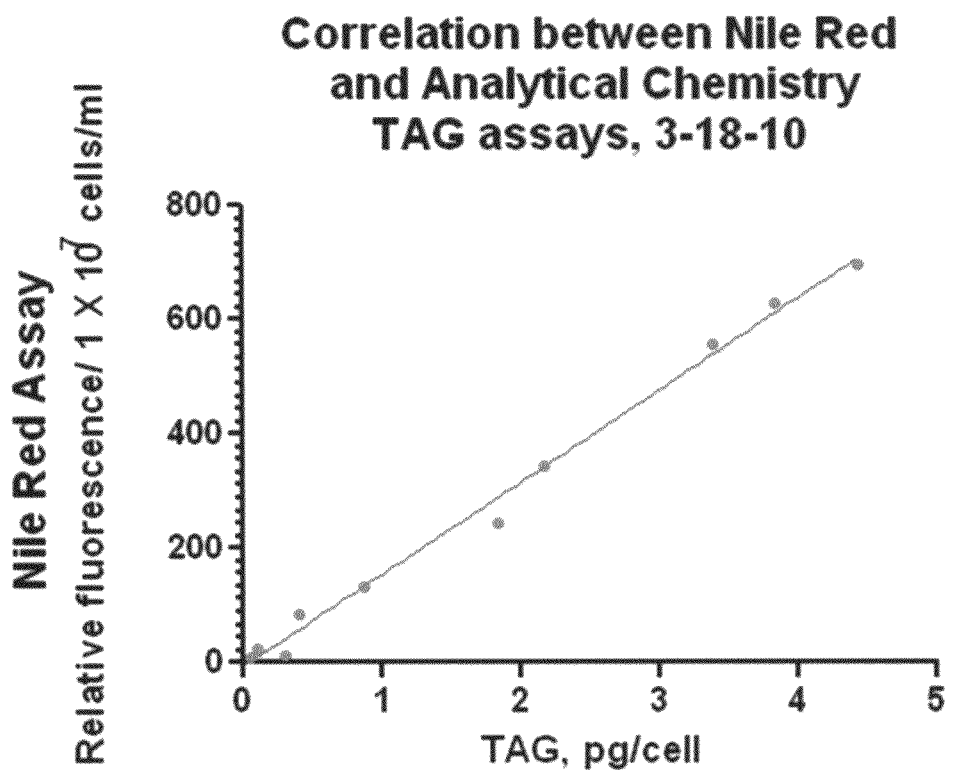
FIG. 10 is a graphical representation demonstrating that Nile Red staining of *N. gaditana* correlates with TAG content (pg/cell), which establishes reliability of the Nile Red assay.

A rapid and sensitive assay for the lipid content of algae was needed in order to screen transformants in 24-well plates. Lipid dyes such as Nile Red have been used in algae to estimate the lipid content (Greenspan et al. 1985). Nile Red preferentially stains neutral lipids, such as TAG (Greenspan et al. (1985) *J. Cell Biol.* 100: 965-973; Chen et al. (2009) *J Microbiol Methods* 77: 41-47). To determine whether there was a correlation between Nile red signal and lipid content of the algal cells, algae were grown in PM010 media and allowed to deplete the nitrogen in the media, inducing lipid accumulation. Samples were taken each day and cell concentration was normalized to 1×10$^7$ cells/mL with water before staining with Nile Red. Cells were diluted 1:10 in distilled $H_2O$, and 200 µL of cell solutions were transferred to a 96 well opaque microtiter plate. 1 µL of the Nile red stock solution (0.16 mg/mL in DMSO) was added to each well and covered with aluminum foil to keep out the light. Cells were shaken for 30 seconds in a microtiter shaker and allowed to incubate at room temperature for 15 minutes. Plates were read in the spectrophotometer at Em 510 nm, Ex 570 nm. The same samples were analyzed for TAG content using HPLC. There was a strong linear correlation between the amount of TAG per cell measured by HPLC and the Nile Red signal (FIG. 10), establishing the reliability of the Nile Red assay.

Figure 11:
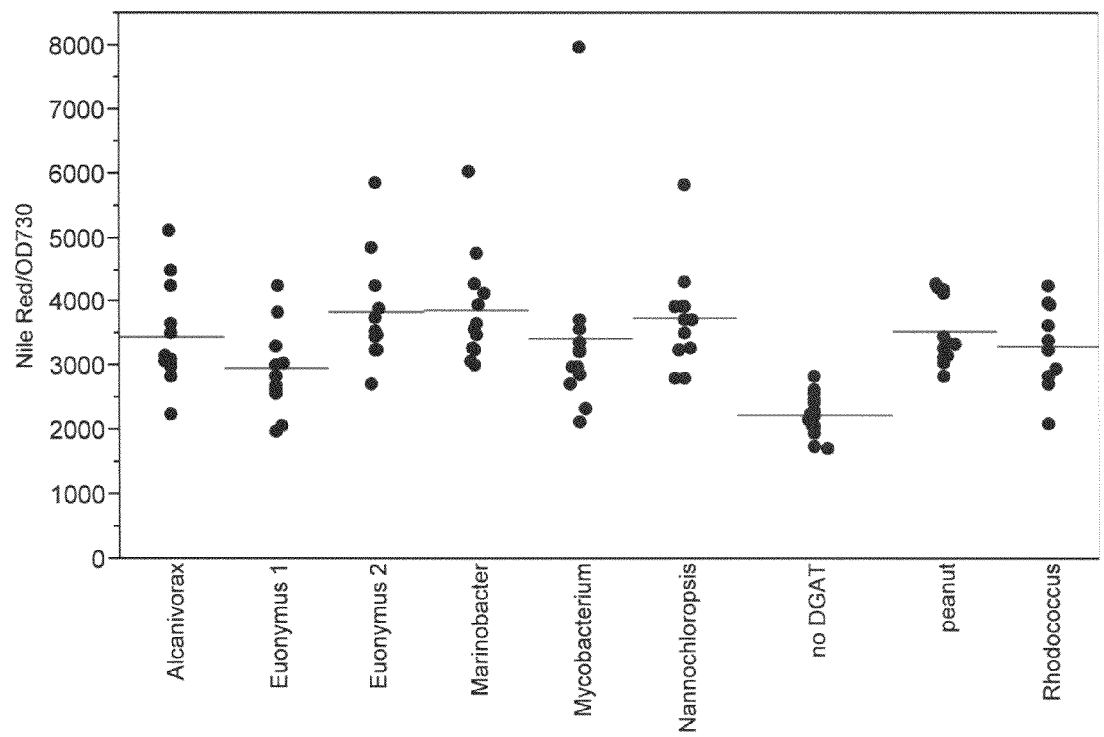
FIG. 11 is a graphical representation demonstrating TAG accumulation in various isolates transformed with DGAT expression vectors. Lines indicate mean for each group.

Based on statistical analysis, the lipid content of some DGAT transformants (*Nannochloropsis* DGAT10, peanut (*Arachis hypogaea*), *Rhodococcus, Alcanivorax,* and *Marinobacter* DGATs, but not the *Mycobacterium* or *Euonymus* DGATs) was found to be higher than control vector transformants when assayed at one day after inoculation of the cultures, an effect that disappeared by day 4 (FIG. 11). One possible interpretation is that ectopic DGAT expression did result in an increase in TAG accumulation while the cells were patched on agar plates, but as the cells start growing in liquid culture they assimilated the TAG into biomass and did not accumulate more.

Those skilled in the art will recognize, or be able to ascertain using no more than routine experimentation, many equivalents to the specific embodiments of the invention described herein. Such equivalents are intended to be encompassed by the following claims.

What is claimed is:

1. An expression cassette comprising a heterologous promoter operably linked to a nucleotide sequence encoding a diacylglycerol acyltransferase selected from the group consisting of an amino acid sequence having at least 85% identity to SEQ ID NO:18; an amino acid sequence having at least 85% identity to SEQ ID NO:24; and an amino acid sequence having at least 85% identity to SEQ ID NO:36.

2. A recombinant eukaryotic photosynthetic microorganism comprising a non-native gene encoding a diacylglycerol acyltransferase selected from the group consisting of an amino acid sequence having at least 85% identity to SEQ ID NO:18; an amino acid sequence having at least 85% identity to SEQ ID NO:24; and an amino acid sequence having at least 85% identity to SEQ ID NO:36;

wherein the recombinant eukaryotic photosynthetic microorganism produces a greater amount of triglyceride than a control eukaryotic photosynthetic microorganism that is substantially identical to the recombinant photosynthetic eukaryotic microorganism in all respects except that the control eukaryotic photosynthetic microorganism lacks the non-native gene.

3. The recombinant eukaryotic photosynthetic microorganism of claim 2, wherein the recombinant eukaryotic photosynthetic microorganism produces a greater amount of triglyceride under nitrogen replete conditions in which inorganic carbon is substantially the sole source of carbon in the culture medium.

4. The recombinant eukaryotic photosynthetic microorganism of claim 2, wherein the amino acid sequence further comprises a heterologous localization sequence that targets the amino acid sequence to the chloroplast or endoplasmic reticulum.

5. A recombinant algal cell comprising a non-native gene encoding a diacylglycerol acyltransferase selected from the group consisting of an amino acid sequence having at least 85% identity to SEQ ID NO:18, an amino acid sequence having at least 85% identity to SEQ ID NO:24, and an amino acid sequence having at least 85% identity to SEQ ID NO:36.

6. The recombinant eukaryotic photosynthetic microorganism of claim 2, wherein the non-native gene encodes a diacylglycerol acyltransferase selected from the group consisting of an amino acid sequence having at least 90% identity to SEQ ID NO:18; an amino acid sequence having at least 90% identity to SEQ ID NO:24; and an amino acid sequence having at least 90% identity to SEQ ID NO:36.

7. The recombinant eukaryotic photosynthetic microorganism of claim 2, wherein the recombinant eukaryotic photosynthetic microorganism is a recombinant algal cell of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.*

8. The recombinant algal cell of claim 7, wherein the recombinant algal cell is a *Nannochloropsis* species.

9. The recombinant eukaryotic photosynthetic microorganism of claim 2, wherein the recombinant eukaryotic photosynthetic microorganism produces a greater amount of triglyceride under nitrogen replete conditions than is produced by a control eukaryotic photosynthetic microorganism substantially identical to the recombinant eukaryotic photosynthetic microorganism in all respects and cultured under substantially the same conditions, except that the control eukaryotic photosynthetic microorganism does not include the non-native gene encoding a diacylglycerol acyltransferase.

10. The recombinant eukaryotic photosynthetic microorganism of claim 9, wherein the recombinant eukaryotic photosynthetic microorganism produces a greater amount of triglyceride after one day of culturing under nitrogen replete conditions than is produced by a control eukaryotic photosynthetic microorganism substantially identical to the recombinant eukaryotic photosynthetic microorganism in all respects and cultured under substantially the same conditions, except that the control eukaryotic photosynthetic microorganism does not include the non-native gene encoding a diacylglycerol acyltransferase.

11. A method for producing a triglyceride in a recombinant eukaryotic photosynthetic microorganism, the method comprising culturing a recombinant eukaryotic photosynthetic microorganism according to claim 2 under culture conditions such that diacylglycerol acyltransferase encoded by the non-native gene is expressed to produce a triglyceride.

12. The method of claim 11, wherein the culture conditions are nitrogen replete.

13. The method of claim 12, wherein the culture conditions are substantially or entirely photoautotrophic.

14. The method of claim 11, wherein the recombinant eukaryotic photosynthetic microorganism produces a greater amount of triglyceride under nitrogen replete conditions than is produced by a control eukaryotic photosynthetic microorganism substantially identical to the recombinant eukaryotic photosynthetic microorganism in all respects and cultured under the substantially same conditions, except that the control eukaryotic photosynthetic microorganism does not include the non-native gene.

15. The method of claim 11, wherein the recombinant eukaryotic photosynthetic microorganism is a recombinant algal cell of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halo cafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.*

16. The method of claim 15, wherein the recombinant algal cell is a *Nannochloropsis* cell.

17. The method of claim 11, wherein the recombinant eukaryotic photosynthetic microorganism is proliferating and generating triglyceride at levels higher than the triglyceride levels generated by a non-transfected control microorganism cultured under substantially the same conditions.

18. The method of claim 17, wherein the recombinant eukaryotic photosynthetic microorganism generates triglyceride in nitrogen replete conditions at levels at least 70% greater in comparison to a non-transfected control microorganism.

19. The method of claim 17, wherein the recombinant eukaryotic photosynthetic microorganism generates triglyceride in nitrogen replete conditions at levels at least two fold greater in comparison to a non-transfected control microorganism.

20. The method of claim 11, wherein the non-native gene encodes a diacylglycerol acyltransferase having at least 90% identity to SEQ ID NO:18; or having at least 90% identity to SEQ ID NO:24; or having at least 90% identity to SEQ ID NO:36.

* * * * *

SEQUENCE LISTING

<160> NUMBER OF SEQ ID NOS: 87

<210> SEQ ID NO 1
<211> LENGTH: 2251

```
<212> TYPE: DNA
<213> ORGANISM: Mus musculus

<400> SEQUENCE: 1
ccgcgcttcg ctggctttct gctcatctag ggtggcagcg gctacctacc tcagctctcg      60
ccctgctgcc gccacggcct gggcgctgtc cctcagctcc cggagctcag cgcgaagccc     120
tggccccggc ggccggggca tgggtcaggg gcgcggcgtg aggcggcttt ctgcacggcc     180
gtgacgtgca ttggcttcag catgaagacc ctcatcgccg cctactccgg ggtcctgcgg     240
ggtgagcgtc gggcggaagc tgcccgcagc gaaaacaaga ataaaggatc tgccctgtca     300
cgcgaggggt ctgggcgatg gggcactggc tccagcatcc tctcagccct ccaagacatc     360
ttctctgtca cctggctcaa cagatctaag gtggaaaaac agctgcaggt catctcagta     420
ctacaatggg tcctatcctt cctggtgcta ggagtggcct gcagtgtcat cctcatgtac     480
accttctgca cagactgctg gctgatagct gtgctctact tcacctggct ggcatttgac     540
tggaacacgc ccaagaaagg tggcaggaga tcgcagtggg tgcgaaactg gccgtgtgg      600 cgctacttcc gagactactt tcccatccag ctggtgaaga cacacaacct gctgaccacc     660
aggaactata tctttggata ccaccccat ggcatcatgg gcctgggtgc cttctgtaac      720
ttcagcacag aggctactga agtcagcaag aagtttcctg gcataaggcc ctatttggct     780
acgttggctg gtaacttccg gatgcctgtg cttcgcgagt acctgatgtc tggaggcatc     840
tgccctgtca accgagacac catagactac ttgctctcca gaatgggag tggcaatgct      900 atcatcatcg tggtgggagg tgcagctgag tccctgagct ccatgcctgg caagaacgca     960
gtcaccctga gaaccgcaa aggctttgtg aagctggccc tgcgccatgg agctgatctg     1020
gttcccactt attcctttgg agagaatgag gtatacaagc aggtgatctt tgaggagggt     1080
tcctggggcc gatgggtcca agaagttc cagaagtata ttggttcgc cccctgcatc       1140 ttccatggcc gaggcctctt ctcctctgac acctggggc tggtgcccta ctccaagccc     1200
atcaccaccg tcgtggggga gcccatcact gtccccaagc tggagcaccc gacccagaaa     1260
gacatcgacc tgtaccatgc catgtacatg gaggccctgg tgaagctctt tgacaatcac     1320
aagaccaaat ttggccttcc agagactgag gtgctggagg tgaactgacc cagccctcgc     1380
gtgccagctc ctgggaggga cgactgcaga tccttttcta ccgagttctt gagtgcattt     1440
tgttctgtaa atttggaagc gtcatgggtg tctgtgggtt atttaaaaga aattataatt     1500
tgttaaacca ttgcaatgtt agatgttttt taagaaggga agagtcagta ttttaagctc     1560
acttctagtg tgtcctgctc aaggtggagg ctgatattta tgggccttgg tggtttctta     1620
cccacccctt ctagcgttcc ccagacgaca gacacttggc cctggctagc tgggcaaggg     1680
cagtccttag tgactccagg gattcttgag aggcagaggc catgtccac ccgtggctgc      1740 aggtcgggtt cctcgtacca aggggaggct gagggcacag ctggccccac ttggggaggg     1800
tagataacat ctggactgcc cggcttgggt ctctgctcct cacccctagcc ctcttctcca    1860 atctgagcct accctggcct cctgtctcct ggctagggac acggctgtcc cacaggtgcc     1920
gtcttgggtt atctcgctgc tgttggctgg tttcactctg gaggttggca ccatggacac     1980
agctcagcgt tgctctggcg catatcctcc tgagccacac cccaagtctg gtgtgaggaa     2040
gggcttctct tctcttcaca gaggtgcctg gcttcctgtg cagcacactg ggtccaggac     2100
aggaggcccc ccccccaaac caagcctcac gtgtgtgcct ttatgaggcg ttgggagaaa     2160
gctaccctcc tgtgtattct gttttctcca tgagattgtt gtgccatgtc acactttgt      2220
```
atattcctag actaataaat ggaaacaaga a                                    2251

<210> SEQ ID NO 2
<211> LENGTH: 388
<212> TYPE: PRT
<213> ORGANISM: Mus musculus

<400> SEQUENCE: 2

Met Lys Thr Leu Ile Ala Ala Tyr Ser Gly Val Leu Arg Gly Glu Arg
1               5                   10                  15

Arg Ala Glu Ala Ala Arg Ser Glu Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Val Pro Lys Leu Glu His Pro Thr Gln
            340                 345                 350

Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
    370                 375                 380

Leu Glu Val Asn
385

<210> SEQ ID NO 3
<211> LENGTH: 1056
<212> TYPE: DNA
<213> ORGANISM: Artificial Sequence
<220> FEATURE:
<223> OTHER INFORMATION: Mus musculus MmDGAT2 truncated by 55 amino acid
      residues

<400> SEQUENCE: 3
gccccgactc tagaagatct ttattacaac tcgtcgtcgt tgacctccag cacttctgtt      60
tcgggaagcc cgaacttggt cttatggtta tcaaacagct tcaccaacgc ttccatatac     120
atcgcgtgat aaagatcaat gtccttttga gtgggatgct ccagtttcgg gaccgtaatt     180
ggctctccga ccacggtggt aatcggcttg ctataaggca ccagccccca cgtgtcggag     240
gaaaacaggc cacgcccgtg aaaatgcagg gagcgaacc cgatgtactt ctggaacttt      300
ttctggaccc acctgcccca gcttccctct caaagatga cctgcttgta cacctcgttc      360
tcgccaaagc tgtacgtggg caccagatcg gcaccgtgcc gcagggccag cttcacaaag     420
cccttgcgat tcttgagagt aactgcattc tttcccggca tcgaggagag ggactcagca     480
gctccgccga ccacaatgat gattgcgttg ccagagccat tcttggagag aaggtagtcg     540
atggtgtcac gattaacggg acaaattccc ccggacatca ggtactctcg caacacaggc     600
atacggaagt tgcccgcgag ggtggccaag taaggacgaa tgccggggaa cttcttggac     660
acttccgtgg cttccgtcga aaagttgcag aacgcaccaa gcccatgat cccgtgcgga      720 tggtagccaa agatgtagtt ccgggtagtg agcaagttat gggttttgac caattgaata     780
gggaagtagt cgcggaagta ccgccacacg gcccaattgc gcaccactg cgaccggcga      840 ccaccctttt tgggggtgtt ccagtcgaat gcaagccagg tgaagtacaa caccgcgatg     900
agccaacaat ctgtgcagaa cgtatacatc aagatgacag agcaggccac cccgagcacg     960
agaaagctga ggacccactg aaggacagag ataacttgca attgtttctc caccttgctg    1020
cggttgagcc acgtcaccat gttggcggca agcttg                              1056

<210> SEQ ID NO 4
<211> LENGTH: 338
<212> TYPE: PRT
<213> ORGANISM: Artificial Sequence
<220> FEATURE:
<223> OTHER INFORMATION: Mus musculus MmDGAT2 truncated by 55 amino acid
      residues

<400> SEQUENCE: 4

Met Val Thr Trp Leu Asn Arg Ser Lys Val Glu Lys Gln Leu Gln Val
1               5                   10                  15

Ile Ser Val Leu Gln Trp Val Leu Ser Phe Leu Val Leu Gly Val Ala
            20                  25                  30

Cys Ser Val Ile Leu Met Tyr Thr Phe Cys Thr Asp Cys Trp Leu Ile
        35                  40                  45

Ala Val Leu Tyr Phe Thr Trp Leu Ala Phe Asp Trp Asn Thr Pro Lys
    50                  55                  60

Lys Gly Gly Arg Arg Ser Gln Trp Val Arg Asn Trp Ala Val Trp Arg
65                  70                  75                  80

```
Tyr Phe Arg Asp Tyr Phe Pro Ile Gln Leu Val Lys Thr His Asn Leu
                 85                  90                  95
Leu Thr Thr Arg Asn Tyr Ile Phe Gly Tyr His Pro His Gly Ile Met
            100                 105                 110
Gly Leu Gly Ala Phe Cys Asn Phe Ser Thr Glu Ala Thr Glu Val Ser
        115                 120                 125
Lys Lys Phe Pro Gly Ile Arg Pro Tyr Leu Ala Thr Leu Ala Gly Asn
    130                 135                 140
Phe Arg Met Pro Val Leu Arg Glu Tyr Leu Met Ser Gly Gly Ile Cys
145                 150                 155                 160
Pro Val Asn Arg Asp Thr Ile Asp Tyr Leu Leu Ser Lys Asn Gly Ser
                165                 170                 175
Gly Asn Ala Ile Ile Ile Val Val Gly Gly Ala Ala Glu Ser Leu Ser
            180                 185                 190
Ser Met Pro Gly Lys Asn Ala Val Thr Leu Lys Asn Arg Lys Gly Phe
        195                 200                 205
Val Lys Leu Ala Leu Arg His Gly Ala Asp Leu Val Pro Thr Tyr Ser
    210                 215                 220
Phe Gly Glu Asn Glu Val Tyr Lys Gln Val Ile Phe Glu Glu Gly Ser
225                 230                 235                 240
Trp Gly Arg Trp Val Gln Lys Lys Phe Gln Lys Tyr Ile Gly Phe Ala
                245                 250                 255
Pro Cys Ile Phe His Gly Arg Gly Leu Phe Ser Ser Asp Thr Trp Gly
            260                 265                 270
Leu Val Pro Tyr Ser Lys Pro Ile Thr Thr Val Val Gly Glu Pro Ile
        275                 280                 285
Thr Val Pro Lys Leu Glu His Pro Thr Gln Lys Asp Ile Asp Leu Tyr
    290                 295                 300
His Ala Met Tyr Met Glu Ala Leu Val Lys Leu Phe Asp Asn His Lys
305                 310                 315                 320
Thr Lys Phe Gly Leu Pro Glu Thr Glu Val Leu Glu Val Asn Asp Asp
                325                 330                 335
Glu Leu

<210> SEQ ID NO 5
<211> LENGTH: 375
<212> TYPE: DNA
<213> ORGANISM: Streptoalloteichus hindustanus

<400> SEQUENCE: 5
atggccaagc tgaccagcgc cgttccggtg ctcaccgcgc gcgacgtcgc cggagcggtc      60
gagttctgga ccgaccggct cgggttctcc cggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300
ccgtggggggc gggagttcgc cctgcgcgac ccggccggca actgcgtgca cttcgtggcc     360
gaggagcagg actaa                                                      375

<210> SEQ ID NO 6
<211> LENGTH: 124
<212> TYPE: PRT
<213> ORGANISM: Streptoalloteichus hindustanus

<400> SEQUENCE: 6
```

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
                20                  25                  30

Phe Val Glu Asp Asp Phe Ala Gly Val Val Arg Asp Asp Val Thr Leu
            35                  40                  45

Phe Ile Ser Ala Val Gln Asp Gln Val Val Pro Asp Asn Thr Leu Ala
        50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
                100                 105                 110

Gly Asn Cys Val His Phe Val Ala Glu Glu Gln Asp
                115                 120
```

<210> SEQ ID NO 7
<211> LENGTH: 1000
<212> TYPE: DNA
<213> ORGANISM: Phaeodactylum tricornutum

<400> SEQUENCE: 7

| | | | | | |
|---|---|---|---|---|---|
| ggatttgcct | cccatgcgcg | gaaagtttgc | acagagccag | ctacagcaat | gtcaatttct | 60 |
| tttgcagtgg | ttggcacggg | ttgatgggct | gcactatcga | tattgctgtc | aatggctgtg | 120 |
| ctttggtttg | acatcggtgc | tgtgcgacgt | ttggccatgc | gctcggccat | tctgtttttt | 180 |
| cgaatatgca | aagttgtctc | ttcccgagat | cgacgaccgt | cttcagctga | cacggtcttc | 240 |
| ttaaatgacg | catcacgacg | aggaactaaa | gccgcccagg | tatacaattg | tggcattaga | 300 |
| gactgaatac | aatgcctcga | atagcggaga | tactaagggc | cgttatttcg | tacctgcggc | 360 |
| gactagggtc | atgattgtat | ctctaagaac | aacagggaa | atttctgatc | aaggtcgacg | 420 |
| ggtaaaaggc | ggaacaagaa | taaaggatg | gtgatacgga | acagagcaac | gctacagaaa | 480 |
| agtgaggatc | gccaaccatc | aagttgtggc | gatgcgatac | ttttttgcgat | aacgtctcgc | 540 |
| gctctatgat | tttcttttgtt | atattaattt | gttcaacatg | agctaattaa | ccgaaacctt | 600 |
| atgcctcaac | tgccgactca | gcacaagtac | ctaactttgc | aaggttttgt | cgtatacgtc | 660 |
| tgtccataga | acgttgacta | atgtaagagg | aagattttg | tggacgttgt | gcgcttgaca | 720 |
| tccattggtt | gatgtggttt | tgctgatgtc | acggcatcct | gagtccccta | acgtttcact | 780 |
| tggcgcctcg | cagctgttg | cagttcgctc | ggtatctttt | tctaggatct | tccgcagatt | 840 |
| tgaagttcgc | atcgaaacca | ttcctgtcgt | ggaaaaaagg | cctggatcgc | atcttgcagg | 900 |
| tgcaacgcta | attcttctcc | attcataaaa | acagaactcg | tagaaaacga | ttcaaatctt | 960 |
| ttttcgcctt | tctaaacatc | agtaattcta | tcaaattcta | | | 1000 |

<210> SEQ ID NO 8
<211> LENGTH: 479
<212> TYPE: DNA
<213> ORGANISM: Thalassiosira pseudonana

<400> SEQUENCE: 8

| | | | | | |
|---|---|---|---|---|---|
| tcactctgtc | gcgctgttgg | cgccactact | ttgggggtac | gagtttaggc | tgccttggct | 60 |
| gggataaaga | atgataagtt | tacataattt | gtattggaaa | tccatcgagt | tttggattca | 120 |

```
gttgacgtct cctgcgttac tatgtcttca ttctctccag tatcaatgcc tatggttcgt      180
cgacattgag cacatttctt tcatcagcgc gatgcatgca atcatcactt cgcaatcttg      240
acaaacatcc tcaatgattc ctccacctct cccaacaaag tcaatgcatt catccttgga      300
tcttctcctc caccgaacgg ccgtgaagcc gactccatta gtgcatccag tccatcaaaa      360
taccgtatga attcccgaaa agattcactt gccaagtact gtttgtcatc ctcctcttca      420
ggtatctcat caatgagtgc atttgcagct atacgaatct ttgactcgga aatcaatcc       479

<210> SEQ ID NO 9
<211> LENGTH: 203
<212> TYPE: DNA
<213> ORGANISM: Simian virus 40

<400> SEQUENCE: 9 aagcttttg caaaagccta ggcctccaaa aaagcctcct cactacttct ggaatagctc        60
agaggccgag gcggcctcgg cctctgcata ataaaaaaaa attagtcagc catggggcgg      120
agaatgggcg gaactgggcg gagttagggg cgggatgggc ggagttaggg gcgggactat      180
ggttgctgac taattgagat gca                                              203

<210> SEQ ID NO 10
<211> LENGTH: 133
<212> TYPE: DNA
<213> ORGANISM: Artificial Sequence
<220> FEATURE:
<223> OTHER INFORMATION: chimeric intron

<400> SEQUENCE: 10
ctgtggagag aaaggcaaag tggatgtcag taagaccaat aggtgcctat cagaaacgca       60
agagtcttct ctgtctcgac aagcccagtt tctattggtc tccttaaacc tgtcttgtaa      120
ccttgatact tac                                                         133

<210> SEQ ID NO 11
<211> LENGTH: 222
<212> TYPE: DNA
<213> ORGANISM: Simian virus 40

<400> SEQUENCE: 11
taccacattt gtagaggttt tacttgcttt aaaaaacctc ccacacctcc ccctgaacct       60
gaaacataaa atgaatgcaa ttgttgttgt taacttgttt attgcagctt ataatggtta     120
caaataaagc aatagcatca caaatttcac aaataaagca ttttttttcac tgcattctag    180 ttgtggtttg tccaaactca tcaatgtatc ttatcatgtc tg                         222

<210> SEQ ID NO 12
<211> LENGTH: 243
<212> TYPE: DNA
<213> ORGANISM: Simian virus 40

<400> SEQUENCE: 12
catatggctg tggaatgagt gtgtcagtgg gtgtggaaag tccccaggct ccccagcagg       60
cagaagtatg caaagcatgc atctcaatta gtcagcaacc aggtgtggaa agtccccagg     120
ctccccagca ggcagaagta tgcaaagcat gcatctcaat tagtcagcaa ccatagtccc    180
gcccctaact ccgcccatcc cgcccctaac tccgcccagt tccgcccatt ctccgctcca    240
tcg                                                                    243
```

```
<210> SEQ ID NO 13
<211> LENGTH: 35
<212> TYPE: DNA
<213> ORGANISM: Artificial Sequence
<220> FEATURE:
<223> OTHER INFORMATION: Primer MsDGAT2 F2

<400> SEQUENCE: 13
caagcttgcc gccaacatgg tgacgtggct caacc                                35

<210> SEQ ID NO 14
<211> LENGTH: 44
<212> TYPE: DNA
<213> ORGANISM: Artificial Sequence
<220> FEATURE:
<223> OTHER INFORMATION: Primer MsDGAT2 R1

<400> SEQUENCE: 14
gccccgactc tagaagatct ttattacaac tcgtcgtcgt tgac                       44

<210> SEQ ID NO 15
<211> LENGTH: 23
<212> TYPE: DNA
<213> ORGANISM: Artificial Sequence
<220> FEATURE:
<223> OTHER INFORMATION: Primer MsDGAT2 geno F1

<400> SEQUENCE: 15
cccggaacta catctttggc tac                                              23

<210> SEQ ID NO 16
<211> LENGTH: 22
<212> TYPE: DNA
<213> ORGANISM: Artificial Sequence
<220> FEATURE:
<223> OTHER INFORMATION: Primer MsDGAT2 geno R1

<400> SEQUENCE: 16
gtggaaaatg cagggagcga ac                                               22

<210> SEQ ID NO 17
<211> LENGTH: 1194
<212> TYPE: DNA
<213> ORGANISM: Nannochloropsis gaditana

<400> SEQUENCE: 17
atggtgcttg gggagggcaa aaaaactgat ggcaagtcga ccgatccagc aaaagcgacc       60
gaggagaagc gcgtccccgc cccgctgcga gagcgcaaag ggaagaagca ggaagggaaa      120
gacttgcgaa ccccatctag caacctgaaa cctgcgcgtt cccccacgga ggtcgattgg      180
agttcttttc ccgagggaag ctacacacgt tttgggcatg gtggggattg gtggaccttc      240
ttgaaaggca cacttgccat tttaacagtg tgggcaacct ggttaggggg gggcacttca      300
cccgtatgga tggcttgttt atacatgcat gggtaccgag ttgcattctg gatcctgttg      360
ggccctttac tttatccgct tttccttcct gtcccagcct ggcctgcatt tgttcgtttc      420
gtgttggaca tggccggtta ttttgagggt ggggccgcca tgtacgtcga gaattctttc      480
aagggcagga atgtcaacgg tccaatcatg ctggccatgc atccccatgg gatcatgccg      540
cactccttcc ttttgaacgg cgcaggccgg attcatgccc aaaaaccccga attttacctc      600 ccccccccact accaagacat gtccctgaaa tcgacggggg tggcggaacc gctcctcttt      660
cgcatcccct tgatatctgc ctttctgtac ttttttggat gcgcggagcc ggcgtcgaag      720
```

-continued

```
gcgatgatgc acaacatctt ggagcggcag gtgccttttg cattttggt gggaggctcg    780 gaggagattt tgctgatgga gtatcaacga gagaatgtct acattttgga gcgaaaggc    840 ttcattaaat acgcgttaca gcacggctat actatcgccc tggggtattt gttcggagag    900
agcaacctgt accacaccat cacctggggc cggaagctcc ggcttgccct tttcaagcgc    960
ttcaagatcc caatcttctt cgcccgggga cgctggtttt tccccctact gcccgaacgg   1020 gccaccccc ttaacgccgt ggtcggaaac cccatcgacc tgcctcggat cgccgacccg    1080
acccaggagg acatagacaa ataccacgcg atctatatcg agaagctcac ggacttattt   1140
gagcggaata aggctgcctt tggatacccg gaccgggagc tgcatctgtt ttga          1194
```

<210> SEQ ID NO 18
<211> LENGTH: 397
<212> TYPE: PRT
<213> ORGANISM: Nannochloropsis gaditana

<400> SEQUENCE: 18

```
Met Val Leu Gly Glu Gly Lys Lys Thr Asp Gly Lys Ser Thr Asp Pro
1               5                   10                  15

Ala Lys Ala Thr Glu Glu Lys Arg Val Pro Ala Pro Leu Arg Glu Arg
            20                  25                  30

Lys Gly Lys Lys Gln Glu Gly Lys Asp Leu Arg Thr Pro Ser Ser Asn
        35                  40                  45

Leu Lys Pro Ala Arg Ser Pro Thr Glu Val Asp Trp Ser Ser Phe Pro
    50                  55                  60

Glu Gly Ser Tyr Thr Arg Phe Gly His Gly Gly Asp Trp Trp Thr Phe
65                  70                  75                  80

Leu Lys Gly Thr Leu Ala Ile Leu Thr Val Trp Ala Thr Trp Leu Gly
                85                  90                  95

Gly Gly Thr Ser Pro Val Trp Met Ala Cys Leu Tyr Met His Gly Tyr
            100                 105                 110

Arg Val Ala Phe Trp Ile Leu Leu Gly Pro Leu Leu Tyr Pro Leu Phe
        115                 120                 125

Leu Pro Val Pro Ala Trp Pro Ala Phe Val Arg Phe Val Leu Asp Met
    130                 135                 140

Ala Gly Tyr Phe Glu Gly Gly Ala Ala Met Tyr Val Glu Asn Ser Phe
145                 150                 155                 160

Lys Gly Arg Asn Val Asn Gly Pro Ile Met Leu Ala Met His Pro His
                165                 170                 175

Gly Ile Met Pro His Ser Phe Leu Leu Asn Gly Ala Gly Arg Ile His
            180                 185                 190

Ala Gln Lys Pro Glu Phe Tyr Leu Pro Pro His Tyr Gln Asp Met Ser
        195                 200                 205

Leu Lys Ser Thr Gly Val Ala Glu Pro Leu Leu Phe Arg Ile Pro Leu
    210                 215                 220

Ile Ser Ala Phe Leu Tyr Phe Phe Gly Cys Ala Glu Pro Ala Ser Lys
225                 230                 235                 240

Ala Met Met His Asn Ile Leu Glu Arg Gln Val Pro Phe Gly Ile Leu
                245                 250                 255

Val Gly Gly Ser Glu Glu Ile Leu Leu Met Glu Tyr Gln Arg Glu Asn
            260                 265                 270

Val Tyr Ile Leu Glu Arg Lys Gly Phe Ile Lys Tyr Ala Leu Gln His
        275                 280                 285

Gly Tyr Thr Ile Ala Leu Gly Tyr Leu Phe Gly Glu Ser Asn Leu Tyr
```

```
                    290                 295                 300
His Thr Ile Thr Trp Gly Arg Lys Leu Arg Leu Ala Leu Phe Lys Arg
305                 310                 315                 320

Phe Lys Ile Pro Ile Phe Phe Ala Arg Gly Arg Trp Phe Phe Pro Leu
                325                 330                 335

Leu Pro Glu Arg Ala Thr Pro Leu Asn Ala Val Val Gly Asn Pro Ile
            340                 345                 350

Asp Leu Pro Arg Ile Ala Asp Pro Thr Gln Glu Asp Ile Asp Lys Tyr
        355                 360                 365

His Ala Ile Tyr Ile Glu Lys Leu Thr Asp Leu Phe Glu Arg Asn Lys
    370                 375                 380

Ala Ala Phe Gly Tyr Pro Asp Arg Glu Leu His Leu Phe
385                 390                 395

<210> SEQ ID NO 19
<211> LENGTH: 21
<212> TYPE: DNA
<213> ORGANISM: Artificial Sequence
<220> FEATURE:
<223> OTHER INFORMATION: primer 7DGAT F1

<400> SEQUENCE: 19
atggtgcttg gggagggcaa a                                              21

<210> SEQ ID NO 20
<211> LENGTH: 21
<212> TYPE: DNA
<213> ORGANISM: Artificial Sequence
<220> FEATURE:
<223> OTHER INFORMATION: Primer 7DGAT R1

<400> SEQUENCE: 20
cttcaaaaca gatgcagctc c                                              21

<210> SEQ ID NO 21
<211> LENGTH: 37
<212> TYPE: DNA
<213> ORGANISM: Artificial Sequence
<220> FEATURE:
<223> OTHER INFORMATION: Primer 7DGAT F2

<400> SEQUENCE: 21
caagcttgcc gccaacatgg tgcttgggga gggcaaa                             37

<210> SEQ ID NO 22
<211> LENGTH: 41
<212> TYPE: DNA
<213> ORGANISM: Artificial Sequence
<220> FEATURE:
<223> OTHER INFORMATION: Primer 7DGAT R2

<400> SEQUENCE: 22
gccccgactc tagaagatct cttcaaaaca gatgcagctc c                        41

<210> SEQ ID NO 23
<211> LENGTH: 1446
<212> TYPE: DNA
<213> ORGANISM: Nannochloropsis gaditana

<400> SEQUENCE: 23
atgactgcct ctttcggcg taggaatggg agtgggagca gcacaagcag cagttcctcc     60
tccttggcag aagacaagca ctccatcctt tcctctgaaa tcgatccact cccttgttcg   120
```

```
cccteccacca ccgccagcac atggaaaggg cccgacgtgg cgaacaaggc gagggagtcg    180
acctgccttg ctccatcgca ctccacaaca agccaagtcg ctgctgtacc tggacagaac    240
ggggccattg ccactaccga agacgcctcc aagtctgaca tacgacacct acaaagaccg    300
ccccaggatc cccttaccga gcatattctc gacacaggaa acaaaggcac ggcaggacaa    360
ggacaccgcc ggcgcacgtc cgcgacgctc tcatcctggg cttctttttc ctcttcgaat    420
accctttcct tcttgacggg cgaggactcg tccatagtcg ccccgtccg ggggcctgcc     480
aagctggatt tctccacgcc cgtccaccca gccacgcaag ccgttgattt cgtcatcacc    540
ttcctcctcg tgcattacat ccaagtcttt tactctctcg tcttcctctt tatctacctg    600
gtccggcacg gctaccgttg gcccttgtc ctggccggcc tctacctccc ttcctatttt     660
atccccttcc aacgcctggg ggggtggccc ttccgccttc tcatgcggcg ccccttctgg    720
cgctgtgtcc agcgcacgct cgctttcaaa gtggaacggg aggtggaact ctcgcccgcc    780
acccagtaca tcttcggctg caccccac ggcatcctcc ttctctcccg ctttgccatc      840
tacgggggcc tctgggagaa gctcttcccg ggcgtgcact tcaagacctt ggccgccagc    900
cccttgttct ggatcccgcc catccgggag gtatcgatcc tcttgggggg cgtggacgcc    960
gggagggcct ctgccaatcg ggccttgcgg acggctact ccgtctccct ttacccgggg    1020
gggagcaagg agatctacac gacgaacccg tacacgcccg agaccacact ggtgctcaag   1080
attcggaagg gcttcattcg catggccctc cggtacggat gccctggt cctgtctac     1140
acctttggag agaagtacgc ctaccatcgt ctcggtcacg ccaccggctt cgcccactgg   1200
ctcctggcgg tgctgcgggt gccttttctg attttctggg gacgctggtg caccttatg   1260
cctctgaagc acacgcaggt gtcggtggtg gtagggaagc ccctcccagt ccccaagatc   1320
gagggggaac ccgcgcctga ggtggtggag gagtggctgc agcggtactg cgatgaggtg   1380
caggcactct ccaacggca taaacacaag tacgcacgcc cggaagagtt cgtggcgatt   1440
tcgtga                                                                1446
```

<210> SEQ ID NO 24
<211> LENGTH: 481
<212> TYPE: PRT
<213> ORGANISM: Nannochloropsis gaditana

<400> SEQUENCE: 24

```
Met Thr Ala Phe Phe Arg Arg Arg Asn Gly Ser Gly Ser Thr Ser
1               5                  10                  15
Ser Ser Ser Ser Ser Leu Ala Glu Asp Lys His Ser Ile Leu Ser Ser
            20                  25                  30
Glu Ile Asp Pro Leu Pro Cys Ser Pro Ser Thr Thr Ala Ser Thr Trp
        35                  40                  45
Lys Gly Pro Asp Val Ala Asn Lys Ala Arg Glu Ser Thr Cys Leu Ala
    50                  55                  60
Pro Ser His Ser Thr Thr Ser Gln Val Ala Val Pro Gly Gln Asn
65                  70                  75                  80
Gly Ala Ile Ala Thr Thr Glu Asp Ala Ser Lys Ser Asp Ile Arg His
                85                  90                  95
Leu Gln Arg Pro Pro Gln Asp Pro Leu Thr Glu His Ile Leu Asp Thr
            100                 105                 110
Gly Asn Lys Gly Thr Ala Gly Gln Gly His Arg Arg Thr Ser Ala
        115                 120                 125
```

```
Thr Leu Ser Ser Trp Ala Ser Phe Ser Ser Asn Thr Leu Ser Phe
130                 135                 140

Leu Thr Gly Glu Asp Ser Ser Ile Val Ala Pro Val Arg Gly Pro Ala
145                 150                 155                 160

Lys Leu Asp Phe Ser Thr Pro Val His Pro Ala Thr Gln Ala Val Asp
                165                 170                 175

Phe Val Ile Thr Phe Leu Leu Val His Tyr Ile Gln Val Phe Tyr Ser
            180                 185                 190

Leu Val Phe Leu Phe Ile Tyr Leu Val Arg His Gly Tyr Arg Trp Pro
        195                 200                 205

Leu Val Leu Ala Gly Leu Tyr Leu Pro Ser Tyr Phe Ile Pro Phe Gln
210                 215                 220

Arg Leu Gly Gly Trp Pro Phe Arg Leu Leu Met Arg Arg Pro Phe Trp
225                 230                 235                 240

Arg Cys Val Gln Arg Thr Leu Ala Phe Lys Val Glu Arg Glu Val Glu
                245                 250                 255

Leu Ser Pro Ala Thr Gln Tyr Ile Phe Gly Trp His Pro His Gly Ile
                260                 265                 270

Leu Leu Leu Ser Arg Phe Ala Ile Tyr Gly Gly Leu Trp Glu Lys Leu
            275                 280                 285

Phe Pro Gly Val His Phe Lys Thr Leu Ala Ala Ser Pro Leu Phe Trp
    290                 295                 300

Ile Pro Pro Ile Arg Glu Val Ser Ile Leu Leu Gly Gly Val Asp Ala
305                 310                 315                 320

Gly Arg Ala Ser Ala Asn Arg Ala Leu Arg Asp Gly Tyr Ser Val Ser
                325                 330                 335

Leu Tyr Pro Gly Gly Ser Lys Glu Ile Tyr Thr Thr Asn Pro Tyr Thr
                340                 345                 350

Pro Glu Thr Thr Leu Val Leu Lys Ile Arg Lys Gly Phe Ile Arg Met
            355                 360                 365

Ala Leu Arg Tyr Gly Cys Pro Leu Val Pro Val Tyr Thr Phe Gly Glu
        370                 375                 380

Lys Tyr Ala Tyr His Arg Leu Gly His Ala Thr Gly Phe Ala His Trp
385                 390                 395                 400

Leu Leu Ala Val Leu Arg Val Pro Phe Leu Ile Phe Trp Gly Arg Trp
                405                 410                 415

Cys Thr Phe Met Pro Leu Lys His Thr Gln Val Ser Val Val Val Gly
                420                 425                 430

Lys Pro Leu Pro Val Pro Lys Ile Glu Gly Glu Pro Ala Pro Glu Val
            435                 440                 445

Val Glu Glu Trp Leu Gln Arg Tyr Cys Asp Glu Val Gln Ala Leu Phe
450                 455                 460

Gln Arg His Lys His Lys Tyr Ala Arg Pro Glu Glu Phe Val Ala Ile
465                 470                 475                 480

Ser

<210> SEQ ID NO 25
<211> LENGTH: 23
<212> TYPE: DNA
<213> ORGANISM: Artificial Sequence
<220> FEATURE:
<223> OTHER INFORMATION: Primer 2DGAT F1

<400> SEQUENCE: 25
atgactgcct tctttcggcg tag                                         23
```

<210> SEQ ID NO 26
<211> LENGTH: 24
<212> TYPE: DNA
<213> ORGANISM: Artificial Sequence
<220> FEATURE:
<223> OTHER INFORMATION: Primer 2DGAT R1

<400> SEQUENCE: 26
tcacgaaatc gccacgaact cttc                                      24

<210> SEQ ID NO 27
<211> LENGTH: 39
<212> TYPE: DNA
<213> ORGANISM: Artificial Sequence
<220> FEATURE:
<223> OTHER INFORMATION: Primer 2DGAT F2

<400> SEQUENCE: 27
caagcttgcc gccaacatga ctgccttctt tcggcgtag                      39

<210> SEQ ID NO 28
<211> LENGTH: 44
<212> TYPE: DNA
<213> ORGANISM: Artificial Sequence
<220> FEATURE:
<223> OTHER INFORMATION: Primer 2DGAT R2

<400> SEQUENCE: 28
gccccgactc tagaagatct tcacgaaatc gccacgaact cttc                44

<210> SEQ ID NO 29
<211> LENGTH: 61
<212> TYPE: DNA
<213> ORGANISM: Phaeodactylum tricornutum

<400> SEQUENCE: 29
atgttcatga gaattgccgt agcagcactg gccttgctgg ctgctccctc cattcgtgcc   60
g                                                                  61

<210> SEQ ID NO 30
<211> LENGTH: 20
<212> TYPE: PRT
<213> ORGANISM: Phaeodactylum tricornutum

<400> SEQUENCE: 30

Met Phe Met Arg Ile Ala Val Ala Ala Leu Ala Leu Leu Ala Ala Pro
1               5                   10                  15

Ser Ile Arg Ala
            20

<210> SEQ ID NO 31
<211> LENGTH: 18
<212> TYPE: DNA
<213> ORGANISM: Artificial Sequence
<220> FEATURE:
<223> OTHER INFORMATION: Primer 2DGATgeno F2

<400> SEQUENCE: 31
gggagtcgac ctgccttg                                             18

<210> SEQ ID NO 32
<211> LENGTH: 28
<212> TYPE: DNA

```
<213> ORGANISM: Artificial Sequence
<220> FEATURE:
<223> OTHER INFORMATION: Primer 2DGAT geno R2

<400> SEQUENCE: 32
gaagacgaga gagtaaaaga cttggatg                                             28

<210> SEQ ID NO 33
<211> LENGTH: 20
<212> TYPE: DNA
<213> ORGANISM: Artificial Sequence
<220> FEATURE:
<223> OTHER INFORMATION: Primer 7DGAT geno F2

<400> SEQUENCE: 33
catgggatca tgccgcactc                                                      20

<210> SEQ ID NO 34
<211> LENGTH: 25
<212> TYPE: DNA
<213> ORGANISM: Artificial Sequence
<220> FEATURE:
<223> OTHER INFORMATION: Primer 7DGAT geno R2

<400> SEQUENCE: 34 caaataccccc agggcgatag tatag                                               25

<210> SEQ ID NO 35
<211> LENGTH: 1005
<212> TYPE: DNA
<213> ORGANISM: Nannochloropsis gaditana

<400> SEQUENCE: 35
atgaaagatg aggaccgctt gacagtcctg aaaaggcttt cgaagccagt agccgaggcc          60
aagcccggag agctaggttt gggacaaatt gagcacatga cagtctggga ggaaattgtg         120
gccgcaacgt tcttgttgtt tgttgtggga agtatgctgt ggctgcctat agccgtggta         180
attttcgcta tcttcgtacg aagtgcggtg gcatgggcca ctatgacagt ggtcttcgtc         240
gccctgagcc tgcacccccgt tcacgagta cacagcatgg ttcactctcc cttgaactat         300
tttatttttca gtatttctc aatgaagatg gcttccgact atcctatcga tagcaaagga         360
cagtatattt tcgtcgcgcc ccctcacgga gtcttgccct cgggaaacct gctgacggtt         420
catgccatga atcttgtgg agggatggaa ttccgcggtt tgactactga cgtagcttta         480
agacttccta tttttcgaca ctacttaggc ctggttggga ccatcccagc ttcaagacac         540
gtcgcaagga agtacttgga caaaggctgg tcgctaggaa tctccagcgg tggagtcgcg         600
gagattttg aagtcaacaa caacgatgaa gttatcctta tgaaagagcg caaaggattc         660
gtcaaactcg cccttcaaac cgggactccc ctcgtcccgt cctacatctt tggcaacacc         720
aaactcctct cagcgtggta tgatgatgct ggagcccttc aagggatatc ccgctatttc         780
aaatttggga tactgctact ttggggtcgt tttggtcttc ccctcatgca tcggcatccc         840
gtcttagggg tcatggccaa gccaatcgtt gtgccccgtg cggaaggaga acccacgcag         900
gatatgattg acaccattca tgcccaattc tgcgattcac ttatcgcact ctttgacgat         960
tacaagggct tgtatggttg gcctgacaag aaactcctta ttaag                       1005

<210> SEQ ID NO 36
<211> LENGTH: 335
<212> TYPE: PRT
<213> ORGANISM: Nannochloropsis gaditana
```

<400> SEQUENCE: 36

| | | | | | | | | | | | | | | |
|---|---|---|---|---|---|---|---|---|---|---|---|---|---|---|
Met Lys Asp Glu Asp Arg Leu Thr Val Leu Lys Arg Leu Ser Lys Pro
1               5                   10                  15

Val Ala Glu Ala Lys Pro Gly Glu Leu Gly Leu Gly Gln Ile Glu His
            20                  25                  30

Met Thr Val Trp Glu Glu Ile Val Ala Thr Phe Leu Leu Phe Val
        35                  40                  45

Val Gly Ser Met Leu Trp Leu Pro Ile Ala Val Val Ile Phe Ala Ile
50                  55                  60

Phe Val Arg Ser Ala Val Ala Trp Ala Thr Met Thr Val Val Phe Val
65                  70                  75                  80

Ala Leu Ser Leu His Pro Val Ser Arg Val His Ser Met Val His Ser
                85                  90                  95

Pro Leu Asn Tyr Phe Ile Phe Lys Tyr Phe Ser Met Lys Met Ala Ser
                100                 105                 110

Asp Tyr Pro Ile Asp Ser Lys Gly Gln Tyr Ile Phe Val Ala Pro Pro
            115                 120                 125

His Gly Val Leu Pro Phe Gly Asn Leu Leu Thr Val His Ala Met Lys
130                 135                 140

Ser Cys Gly Gly Met Glu Phe Arg Gly Leu Thr Thr Asp Val Ala Leu
145                 150                 155                 160

Arg Leu Pro Ile Phe Arg His Tyr Leu Gly Leu Val Gly Thr Ile Pro
                165                 170                 175

Ala Ser Arg His Val Ala Arg Lys Tyr Leu Asp Lys Gly Trp Ser Leu
            180                 185                 190

Gly Ile Ser Ser Gly Gly Val Ala Glu Ile Phe Glu Val Asn Asn Asn
            195                 200                 205

Asp Glu Val Ile Leu Met Lys Glu Arg Lys Gly Phe Val Lys Leu Ala
            210                 215                 220

Leu Gln Thr Gly Thr Pro Leu Val Pro Ser Tyr Ile Phe Gly Asn Thr
225                 230                 235                 240

Lys Leu Leu Ser Ala Trp Tyr Asp Asp Ala Gly Ala Leu Gln Gly Ile
                245                 250                 255

Ser Arg Tyr Phe Lys Phe Gly Ile Leu Leu Trp Gly Arg Phe Gly
            260                 265                 270

Leu Pro Leu Met His Arg His Pro Val Leu Gly Val Met Ala Lys Pro
            275                 280                 285

Ile Val Val Pro Arg Ala Glu Gly Glu Pro Thr Gln Asp Met Ile Asp
            290                 295                 300

Thr Ile His Ala Gln Phe Cys Asp Ser Leu Ile Ala Leu Phe Asp Asp
305                 310                 315                 320

Tyr Lys Gly Leu Tyr Gly Trp Pro Asp Lys Lys Leu Leu Ile Lys
                325                 330                 335

<210> SEQ ID NO 37
<211> LENGTH: 45
<212> TYPE: DNA
<213> ORGANISM: Artificial Sequence
<220> FEATURE:
<223> OTHER INFORMATION: Primer Ab_AtfA1 _ GLR001_PciI_F

<400> SEQUENCE: 37
agcggccgca agcttgccgc caaatgaaag ccttaagtcc agtgg        45

<210> SEQ ID NO 38
<211> LENGTH: 47
<212> TYPE: DNA
<213> ORGANISM: Artificial Sequence
<220> FEATURE:
<223> OTHER INFORMATION: Primer Ab_AtfA1 _GLR001_PciI_R

<400> SEQUENCE: 38

```
gaccgacgta cctctgagtg acatgctatt tgatcccagc tccaatc        47
```

<210> SEQ ID NO 39
<211> LENGTH: 1374
<212> TYPE: DNA
<213> ORGANISM: Alcanivorax borkumensis

<400> SEQUENCE: 39

```
atgaaagcgc ttagcccagt ggatcaactg ttcctgtggc tggaaaaacg acagcaaccc      60
atgcacgtag gcggtttgca gctgttttcc ttcccggaag gtgccggccc caagtatgtg     120
agtgagctgg cccagcaaat gcgggattac tgccacccag tggcgccatt caaccagcgc     180
ctgacccgtc gactcggcca gtattactgg actagagaca acagttcga tatcgaccac     240
cacttccgcc acgaagcact ccccaaaccc ggtcgcattc gcgaactgct ttctttggtc     300
tccgccgaac attccaacct gctggaccgg gagcgcccca tgtgggaagc ccatttgatc     360
gaagggatcc gcggtcgcca gttcgctctc tattataaga tccaccattc ggtgatggat     420
ggcatatccg ccatgcgtat cgcctccaaa acgctttcca ctgaccccag tgaacgtgaa     480
atggctccgg cttgggcgtt caacaccaaa aaacgctccc gctcactgcc cagcaacccg     540
gttgacatgg cctccagcat ggcgcgccta accgcgagca taagcaaaca agctgccaca     600
gtgcccggtc tcgcgcggga ggtttacaaa gtcacccaaa aagccaaaaa agatgaaaac     660
tatgtgtcta ttttcaggc tcccgacacg attctgaata taccatcac cggttcacgc     720
cgcttttgccg cccagagctt tccattaccg cgcctgaaag ttatcgccaa ggcctataac     780
tgcaccatta acaccgtggt gctctccatg tgtggccacg ctctgcgcga atacttgatt     840
agccaacacg cgctgcccga tgagccactg attgccatgg tgcccatgag cctgcggcag     900
gacgacagca ctggcggcaa ccagatcggt atgatcttgg ctaacctggg cacccacatc     960
tgtgatccag ctaatcgcct gcgcgtcatc cacgattccg tcgaggaagc caaatcccgc    1020
ttctcgcaga tgagcccgga agaaattctc aatttcaccg ccctcaccat ggctcccacc    1080
ggcttgaact tactgaccgg cctagcgcca aaatggcggg ccttcaacgt ggtgatttcc    1140
aacataccccg ggccgaaaga gccgctgtac tggaatggtg cacagctgca aggagtgtat    1200
ccagtatcca ttgccttgga tcgcatcgcc ctaaatatca ccctcaccag ttatgtagac    1260
cagatggaat ttgggcttat cgcctgccgc cgtactctgc cttccatgca gcgactactg    1320
gattacctgg aacagtccat ccgcgaattg gaaatcggtg caggaattaa atag          1374
```

<210> SEQ ID NO 40
<211> LENGTH: 457
<212> TYPE: PRT
<213> ORGANISM: Alcanivorax borkumensis

<400> SEQUENCE: 40

```
Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30
```

-continued

```
Glu Gly Ala Gly Pro Lys Tyr Val Ser Glu Leu Ala Gln Gln Met Arg
             35                  40                  45

Asp Tyr Cys His Pro Val Ala Pro Phe Asn Gln Arg Leu Thr Arg Arg
 50                  55                  60

Leu Gly Gln Tyr Tyr Trp Thr Arg Asp Lys Gln Phe Asp Ile Asp His
 65                  70                  75                  80

His Phe Arg His Glu Ala Leu Pro Lys Pro Gly Arg Ile Arg Glu Leu
                 85                  90                  95

Leu Ser Leu Val Ser Ala Glu His Ser Asn Leu Leu Asp Arg Glu Arg
             100                 105                 110

Pro Met Trp Glu Ala His Leu Ile Glu Gly Ile Arg Gly Arg Gln Phe
             115                 120                 125

Ala Leu Tyr Tyr Lys Ile His His Ser Val Met Asp Gly Ile Ser Ala
130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
             180                 185                 190

Ser Ile Ser Lys Gln Ala Ala Thr Val Pro Gly Leu Ala Arg Glu Val
         195                 200                 205

Tyr Lys Val Thr Gln Lys Ala Lys Lys Asp Glu Asn Tyr Val Ser Ile
         210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Leu Ser Met Cys Gly
                260                 265                 270

His Ala Leu Arg Glu Tyr Leu Ile Ser Gln His Ala Leu Pro Asp Glu
             275                 280                 285

Pro Leu Ile Ala Met Val Pro Met Ser Leu Arg Gln Asp Asp Ser Thr
         290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
             340                 345                 350

Thr Ala Leu Thr Met Ala Pro Thr Gly Leu Asn Leu Leu Thr Gly Leu
         355                 360                 365

Ala Pro Lys Trp Arg Ala Phe Asn Val Val Ile Ser Asn Ile Pro Gly
370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
             420                 425                 430

Leu Pro Ser Met Gln Arg Leu Leu Asp Tyr Leu Glu Gln Ser Ile Arg
         435                 440                 445

Glu Leu Glu Ile Gly Ala Gly Ile Lys
```

<210> SEQ ID NO 41
<211> LENGTH: 47
<212> TYPE: DNA
<213> ORGANISM: Artificial Sequence
<220> FEATURE:
<223> OTHER INFORMATION: Primer Mh_WS1_GLR001_PciI_F

<400> SEQUENCE: 41
agcggccgca agcttgccgc caaatgacgc ccctgaatcc cactgac        47

<210> SEQ ID NO 42
<211> LENGTH: 47
<212> TYPE: DNA
<213> ORGANISM: Artificial Sequence
<220> FEATURE:
<223> OTHER INFORMATION: Mh_WS1_GLR001_PciI_R

<400> SEQUENCE: 42
gaccgacgta cctctgagtg acatgttaca gaccggcgtt gagctcc        47

<210> SEQ ID NO 43
<211> LENGTH: 65
<212> TYPE: DNA
<213> ORGANISM: Artificial Sequence
<220> FEATURE:
<223> OTHER INFORMATION: WS1_416TEF_F

<400> SEQUENCE: 43
tctaatctaa gttttctaga actagtggat cccccgccac catgacgccc ctgaatccca    60
ctgac                                                                65

<210> SEQ ID NO 44
<211> LENGTH: 73
<212> TYPE: DNA
<213> ORGANISM: Artificial Sequence
<220> FEATURE:
<223> OTHER INFORMATION: WS1_416TEF

<400> SEQUENCE: 44
gaggtcgacg gtatcgataa gcttgatatc gaattcctgc agcccttact attacagacc    60
ggcgttgagc tcc                                                       73

<210> SEQ ID NO 45
<211> LENGTH: 1368
<212> TYPE: DNA
<213> ORGANISM: Marinobacter hydrocarbonoclasticus

<400> SEQUENCE: 45
atgacgcccc tgaatcccac tgaccagctc tttctctggc tggaaaaacg ccagcagccc    60
atgcatgtgg gcggcctcca gctgttttcc ttccccgaag gcgcgccgga cgactatgtc   120
gcgcagctgg cagaccagct tcggcagaag acggaggtga ccgccccctt taaccagcgc   180
ctgagctatc gcctgggcca gccggtatgg gtggaggatg agcacctgga ccttgagcat   240
catttccgct tcgaggcgct gcccacaccc gggcgtattc gggagctgct gtcgttcgta   300
tcggcggagc attcgcacct gatggaccgg gagcgcccca tgtgggaggt gcacctgatc   360
gagggcctga agaccggca gtttgcgctc tacaccaagg ttcaccattc cctggtggac   420
ggtgtctcgg ccatgcgcat ggccaccggg atgctgagtg aaaacccgga cgaacacggc   480
atgccgccaa tctgggatct gccttgcctg tcacgggata ggggtgagtc ggacgacac    540

```
tccctctggc gcagtgtcac ccatttgctg gggctttcgg gccgccagct cggcaccatt    600
cccactgtgg caaaggagct actgaaaacc atcaatcagg cccggaagga tccggcctac    660
gactccattt tccatgcccc gcgctgcatg ctgaaccaga aaatcaccgg ttcccgtcgt    720
ttcgccgccc agtcctggtg cctgaaacgg attcgcgccg tgtgcgaggc ctatggcacc    780
acggtcaacg atgtcgtaac tgccatgtgc gcagcggctc tgcgtaccta tctgatgaat    840
caggatgcct tgccggagaa accactggtg gcctttgtgc cggtgtcact acgccgggac    900
gacagctccg ggggcaacca ggtaggcgtc atcctggcga ccttcacac cgatgtgcag    960
gaggccggcg aacgactgtt aaaaatccac catggcatgg aagaggccaa gcagcgctac   1020
cgtcatatga gcccggagga atcgtcaac tacacggccc tgaccctggc gccggccgcc   1080
ttccacctgc tgaccgggct ggcgcccaag tggcagacct tcaatgtggt gatttccaat   1140
gtccccgggc catccaggcc cctgtactgg aacggggcga actggaagg catgtatccg   1200
gtgtctatcg atatggacag actggccctg aacatgacac tgaccagcta taacgaccag   1260
gtggagttcg gcctgattgg ctgtcgccgg accctgccca gcctgcaacg gatgctggac   1320
tacctggaac agggtctggc agagctggag ctcaacgccg gtctgtaa              1368
```

<210> SEQ ID NO 46
<211> LENGTH: 455
<212> TYPE: PRT
<213> ORGANISM: Marinobacter hydrocarbonoclasticus

<400> SEQUENCE: 46

```
Met Thr Pro Leu Asn Pro Thr Asp Gln Leu Phe Leu Trp Leu Glu Lys
1               5                  10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Gly Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220
```

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
            245                 250                 255

Ala Tyr Gly Thr Thr Val Asn Asp Val Val Thr Ala Met Cys Ala Ala
        260                 265                 270

Ala Leu Arg Thr Tyr Leu Met Asn Gln Asp Ala Leu Pro Glu Lys Pro
    275                 280                 285

Leu Val Ala Phe Val Pro Val Ser Leu Arg Arg Asp Asp Ser Ser Gly
290                 295                 300

Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Ala
            325                 330                 335

Lys Gln Arg Tyr Arg His Met Ser Pro Glu Glu Ile Val Asn Tyr Thr
                340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
                420                 425                 430

Pro Ser Leu Gln Arg Met Leu Asp Tyr Leu Glu Gln Gly Leu Ala Glu
            435                 440                 445

Leu Glu Leu Asn Ala Gly Leu
    450                 455

<210> SEQ ID NO 47
<211> LENGTH: 41
<212> TYPE: DNA
<213> ORGANISM: Artificial Sequence
<220> FEATURE:
<223> OTHER INFORMATION: Primer Ms_WS_DGAT _GLR001_PciI_F

<400> SEQUENCE: 47
agcggccgca agcttgccgc caaatgaacc gcatgcaact c                    41

<210> SEQ ID NO 48
<211> LENGTH: 46
<212> TYPE: DNA
<213> ORGANISM: Artificial Sequence
<220> FEATURE:
<223> OTHER INFORMATION: Ms_WS_DGAT _GLR001_PciI_R

<400> SEQUENCE: 48
gaccgacgta cctctgagtg acatgttaag cgccagtggc ggtttc              46

<210> SEQ ID NO 49
<211> LENGTH: 1374
<212> TYPE: DNA
<213> ORGANISM: Mycobacterium smegmatis

<400> SEQUENCE: 49
atgaaccgga tgcagctcat gtcgccgacc gattccatgt tcttgatcgc ggagtcgcgg     60

-continued

| | |
|---|---|
| gagcacccga tgcatgtggg cggtctggcg ctgtacgacc cgcccgacga tgcaggcccg | 120 |
| gagttcgtgc gtgagttgta cgaagagatg gtcaggcaca ccgacttcca gccggtgttc | 180 |
| cgcaagcatc cggcgaccct gctcgggggt atcgccaacg tgggctggac tctcgacgac | 240 |
| gaggtcgacc tcgactacca cctgcggcgt tcggcgctgc cgtcgccggg acgcccgcgc | 300 |
| gagcttctcg aactgacctc acgtgtgcac ggcacgctgc tcgaccggca tcgcccgctg | 360 |
| tgggaggcct acctcatcga gggtatggcc gacggacgct tcgcggtgta caccaaggtg | 420 |
| caccactcgc tgatcgacgg ggtgtcggcg atgaagctcg tcgaacgcac actgtccgag | 480 |
| gacccgagcg acaccacggt ccgggtgccg tggaacctgc gcggcgcga atcgtcgcgc | 540 |
| agggcgggct cgtcgtcgtt ggcgcgcacc gcgaccggcg ccgcgacgtc actggcggcg | 600 |
| ctggcgccgt cgacgatcag gctggcgcgt gcggcgctgc tcgaacagca gctcacgttg | 660 |
| ccgttcggtg cgccaaggac catgttcaac gtcaagatcg gcggggcccg ccgcgtcgcg | 720 |
| gcgcagtcgt ggccgctgga gcggttgcgt cgcatcaagg cggtcaccgg gcaacgatc | 780 |
| aacgacatcg tgctcgcgat gtgtgcgggt gcgctgcgcg cctatctcgc cgagcaggac | 840 |
| gcgctgccgg accggccgct gatcgcgatg gtgccggtga gcatgcgcag tgaacacgag | 900 |
| gccgacgccg cggcaacat ggtcggctcg atcctgtgca gcctgggcac cgacgtggag | 960 |
| gatccggccg accggctcgc ggtgatccgc cgctcgatca ccgacaacaa gagggtgttc | 1020 |
| tccgaactgc cgcgcctgca ggcgctcgcg ttgtcggcgc tgctgatcgc cccgctcggg | 1080 |
| ctcaccacgg cgttccccgg attcgtcgac gccaccgcgc cgccgttcaa cctcgtgatc | 1140 |
| tccaacgtgc cgggacccaa gaagccgctg tactggcgtg ggcccgcct ggcgggcaac | 1200 |
| tacccgctgt cgatcgcgct ggacgggcag gccctcaaca tgaccgtggt gagcaacgcc | 1260 |
| cacaacctgg atttcgggtt ggtgggctgc cggcgcagcg tgccgcatct gcagcggctg | 1320 |
| ctgggccacc tggagaccct gctgaaagac ctcgagacgg ccacaggcgc ctga | 1374 |

<210> SEQ ID NO 50
<211> LENGTH: 457
<212> TYPE: PRT
<213> ORGANISM: Mycobacterium smegmatis

<400> SEQUENCE: 50

```
Met Asn Arg Met Gln Leu Met Ser Pro Thr Asp Ser Met Phe Leu Ile
1               5                   10                  15

Ala Glu Ser Arg Glu His Pro Met His Val Gly Gly Leu Ala Leu Tyr
            20                  25                  30

Asp Pro Pro Asp Asp Ala Gly Pro Glu Phe Val Arg Glu Leu Tyr Glu
        35                  40                  45

Glu Met Val Arg His Thr Asp Phe Gln Pro Val Phe Arg Lys His Pro
    50                  55                  60

Ala Thr Leu Leu Gly Gly Ile Ala Asn Val Gly Trp Thr Leu Asp Asp
65                  70                  75                  80

Glu Val Asp Leu Asp Tyr His Leu Arg Arg Ser Ala Leu Pro Ser Pro
                85                  90                  95

Gly Arg Pro Arg Glu Leu Leu Glu Leu Thr Ser Arg Val His Gly Thr
            100                 105                 110

Leu Leu Asp Arg His Arg Pro Leu Trp Glu Ala Tyr Leu Ile Glu Gly
        115                 120                 125

Met Ala Asp Gly Arg Phe Ala Val Tyr Thr Lys Val His His Ser Leu
    130                 135                 140
```

-continued

Ile Asp Gly Val Ser Ala Met Lys Leu Val Glu Arg Thr Leu Ser Glu
145                 150                 155                 160

Asp Pro Ser Asp Thr Thr Val Arg Val Pro Trp Asn Leu Pro Arg Arg
            165                 170                 175

Glu Ser Ser Arg Arg Ala Gly Ser Ser Ser Leu Ala Arg Thr Ala Thr
        180                 185                 190

Gly Ala Ala Thr Ser Leu Ala Ala Leu Ala Pro Ser Thr Ile Arg Leu
    195                 200                 205

Ala Arg Ala Ala Leu Leu Glu Gln Gln Leu Thr Leu Pro Phe Gly Ala
210                 215                 220

Pro Arg Thr Met Phe Asn Val Lys Ile Gly Gly Ala Arg Arg Val Ala
225                 230                 235                 240

Ala Gln Ser Trp Pro Leu Glu Arg Leu Arg Arg Ile Lys Ala Val Thr
            245                 250                 255

Gly Ala Thr Ile Asn Asp Ile Val Leu Ala Met Cys Ala Gly Ala Leu
        260                 265                 270

Arg Ala Tyr Leu Ala Glu Gln Asp Ala Leu Pro Asp Arg Pro Leu Ile
    275                 280                 285

Ala Met Val Pro Val Ser Met Arg Ser Glu His Glu Ala Asp Ala Gly
290                 295                 300

Gly Asn Met Val Gly Ser Ile Leu Cys Ser Leu Gly Thr Asp Val Glu
305                 310                 315                 320

Asp Pro Ala Asp Arg Leu Ala Val Ile Arg Arg Ser Ile Thr Asp Asn
            325                 330                 335

Lys Arg Val Phe Ser Glu Leu Pro Arg Leu Gln Ala Leu Ala Leu Ser
        340                 345                 350

Ala Leu Leu Ile Ala Pro Leu Gly Leu Thr Thr Ala Phe Pro Gly Phe
    355                 360                 365

Val Asp Ala Thr Ala Pro Pro Phe Asn Leu Val Ile Ser Asn Val Pro
370                 375                 380

Gly Pro Lys Lys Pro Leu Tyr Trp Arg Gly Ala Arg Leu Ala Gly Asn
385                 390                 395                 400

Tyr Pro Leu Ser Ile Ala Leu Asp Gly Gln Ala Leu Asn Met Thr Val
            405                 410                 415

Val Ser Asn Ala His Asn Leu Asp Phe Gly Leu Val Gly Cys Arg Arg
        420                 425                 430

Ser Val Pro His Leu Gln Arg Leu Leu Gly His Leu Glu Thr Ser Leu
    435                 440                 445

Lys Asp Leu Glu Thr Ala Thr Gly Ala
450                 455

<210> SEQ ID NO 51
<211> LENGTH: 65
<212> TYPE: DNA
<213> ORGANISM: Artificial Sequence
<220> FEATURE:
<223> OTHER INFORMATION: Primer Ro_Atf1_416TEF_F

<400> SEQUENCE: 51
tctaatctaa gttttctaga actagtggat cccccgccac catgacccag acggacttca    60
tgtcg                                                                65

<210> SEQ ID NO 52
<211> LENGTH: 70
<212> TYPE: DNA
<213> ORGANISM: Artificial Sequence

```
<220> FEATURE:
<223> OTHER INFORMATION: Primer Ro_Atf1_416TEF_R

<400> SEQUENCE: 52
gaggtcgacg gtatcgataa gcttgatatc gaattcctgc agcccttact atcacgaggc    60
cacgaccacc                                                          70

<210> SEQ ID NO 53
<211> LENGTH: 44
<212> TYPE: DNA
<213> ORGANISM: Artificial Sequence
<220> FEATURE:
<223> OTHER INFORMATION: Primer Ro_Atf1_GLR001_PciI_F

<400> SEQUENCE: 53
agcggccgca agcttgccgc caaatgaccc agacggactt catg                    44

<210> SEQ ID NO 54
<211> LENGTH: 47
<212> TYPE: DNA
<213> ORGANISM: Artificial Sequence
<220> FEATURE:
<223> OTHER INFORMATION: Primer Ro_Atf1_GLR001_PciI_R

<400> SEQUENCE: 54
gaccgacgta cctctgagtg acatgtcacg aggccacgac caccctc                 47

<210> SEQ ID NO 55
<211> LENGTH: 1386
<212> TYPE: DNA
<213> ORGANISM: Rhodococcus opacus

<400> SEQUENCE: 55
atgaatcgag tggccatgag cggcgcaacc gagcgatcga tgacgcagac cgacctgatg    60
tcttggcgga tggaggccga tccggtcctc cgctcgacaa tcgtctcgat catcgtgctg   120
gacaggctcc cggatcacga acgattgacc gccgcgatga accacgccat cgacgtagtt   180
ccgatcttca ggtgcaaagc ggttgcgcga caatttccgt ggagtccacc actttgggtg   240
gatgacgcgg acttcgacct gagttggcac cttcgaaggt cttccgtgcc accaccaggt   300
gggtggaaag gcgtcctgga ttttgcccgc atgagcggga tggcagcctt cgacaaagat   360
cgtccgttat gggagctcac cgtgctcgat ggctaggcg gcggtgcaac agcgatggta   420
gtcaaagttc atcattcctt gaccgacggg gtcgggggta tgcaactgac acgcgaaatt   480
gccgatgaca cgcgggctgg cggatcaagt caggacggcc acgaattcag gccacctgtt   540
gttcgttcca caccaggaga ctcacgtgcg gcgatggccg aagcggtggc ccgacgtgcc   600
gcgcacgcag tgcgccatcc cgcagctacg atgcacgacg tcgtgcgaat cttcggatcg   660
acggcgcgta tgacgcgacc ggcgacccga cgatgtcgc cagtgatgac tgctcggagt   720
acgcgccgtg gtttcggtgt gatcgaattt ccggtggcgg cactgaccgc tgcagcggcg   780
ggcacacaat gctcggtaaa cgacgcgttc ttggctgcac ttctactggg catggccggc   840
taccacagag gccacggtga cgtaccgaat caactgatgg tgacattgcc gatcagtctg   900
cgtgacagtc gtgatccgct gggaggcaac cgaatcacgc ttgcaaggtt tgctcttccg   960
gtcgatattg cagatccgga gaaattgatc cgtcgtgttc acgtcatcgt agaaagttgg  1020
cggaacgagc cggcgattcc gctatctcct cacttggcca gaatgcttaa cttgctgccg  1080
gtcgcggtca caggcgacat gctcaagcac atggattttg ttgcatccaa cgtcgttggt  1140
```

```
tcttcgacac cgttgtacct cgccggtgcg cggataattc gccaattcgc attcagtcct    1200
accctcggat cggctttcaa cgcgactttg atgtcttacg cctcgcacgt gtgtgtcggg    1260
atcaacgtcg acgtgagagc agttccggac caacccgcat tgatgacagc cgtctccgaa    1320
gggtttagag ccgtgctggc acttgggact cggcacacag acgccacggt gacaacgtcg    1380
tactga                                                                1386
```

<210> SEQ ID NO 56
<211> LENGTH: 461
<212> TYPE: PRT
<213> ORGANISM: Rhodococcus opacus

<400> SEQUENCE: 56

```
Met Asn Arg Val Ala Met Ser Gly Ala Thr Glu Arg Ser Met Thr Gln
1               5                   10                  15

Thr Asp Leu Met Ser Trp Arg Met Glu Ala Asp Pro Val Leu Arg Ser
            20                  25                  30

Thr Ile Val Ser Ile Ile Val Leu Asp Arg Leu Pro Asp His Glu Arg
        35                  40                  45

Leu Thr Ala Ala Met Asn His Ala Ile Asp Val Val Pro Ile Phe Arg
    50                  55                  60

Cys Lys Ala Val Ala Arg Gln Phe Pro Trp Ser Pro Pro Leu Trp Val
65                  70                  75                  80

Asp Asp Ala Asp Phe Asp Leu Ser Trp His Leu Arg Arg Ser Ser Val
                85                  90                  95

Pro Pro Pro Gly Gly Trp Lys Gly Val Leu Asp Phe Ala Arg Met Ser
            100                 105                 110

Gly Met Ala Ala Phe Asp Lys Asp Arg Pro Leu Trp Glu Leu Thr Val
        115                 120                 125

Leu Asp Gly Leu Gly Gly Gly Ala Thr Ala Met Val Val Lys Val His
    130                 135                 140

His Ser Leu Thr Asp Gly Val Gly Gly Met Gln Leu Thr Arg Glu Ile
145                 150                 155                 160

Ala Asp Asp Thr Arg Ala Gly Gly Ser Ser Gln Asp Gly His Glu Phe
                165                 170                 175

Arg Pro Pro Val Val Arg Ser Thr Pro Gly Asp Ser Arg Ala Ala Met
            180                 185                 190

Ala Glu Ala Val Ala Arg Arg Ala His Ala Val Arg His Pro Ala
        195                 200                 205

Ala Thr Met His Asp Val Val Arg Ile Phe Gly Ser Thr Ala Arg Met
    210                 215                 220

Thr Arg Pro Ala Thr Arg Thr Met Ser Pro Val Met Thr Ala Arg Ser
225                 230                 235                 240

Thr Arg Arg Gly Phe Gly Val Ile Glu Phe Pro Val Ala Ala Leu Thr
                245                 250                 255

Ala Ala Ala Ala Gly Thr Gln Cys Ser Val Asn Asp Ala Phe Leu Ala
            260                 265                 270

Ala Leu Leu Leu Gly Met Ala Gly Tyr His Arg Gly His Gly Asp Val
        275                 280                 285

Pro Asn Gln Leu Met Val Thr Leu Pro Ile Ser Leu Arg Asp Ser Arg
    290                 295                 300

Asp Pro Leu Gly Gly Asn Arg Ile Thr Leu Ala Arg Phe Ala Leu Pro
305                 310                 315                 320

Val Asp Ile Ala Asp Pro Glu Lys Leu Ile Arg Arg Val His Val Ile
```

```
              325                 330                 335
Val Glu Ser Trp Arg Asn Glu Pro Ala Ile Pro Leu Ser Pro His Leu
            340                 345                 350

Ala Arg Met Leu Asn Leu Leu Pro Val Ala Val Thr Gly Asp Met Leu
            355                 360                 365

Lys His Met Asp Phe Val Ala Ser Asn Val Val Gly Ser Ser Thr Pro
        370                 375                 380

Leu Tyr Leu Ala Gly Ala Arg Ile Ile Arg Gln Phe Ala Phe Ser Pro
385                 390                 395                 400

Thr Leu Gly Ser Ala Phe Asn Ala Thr Leu Met Ser Tyr Ala Ser His
                405                 410                 415

Val Cys Val Gly Ile Asn Val Asp Val Arg Ala Val Pro Asp Gln Pro
                420                 425                 430

Ala Leu Met Thr Ala Val Ser Glu Gly Phe Arg Ala Val Leu Ala Leu
            435                 440                 445

Gly Thr Arg His Thr Asp Ala Thr Val Thr Thr Ser Tyr
450                 455                 460
```

<210> SEQ ID NO 57
<211> LENGTH: 44
<212> TYPE: DNA
<213> ORGANISM: Artificial Sequence
<220> FEATURE:
<223> OTHER INFORMATION: Primer DGAT10_GLR001_PciI_F

<400> SEQUENCE: 57
agcggccgca agcttgccgc caaatggaag atgaggaccg cttg        44

<210> SEQ ID NO 58
<211> LENGTH: 55
<212> TYPE: DNA
<213> ORGANISM: Artificial Sequence
<220> FEATURE:
<223> OTHER INFORMATION: Primer DGAT10_GLR001_PciI_R

<400> SEQUENCE: 58
gaccgacgta cctctgagtg acatgttact acttaataag gagtttcttg tcagg        55

<210> SEQ ID NO 59
<211> LENGTH: 62
<212> TYPE: DNA
<213> ORGANISM: Artificial Sequence
<220> FEATURE:
<223> OTHER INFORMATION: Primer DGAT10_416TEF_F

<400> SEQUENCE: 59
tctaatctaa gttttctaga actagtggat cccccgccac catggaagat gaggaccgct        60
tg        62

<210> SEQ ID NO 60
<211> LENGTH: 78
<212> TYPE: DNA
<213> ORGANISM: Artificial Sequence
<220> FEATURE:
<223> OTHER INFORMATION: Primer EH_DGAT10_416TEF_R

<400> SEQUENCE: 60
gaggtcgacg gtatcgataa gcttgatatc gaattcctgc agcccttact actacttaat        60
aaggagtttc ttgtcagg        78

```
<210> SEQ ID NO 61
<211> LENGTH: 51
<212> TYPE: DNA
<213> ORGANISM: Artificial Sequence
<220> FEATURE:
<223> OTHER INFORMATION: Primer DGAT2_GLR001_PciI_F

<400> SEQUENCE: 61
agcggccgca agcttgccgc caaatggctg ccttctttcg gcgtaggaat g        51

<210> SEQ ID NO 62
<211> LENGTH: 57
<212> TYPE: DNA
<213> ORGANISM: Artificial Sequence
<220> FEATURE:
<223> OTHER INFORMATION: Primer DGAT2_GLR001_PciI_R

<400> SEQUENCE: 62
gaccgacgta cctctgagtg acatgctacg aaatcgccac gaactcttcc gggcgtg    57

<210> SEQ ID NO 63
<211> LENGTH: 49
<212> TYPE: DNA
<213> ORGANISM: Artificial Sequence
<220> FEATURE:
<223> OTHER INFORMATION: Primer DGAT7__GLR001_PciI_F

<400> SEQUENCE: 63
agcggccgca agcttgccgc caaatggtgc ttggggaggg caaaaaaac            49

<210> SEQ ID NO 64
<211> LENGTH: 49
<212> TYPE: DNA
<213> ORGANISM: Artificial Sequence
<220> FEATURE:
<223> OTHER INFORMATION: Primer DGAT7__GLR001_PciI_R

<400> SEQUENCE: 64
gaccgacgta cctctgagtg acatgctaaa acagatgcag ctcccggtc            49

<210> SEQ ID NO 65
<211> LENGTH: 40
<212> TYPE: DNA
<213> ORGANISM: Artificial Sequence
<220> FEATURE:
<223> OTHER INFORMATION: Primer M002

<400> SEQUENCE: 65
cgactctaga agatctttat tcattagtac tttcctgatt                      40

<210> SEQ ID NO 66
<211> LENGTH: 37
<212> TYPE: DNA
<213> ORGANISM: Artificial Sequence
<220> FEATURE:
<223> OTHER INFORMATION: Primer M004

<400> SEQUENCE: 66
tcttgatgag catccatcat ccacggcagc ggcagca                         37

<210> SEQ ID NO 67
<211> LENGTH: 40
<212> TYPE: DNA
<213> ORGANISM: Artificial Sequence
<220> FEATURE:
<223> OTHER INFORMATION: Primer M005
```

<400> SEQUENCE: 67
tcttgatgag catccatcat gatcccaaaa agccacaaag                                40

<210> SEQ ID NO 68
<211> LENGTH: 38
<212> TYPE: DNA
<213> ORGANISM: Artificial Sequence
<220> FEATURE:
<223> OTHER INFORMATION: Primer M006

<400> SEQUENCE: 68
tgctgccgct gccgtggatg atggatgctc atcaagaa                                  38

<210> SEQ ID NO 69
<211> LENGTH: 40
<212> TYPE: DNA
<213> ORGANISM: Artificial Sequence
<220> FEATURE:
<223> OTHER INFORMATION: Primer M007

<400> SEQUENCE: 69
ctttgtggct ttttgggatc atgatggatg ctcatcaaga                                40

<210> SEQ ID NO 70
<211> LENGTH: 36
<212> TYPE: DNA
<213> ORGANISM: Artificial Sequence
<220> FEATURE:
<223> OTHER INFORMATION: Primer M008

<400> SEQUENCE: 70
cgactctaga agatcttcaa tttccacaca caaacc                                    36

<210> SEQ ID NO 71
<211> LENGTH: 33
<212> TYPE: DNA
<213> ORGANISM: Artificial Sequence
<220> FEATURE:
<223> OTHER INFORMATION: Primer M009

<400> SEQUENCE: 71
gcttgccgcc aacatggagg tttcaggcgc cgt                                       33

<210> SEQ ID NO 72
<211> LENGTH: 36
<212> TYPE: DNA
<213> ORGANISM: Artificial Sequence
<220> FEATURE:
<223> OTHER INFORMATION: Primer M0010

<400> SEQUENCE: 72
gcttgccgcc aacatgagac tattggtact tggtct                                    36

<210> SEQ ID NO 73
<211> LENGTH: 402
<212> TYPE: DNA
<213> ORGANISM: Nannochloropsis gaditana

<400> SEQUENCE: 73
atgagactat tggtacttgg tctcgtgtcc ctcggggtca cgggctttgc ccacacgcac           60
cctcgtctgt tgtccaagat tccgggagcc agtctcaaag gacgcccctg tttcgcggag          120
cccccctctg gtcctacctc ccgctccttc tctctgcctc ggagccgaac cgcggctctt          180
acatccgtag agccgagtgt gtataatttg caacctaccc cggttgtagc gccgaaactt          240
ttggtcagca gacgcggggg agcagttgcg acagctactg gatcagatgc tggagtcaag    300
cagaccttga aagtgggctc tttcttcttt ctttggtatt tgttcaacat cggctacaat    360
atctataaca agaaagccct caatgtgctg ccgctgccgt gg    402

<210> SEQ ID NO 74
<211> LENGTH: 134
<212> TYPE: PRT
<213> ORGANISM: Nannochloropsis gaditana

<400> SEQUENCE: 74

Met Arg Leu Leu Val Leu Gly Leu Val Ser Leu Gly Val Thr Gly Phe
1               5                  10                  15

Ala His Thr His Pro Arg Leu Leu Ser Lys Ile Pro Gly Ala Ser Leu
            20                  25                  30

Lys Gly Arg Pro Cys Phe Ala Glu Pro Pro Ser Gly Pro Thr Ser Arg
        35                  40                  45

Ser Phe Ser Leu Pro Arg Ser Arg Thr Ala Ala Leu Thr Ser Val Glu
    50                  55                  60

Pro Ser Val Tyr Asn Leu Gln Pro Thr Pro Val Val Ala Pro Lys Leu
65                  70                  75                  80

Leu Val Ser Arg Arg Gly Gly Ala Val Ala Thr Ala Thr Gly Ser Asp
                85                  90                  95

Ala Gly Val Lys Gln Thr Leu Lys Val Gly Ser Phe Phe Phe Leu Trp
            100                 105                 110

Tyr Leu Phe Asn Ile Gly Tyr Asn Ile Tyr Asn Lys Lys Ala Leu Asn
        115                 120                 125

Val Leu Pro Leu Pro Trp
    130

<210> SEQ ID NO 75
<211> LENGTH: 468
<212> TYPE: DNA
<213> ORGANISM: Nannochloropsis gaditana

<400> SEQUENCE: 75
atgagactat tggtacttgg tctcgtgtcc ctcggggtca cgggctttgc ccacacgcac    60
cctcgtctgt tgtccaagat tccgggagcc agtctcaaag gacgcccctg tttcgcggag    120 ccccctctg gtcctacctc ccgctccttc tctctgcctc ggagccgaac gcggctctt    180 acatccgtag agccgagtgt gtataatttg caacctaccc cggttgtagc gccgaaactt    240
ttggtcagca gacgcggggg agcagttgcg acagctactg gatcagatgc tggagtcaag    300
cagaccttga aagtgggctc tttcttcttt ctttggtatt tgttcaacat cggctacaat    360
atctataaca agaaagccct caatgtgctg ccgctgccgt ggatggtggg tttggtccag    420
ctctctctcg gcttgcttta tgtcttccct tgtggctttt tgggatc    468

<210> SEQ ID NO 76
<211> LENGTH: 156
<212> TYPE: PRT
<213> ORGANISM: Nannochloropsis gaditana

<400> SEQUENCE: 76

Met Arg Leu Leu Val Leu Gly Leu Val Ser Leu Gly Val Thr Gly Phe
1               5                  10                  15

Ala His Thr His Pro Arg Leu Leu Ser Lys Ile Pro Gly Ala Ser Leu
            20                  25                  30

```
Lys Gly Arg Pro Cys Phe Ala Glu Pro Pro Ser Gly Pro Thr Ser Arg
        35                  40                  45

Ser Phe Ser Leu Pro Arg Ser Arg Thr Ala Ala Leu Thr Ser Val Glu
    50                  55                  60

Pro Ser Val Tyr Asn Leu Gln Pro Thr Pro Val Val Ala Pro Lys Leu
65                  70                  75                  80

Leu Val Ser Arg Arg Gly Gly Ala Val Ala Thr Ala Thr Gly Ser Asp
                85                  90                  95

Ala Gly Val Lys Gln Thr Leu Lys Val Gly Ser Phe Phe Phe Leu Trp
            100                 105                 110

Tyr Leu Phe Asn Ile Gly Tyr Asn Ile Tyr Asn Lys Lys Ala Leu Asn
                115                 120                 125

Val Leu Pro Leu Pro Trp Met Val Gly Leu Val Gln Leu Ser Leu Gly
            130                 135                 140

Leu Leu Tyr Val Phe Pro Leu Trp Leu Phe Gly Ile
145                 150                 155
```

<210> SEQ ID NO 77
<211> LENGTH: 1092
<212> TYPE: DNA
<213> ORGANISM: Euonymus alatus

<400> SEQUENCE: 77

| | | | | | |
|---|---|---|---|---|---|
| atgatggatg | ctcatcaaga | gatcaagaac | ttcatcaagg | tttgggtaca | agccatggta | 60 |
| tgtctatctt | acgcttacta | cttctcctca | agacttccaa | aaggactctt | aaggttactc | 120 |
| tctttacttc | ctgtccttta | tctcctatta | atcgctccct | gaacatctc | ttctttcatt | 180 |
| ctttcatcaa | tcaccggctt | cttccttgct | tggctaacaa | cattcaaggt | catctctttt | 240 |
| gcctttgatc | aaggcccttt | gtatccactc | ccacaaaacc | tcctacattt | catctcaata | 300 |
| gcttgtcttc | ccatcacaat | caagcgaaac | ccatcaccaa | aattgaaatc | cacaacaaac | 360 |
| ccatctccaa | tttcacatct | tttgaaaaag | gcattcatgt | catttccatc | taaagtcttg | 420 |
| ttccattggg | tcattgctca | tctctaccaa | tacaaaaagt | acatggatcc | aaacgtggtc | 480 |
| ttagtgatct | attgttgtca | tgtgtacgtt | atgttggata | tctcactctc | tctatgtgca | 540 |
| accctagctg | aattcctttg | tgggtttgat | gttgaaccac | aattcaaaga | gccttacctt | 600 |
| gctacttcac | tacaagactt | tggggccgt | aggtggaaca | taattgtgtc | aagtgtccta | 660 |
| cgttcgactg | tctatgcccc | aactagaaac | attgcttcat | atctaattgg | gtctagatgg | 720 |
| gcttattttc | cagctataat | tgcaacattt | gtcgtatcag | gagttatgca | tgatgtagtg | 780 |
| tactatgtgt | acatgatgca | tatgtatccc | aagtgggata | tgacagggca | cttcgtccta | 840 |
| catgggattt | gtgaagcttt | ggaggtggag | atgaagtgta | agagatcaag | gagtgacaag | 900 |
| tggcggcggc | atccagctgt | cgattgggta | atggtgatgg | ggtttgtgat | ggggactagt | 960 |
| gtttccttac | tctttgtgcc | actattaagg | gataatgtgg | accaaattgt | agcagaagag | 1020 |
| tactcaattt | tgtttaattt | tgtgagggag | aagattgtca | tgcttggaac | aaggtttgtg | 1080 |
| tgtggaaatt | ga | | | | | 1092 |

<210> SEQ ID NO 78
<211> LENGTH: 363
<212> TYPE: PRT
<213> ORGANISM: Euonymus alatus

<400> SEQUENCE: 78

Met Met Asp Ala His Gln Glu Ile Lys Asn Phe Ile Lys Val Trp Val
1               5                   10                  15

Gln Ala Met Val Cys Leu Ser Tyr Ala Tyr Tyr Phe Ser Ser Arg Leu
            20                  25                  30

Pro Lys Gly Leu Leu Arg Leu Leu Ser Leu Leu Pro Val Leu Tyr Leu
        35                  40                  45

Leu Leu Ile Ala Pro Leu Asn Ile Ser Ser Phe Ile Leu Ser Ser Ile
50                  55                  60

Thr Gly Phe Phe Leu Ala Trp Leu Thr Thr Phe Lys Val Ile Ser Phe
65                  70                  75                  80

Ala Phe Asp Gln Gly Pro Leu Tyr Pro Leu Pro Gln Asn Leu Leu His
                85                  90                  95

Phe Ile Ser Ile Ala Cys Leu Pro Ile Thr Ile Lys Arg Asn Pro Ser
                100                 105                 110

Pro Lys Leu Lys Ser Thr Thr Asn Pro Ser Pro Ile Ser His Leu Leu
        115                 120                 125

Lys Lys Ala Phe Met Ser Phe Pro Ser Lys Val Leu Phe His Trp Val
130                 135                 140

Ile Ala His Leu Tyr Gln Tyr Lys Lys Tyr Met Asp Pro Asn Val Val
145                 150                 155                 160

Leu Val Ile Tyr Cys Cys His Val Tyr Val Met Leu Asp Ile Ser Leu
                165                 170                 175

Ser Leu Cys Ala Thr Leu Ala Glu Phe Leu Cys Gly Phe Asp Val Glu
                180                 185                 190

Pro Gln Phe Lys Glu Pro Tyr Leu Ala Thr Ser Leu Gln Asp Phe Trp
            195                 200                 205

Gly Arg Arg Trp Asn Ile Ile Val Ser Ser Val Leu Arg Ser Thr Val
210                 215                 220

Tyr Ala Pro Thr Arg Asn Ile Ala Ser Tyr Leu Ile Gly Ser Arg Trp
225                 230                 235                 240

Ala Tyr Phe Pro Ala Ile Ile Ala Thr Phe Val Val Ser Gly Val Met
                245                 250                 255

His Asp Val Val Tyr Tyr Val Tyr Met Met His Met Tyr Pro Lys Trp
            260                 265                 270

Asp Met Thr Gly His Phe Val Leu His Gly Ile Cys Glu Ala Leu Glu
        275                 280                 285

Val Glu Met Lys Cys Lys Arg Ser Arg Ser Asp Lys Trp Arg Arg His
290                 295                 300

Pro Ala Val Asp Trp Val Met Val Met Gly Phe Val Met Gly Thr Ser
305                 310                 315                 320

Val Ser Leu Leu Phe Val Pro Leu Leu Arg Asp Asn Val Asp Gln Ile
                325                 330                 335

Val Ala Glu Glu Tyr Ser Ile Leu Phe Asn Phe Val Arg Glu Lys Ile
            340                 345                 350

Val Met Leu Gly Thr Arg Phe Val Cys Gly Asn
            355                 360

<210> SEQ ID NO 79
<211> LENGTH: 1637
<212> TYPE: DNA
<213> ORGANISM: Arachis hypogaea

<400> SEQUENCE: 79
aatgaacttg acataaagtg gttgtttgta acaccccatt tagtgttttg cttagatgtt        60

```
gagagttcta taaactttttg tactatttgg taccccgtaa ttaatagaaa tagaaatgtg    120
ataatggttc tatgtttcat tccagaaaaa aattgtcatt ttaaaaagtt ttcttaaatt    180
ctgaatggga atgatgatca ttcagatcaa taaggttaac acttttttat atgatatttt    240
atgtaatctg attaattttt ttttggtgac aaaaaactcg tgccgaattc ggcacgaggt    300
caaaacctca gaagagagaa aaggagaatt tggttcctaa ttaattctca ccatcaacga    360
tggaggtttc aggcgccgtt ctaaggaatg tcacgtgccc ttccttttct gtgcacgtga    420
gttcccgtcg tcgtggtggt gatagttgtg ttacagtgcc ggtgaggatg agaaaaaagg    480
cggtggtgcg ttgttgctgc gggttcagtg attcggggca tgtgcagtat tacggggacg    540
agaagaagaa ggagaatgga accgctatgt tgagcaccaa gaagaagctc aagatgctga    600
agaaacgtgt ccttttcgat gatcttcaag gaaacctgac ttgggatgct gctatggttt    660
tgatgaagca gctagagcaa gtaagggcag aggagaagga attgaagaaa aaaggaagc    720 aagagaagaa ggaggcaaaa ctcaaagcct ctaagatgaa caccaatcct gattgcgaat    780
cgtcatcgtc atcgtcatca tctgaatctg aatctgaatc aagtgagagt gaatgtgaca    840
atgaggtggt tgacatgaag aagaacatta aggttggtgt tgccgttgct gttgccgatt    900
ccccacgaaa ggcggaaacc atgattctat acacctccct tgttgcccga gatgttagtg    960
ctaatcatca tcatcataat gccgtggaat tattctctag aaacaatgac atatcagttg   1020
gaagcattaa tggtggcctt aagaatgaga atactgcggt tattaccact gaagctattc   1080
ctcagaagag gattgaggta tgcatgggaa acaagtgcaa gaaatccgga tctattgcat   1140
tgttgcaaga atttgagaga gtggttggtg ctgaaggagg tgctgctgct gcagttgttg   1200
gatgcaagtg catggggaag tgcaagagtg cacctaatgt gaggattcag aactctactg   1260
cagataaaat agctgagggg ttcaatgatt cagttaaggt tccagctaac cctctttgca   1320
ttggggttgc atggaggatg ttgaaaccat tgtggcttag attcttgggc gagaatcagg   1380
aaagtactaa tgaataattt gctggtatgc tgtttggaaa attgtatata cgtagtgcca   1440
gaacctatca gattgttgtt ttatttata taaacataga ctgcatattg ttgtgagatt   1500
cgatttcctc atttattgga acttccagag cctgatttgt gtccattcga gctcgactca   1560
aagatttaca tggcctgctc aatctatgaa ttcaaatttg agggccctgt ttggcattaa   1620
tattaatata ttaatat                                                  1637
```

<210> SEQ ID NO 80
<211> LENGTH: 345
<212> TYPE: PRT
<213> ORGANISM: Arachis hypogaea

<400> SEQUENCE: 80

```
Met Glu Val Ser Gly Ala Val Leu Arg Asn Val Thr Cys Pro Ser Phe
1               5                   10                  15

Ser Val His Val Ser Ser Arg Arg Gly Gly Asp Ser Cys Val Thr
            20                  25                  30

Val Pro Val Arg Met Arg Lys Lys Ala Val Val Arg Cys Cys Cys Gly
        35                  40                  45

Phe Ser Asp Ser Gly His Val Gln Tyr Tyr Gly Asp Glu Lys Lys Lys
    50                  55                  60

Glu Asn Gly Thr Ala Met Leu Ser Thr Lys Lys Leu Lys Met Leu
65                  70                  75                  80

Lys Lys Arg Val Leu Phe Asp Asp Leu Gln Gly Asn Leu Thr Trp Asp
            85                  90                  95
```

Ala Ala Met Val Leu Met Lys Gln Leu Glu Gln Val Arg Ala Glu Glu
                100                 105                 110

Lys Glu Leu Lys Lys Arg Lys Gln Glu Lys Lys Glu Ala Lys Leu
            115                 120                 125

Lys Ala Ser Lys Met Asn Thr Asn Pro Asp Cys Glu Ser Ser Ser
130                 135                 140

Ser Ser Ser Ser Glu Ser Glu Ser Glu Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His Asn Ala
            195                 200                 205

Val Glu Leu Phe Ser Arg Asn Asn Asp Ile Ser Val Gly Ser Ile Asn
210                 215                 220

Gly Gly Leu Lys Asn Glu Asn Thr Ala Val Ile Thr Thr Glu Ala Ile
225                 230                 235                 240

Pro Gln Lys Arg Ile Glu Val Cys Met Gly Asn Lys Cys Lys Lys Ser
                245                 250                 255

Gly Ser Ile Ala Leu Leu Gln Glu Phe Glu Arg Val Val Gly Ala Glu
            260                 265                 270

Gly Gly Ala Ala Ala Val Gly Cys Lys Cys Met Gly Lys Cys
            275                 280                 285

Lys Ser Ala Pro Asn Val Arg Ile Gln Asn Ser Thr Ala Asp Lys Ile
            290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
            340                 345

<210> SEQ ID NO 81
<211> LENGTH: 1494
<212> TYPE: DNA
<213> ORGANISM: Artificial Sequence
<220> FEATURE:
<223> OTHER INFORMATION: Euonymus alatus DGAT fused at N-terminus to
      G6P/Pi-Tporter targeting signal and 1TM domain (EaDGAT/1TM)

<400> SEQUENCE: 81
atgagactat tggtacttgg tctcgtgtcc ctcggggtca cgggctttgc ccacacgcac      60
cctcgtctgt tgtccaagat tccgggagcc agtctcaaag gacgcccctg tttcgcggag     120 ccccctctg gtcctacctc ccgctccttc tctctgcctc ggagccgaac cgcggctctt      180
acatccgtag agccgagtgt gtataatttg caacctaccc cggttgtagc gccgaaactt     240
ttggtcagca gacgcggggg agcagttgcg acagctactg gatcagatgc tggagtcaag     300
cagaccttga agtgggctc tttcttcttt ctttggtatt tgttcaacat cggctacaat     360
atctataaca agaaagccct caatgtgctg ccgctgccgt ggatgatgga tgctcatcaa     420
gagatcaaga acttcatcaa ggtttgggta caagccatgg tatgtctatc ttacgcttac     480
tacttctcct caagacttcc aaaaggactc ttaaggttac tctctttact tcctgtcctt     540
tatctcctat taatcgctcc cttgaacatc tcttcttca ttctttcatc aatcaccggc     600

```
ttcttccttg cttggctaac aacattcaag gtcatctctt ttgcctttga tcaaggccct    660
ttgtatccac tcccacaaaa cctcctacat ttcatctcaa tagcttgtct tcccatcaca    720
atcaagcgaa acccatcacc aaaattgaaa tccacaacaa acccatctcc aatttcacat    780
cttttgaaaa aggcattcat gtcatttcca tctaaagtct tgttccattg ggtcattgct    840
catctctacc aatacaaaaa gtacatggat ccaaacgtgg tcttagtgat ctattgttgt    900
catgtgtacg ttatgttgga tatctcactc tctctatgtg caaccctagc tgaattcctt    960
tgtgggtttg atgttgaacc acaattcaaa gagccttacc ttgctacttc actacaagac   1020
ttttggggcc gtaggtggaa cataattgtg tcaagtgtcc tacgttcgac tgtctatgcc   1080
ccaactagaa acattgcttc atatctaatt gggtctagat gggcttattt tccagctata   1140
attgcaacat ttgtcgtatc aggagttatg catgatgtag tgtactatgt gtacatgatg   1200
catatgtatc ccaagtggga tatgacaggg cacttcgtcc tacatgggat ttgtgaagct   1260
ttggaggtgg agatgaagtg taagagatca aggagtgaca agtggcggcg gcatccagct   1320
gtcgattggg taatggtgat ggggtttgtg atggggacta gtgtttcctt actctttgtg   1380
ccactattaa gggataatgt ggaccaaatt gtagcagaag agtactcaat tttgtttaat   1440
tttgtgaggg agaagattgt catgcttgga acaaggtttg tgtgtggaaa ttga         1494
```

<210> SEQ ID NO 82
<211> LENGTH: 497
<212> TYPE: PRT
<213> ORGANISM: Artificial Sequence
<220> FEATURE:
<223> OTHER INFORMATION: Euonymus alatus DGAT fused at N-terminus to
      G6P/Pi-Tporter targeting signal and 1TM domain (EaDGAT/1TM)

<400> SEQUENCE: 82

Met Arg Leu Leu Val Leu Gly Leu Val Ser Leu Gly Val Thr Gly Phe
1               5                   10                  15

Ala His Thr His Pro Arg Leu Leu Ser Lys Ile Pro Gly Ala Ser Leu
            20                  25                  30

Lys Gly Arg Pro Cys Phe Ala Glu Pro Pro Ser Gly Pro Thr Ser Arg
        35                  40                  45

Ser Phe Ser Leu Pro Arg Ser Arg Thr Ala Ala Leu Thr Ser Val Glu
    50                  55                  60

Pro Ser Val Tyr Asn Leu Gln Pro Thr Pro Val Ala Pro Lys Leu
65                  70                  75                  80

Leu Val Ser Arg Arg Gly Gly Ala Val Ala Thr Ala Thr Gly Ser Asp
                85                  90                  95

Ala Gly Val Lys Gln Thr Leu Lys Val Gly Ser Phe Phe Leu Trp
            100                 105                 110

Tyr Leu Phe Asn Ile Gly Tyr Asn Ile Tyr Asn Lys Lys Ala Leu Asn
        115                 120                 125

Val Leu Pro Leu Pro Trp Met Met Asp Ala His Gln Glu Ile Lys Asn
    130                 135                 140

Phe Ile Lys Val Trp Val Gln Ala Met Val Cys Leu Ser Tyr Ala Tyr
145                 150                 155                 160

Tyr Phe Ser Ser Arg Leu Pro Lys Gly Leu Leu Arg Leu Leu Ser Leu
                165                 170                 175

Leu Pro Val Leu Tyr Leu Leu Ile Ala Pro Leu Asn Ile Ser Ser
            180                 185                 190

Phe Ile Leu Ser Ser Ile Thr Gly Phe Phe Leu Ala Trp Leu Thr Thr

```
                 195                 200                 205
    Phe Lys Val Ile Ser Phe Ala Phe Asp Gln Gly Pro Leu Tyr Pro Leu
    210                 215                 220

Pro Gln Asn Leu Leu His Phe Ile Ser Ile Ala Cys Leu Pro Ile Thr
225                 230                 235                 240

Ile Lys Arg Asn Pro Ser Pro Lys Leu Lys Ser Thr Thr Asn Pro Ser
                    245                 250                 255

Pro Ile Ser His Leu Leu Lys Lys Ala Phe Met Ser Phe Pro Ser Lys
                    260                 265                 270

Val Leu Phe His Trp Val Ile Ala His Leu Tyr Gln Tyr Lys Lys Tyr
                    275                 280                 285

Met Asp Pro Asn Val Val Leu Val Ile Tyr Cys Cys His Val Tyr Val
    290                 295                 300

Met Leu Asp Ile Ser Leu Ser Leu Cys Ala Thr Leu Ala Glu Phe Leu
305                 310                 315                 320

Cys Gly Phe Asp Val Glu Pro Gln Phe Lys Glu Pro Tyr Leu Ala Thr
                    325                 330                 335

Ser Leu Gln Asp Phe Trp Gly Arg Arg Trp Asn Ile Ile Val Ser Ser
                    340                 345                 350

Val Leu Arg Ser Thr Val Tyr Ala Pro Thr Arg Asn Ile Ala Ser Tyr
                    355                 360                 365

Leu Ile Gly Ser Arg Trp Ala Tyr Phe Pro Ala Ile Ile Ala Thr Phe
    370                 375                 380

Val Val Ser Gly Val Met His Asp Val Tyr Tyr Val Tyr Met Met
385                 390                 395                 400

His Met Tyr Pro Lys Trp Asp Met Thr Gly His Phe Val Leu His Gly
                    405                 410                 415

Ile Cys Glu Ala Leu Glu Val Glu Met Lys Cys Lys Arg Ser Arg Ser
                    420                 425                 430

Asp Lys Trp Arg Arg His Pro Ala Val Asp Trp Val Met Val Met Gly
                    435                 440                 445

Phe Val Met Gly Thr Ser Val Ser Leu Leu Phe Val Pro Leu Leu Arg
    450                 455                 460

Asp Asn Val Asp Gln Ile Val Ala Glu Glu Tyr Ser Ile Leu Phe Asn
465                 470                 475                 480

Phe Val Arg Glu Lys Ile Val Met Leu Gly Thr Arg Phe Val Cys Gly
                    485                 490                 495

Asn

<210> SEQ ID NO 83
<211> LENGTH: 1560
<212> TYPE: DNA
<213> ORGANISM: Artificial Sequence
<220> FEATURE:
<223> OTHER INFORMATION: Euonymus alatus DGAT fused at N-terminus to
      G6P/Pi-Tporter targeting signal and 2TM domain (EaDGAT/2TM)

<400> SEQUENCE: 83
atgagactat tggtacttgg tctcgtgtcc ctcggggtca cgggctttgc ccacacgcac        60
cctcgtctgt tgtccaagat tccgggagcc agtctcaaag acgccctg tttcgcggag         120 cccccctctg gtcctacctc ccgctccttc tctctgcctc ggagccgaac cgcggctctt       180
acatccgtag agccgagtgt gtataatttg caacctaccc cggttgtagc gccgaaactt       240
ttggtcagca gacgcggggg agcagttgcg acagctactg gatcagatgc tggagtcaag       300
```

-continued

```
cagaccttga aagtgggctc tttcttcttt ctttggtatt tgttcaacat cggctacaat    360
atctataaca agaaagccct caatgtgctg ccgctgccgt ggatggtggg tttggtccag    420
ctctctctcg gcttgcttta tgtcttccct ttgtggcttt ttgggatcat gatggatgct    480
catcaagaga tcaagaactt catcaaggtt tgggtacaag ccatggtatg tctatcttac    540
gcttactact tctcctcaag acttccaaaa ggactcttaa ggttactctc tttacttcct    600
gtcctttatc tcctattaat cgctcccttg aacatctctt ctttcattct ttcatcaatc    660
accggcttct tccttgcttg gctaacaaca ttcaaggtca tctcttttgc ctttgatcaa    720 ggcccttttgt atccactccc acaaaacctc ctacatttca tctcaatagc ttgtcttccc    780
atcacaatca agcgaaaccc atcaccaaaa ttgaaatcca acaaacccc atctccaatt    840 tcacatcttt tgaaaaggc attcatgtca tttccatcta aagtcttgtt ccattgggtc    900
attgctcatc tctaccaata caaaagtac atggatccaa acgtggtctt agtgatctat    960
tgttgtcatg tgtacgttat gttggatatc tcactctctc tatgtgcaac cctagctgaa   1020
ttcctttgtg ggtttgatgt tgaaccacaa ttcaaagagc cttaccttgc tacttcacta   1080
caagactttt ggggccgtag gtggaacata attgtgtcaa gtgtcctacg ttcgactgtc   1140
tatgccccaa ctagaaacat tgcttcatat ctaattgggt ctagatgggc ttatttttcca   1200 gctataattg caacatttgt cgtatcagga gttatgcatg atgtagtgta ctatgtgtac   1260
atgatgcata tgtatcccaa gtgggatatg acagggcact cgtcctaca tgggatttgt   1320 gaagctttgg aggtggagat gaagtgtaag agatcaagga gtgacaagtg gcggcggcat   1380
ccagctgtcg attgggtaat ggtgatgggg tttgtgatgg ggactagtgt ttccttactc   1440
tttgtgccac tattaaggga taatgtggac caaattgtag cagaagagta ctcaattttg   1500 tttaatttg tgagggagaa gattgtcatg cttggaacaa ggtttgtgtg tggaaattga   1560
```

<210> SEQ ID NO 84
<211> LENGTH: 519
<212> TYPE: PRT
<213> ORGANISM: Artificial Sequence
<220> FEATURE:
<223> OTHER INFORMATION: Euonymus alatus DGAT fused at N-terminus to
      G6P/Pi-Tporter targeting signal and 2TM domain (EaDGAT/2TM)

<400> SEQUENCE: 84

```
Met Arg Leu Leu Val Leu Gly Leu Val Ser Leu Gly Val Thr Gly Phe
1               5                   10                  15

Ala His Thr His Pro Arg Leu Leu Ser Lys Ile Pro Gly Ala Ser Leu
            20                  25                  30

Lys Gly Arg Pro Cys Phe Ala Glu Pro Pro Ser Gly Pro Thr Ser Arg
        35                  40                  45

Ser Phe Ser Leu Pro Arg Ser Arg Thr Ala Ala Leu Thr Ser Val Glu
    50                  55                  60

Pro Ser Val Tyr Asn Leu Gln Pro Thr Pro Val Val Ala Pro Lys Leu
65                  70                  75                  80

Leu Val Ser Arg Arg Gly Gly Ala Val Ala Thr Ala Thr Gly Ser Asp
                85                  90                  95

Ala Gly Val Lys Gln Thr Leu Lys Val Gly Ser Phe Phe Phe Leu Trp
            100                 105                 110

Tyr Leu Phe Asn Ile Gly Tyr Asn Ile Tyr Asn Lys Lys Ala Leu Asn
        115                 120                 125

Val Leu Pro Leu Pro Trp Met Val Gly Leu Val Gln Leu Ser Leu Gly
    130                 135                 140
```

Leu Leu Tyr Val Phe Pro Leu Trp Leu Phe Gly Ile Met Met Asp Ala
145                 150                 155                 160

His Gln Glu Ile Lys Asn Phe Ile Lys Val Trp Val Gln Ala Met Val
            165                 170                 175

Cys Leu Ser Tyr Ala Tyr Tyr Phe Ser Ser Arg Leu Pro Lys Gly Leu
            180                 185                 190

Leu Arg Leu Leu Ser Leu Leu Pro Val Leu Tyr Leu Leu Leu Ile Ala
        195                 200                 205

Pro Leu Asn Ile Ser Ser Phe Ile Leu Ser Ser Ile Thr Gly Phe Phe
210                 215                 220

Leu Ala Trp Leu Thr Thr Phe Lys Val Ile Ser Phe Ala Phe Asp Gln
225                 230                 235                 240

Gly Pro Leu Tyr Pro Leu Pro Gln Asn Leu Leu His Phe Ile Ser Ile
                245                 250                 255

Ala Cys Leu Pro Ile Thr Ile Lys Arg Asn Pro Ser Pro Lys Leu Lys
            260                 265                 270

Ser Thr Thr Asn Pro Ser Pro Ile Ser His Leu Leu Lys Lys Ala Phe
        275                 280                 285

Met Ser Phe Pro Ser Lys Val Leu Phe His Trp Val Ile Ala His Leu
290                 295                 300

Tyr Gln Tyr Lys Lys Tyr Met Asp Pro Asn Val Val Leu Val Ile Tyr
305                 310                 315                 320

Cys Cys His Val Tyr Val Met Leu Asp Ile Ser Leu Ser Leu Cys Ala
                325                 330                 335

Thr Leu Ala Glu Phe Leu Cys Gly Phe Asp Val Glu Pro Gln Phe Lys
            340                 345                 350

Glu Pro Tyr Leu Ala Thr Ser Leu Gln Asp Phe Trp Gly Arg Arg Trp
        355                 360                 365

Asn Ile Ile Val Ser Ser Val Leu Arg Ser Thr Val Tyr Ala Pro Thr
370                 375                 380

Arg Asn Ile Ala Ser Tyr Leu Ile Gly Ser Arg Trp Ala Tyr Phe Pro
385                 390                 395                 400

Ala Ile Ile Ala Thr Phe Val Val Ser Gly Val Met His Asp Val Val
                405                 410                 415

Tyr Tyr Val Tyr Met Met His Met Tyr Pro Lys Trp Asp Met Thr Gly
            420                 425                 430

His Phe Val Leu His Gly Ile Cys Glu Ala Leu Glu Val Glu Met Lys
        435                 440                 445

Cys Lys Arg Ser Arg Ser Asp Lys Trp Arg Arg His Pro Ala Val Asp
450                 455                 460

Trp Val Met Val Met Gly Phe Val Met Gly Thr Ser Val Ser Leu Leu
465                 470                 475                 480

Phe Val Pro Leu Leu Arg Asp Asn Val Asp Gln Ile Val Ala Glu Glu
                485                 490                 495

Tyr Ser Ile Leu Phe Asn Phe Val Arg Glu Lys Ile Val Met Leu Gly
            500                 505                 510

Thr Arg Phe Val Cys Gly Asn
        515

<210> SEQ ID NO 85
<211> LENGTH: 1161
<212> TYPE: DNA
<213> ORGANISM: Artificial Sequence
<220> FEATURE:

<223> OTHER INFORMATION: ER targeting signal and Mus musculus DGAT2
      truncated by 55 amino acid residues

<400> SEQUENCE: 85

| | | |
|---|---|---|
| atgatgttca tgcgaatcgc cgtcgccgct ctggccttgc tggcagcgcc atcgatcagg | 60 |
| gccgaggagg ctggcgagga ggcgaaaatg ggcactgtgg gtggaggcag ctacccttat | 120 |
| gatgttcccg actacgctgg cggtgggtcg gtgacgtggc tcaaccgcag caaggtggag | 180 |
| aaacaattgc aagttatctc tgtccttcag tgggtcctca gctttctcgt gctcggggtg | 240 |
| gcctgctctg tcatcttgat gtatacgttc tgcacagatt gttggctcat cgcggtgttg | 300 |
| tacttcacct ggcttgcatt cgactggaac ccccccaaaa agggtggtcg ccggtcgcag | 360 |
| tgggtgcgca attgggccgt gtggcggtac ttccgcgact acttccctat tcaattggtc | 420 |
| aaaacccata acttgctcac tacccggaac tacatctttg ctaccatcc gcacgggatc | 480 |
| atggggcttg gtgcgttctg caacttttcg acggaagcca cggaagtgtc caagaagttc | 540 |
| cccggcattc gtccttactt ggccaccctc gcgggcaact tccgtatgcc tgtgttgcga | 600 |
| gagtacctga tgtccggggg aatttgtccc gttaatcgtg acaccatcga ctaccttctc | 660 |
| tccaagaatg gctctggcaa cgcaatcatc attgtggtcg gcggagctgc tgagtccctc | 720 |
| tcctcgatgc cgggaaagaa tgcagttact ctcaagaatc gcaagggctt tgtgaagctg | 780 |
| gccctgcggc acggtgccga tctggtgccc acgtacagct ttggcgagaa cgaggtgtac | 840 |
| aagcaggtca tctttgaaga gggaagctgg ggcaggtggg tccagaaaaa gttccagaag | 900 |
| tacatcgggt tcgctcccctg catttttccac gggcgtggcc tgttttcctc cgacacgtgg | 960 |
| gggctggtgc cttatagcaa gccgattacc accgtggtcg gagagccaat tacggtcccg | 1020 |
| aaactggagc atcccactca aaaggacatt gatctttatc acgcgatgta tatggaagcg | 1080 |
| ttggtgaagc tgtttgataa ccataagacc aagttcgggc ttcccgaaac agaagtgctg | 1140 |
| gaggtcaacg acgacgagtt g | 1161 |

<210> SEQ ID NO 86
<211> LENGTH: 387
<212> TYPE: PRT
<213> ORGANISM: Artificial Sequence
<220> FEATURE:
<223> OTHER INFORMATION: ER targeting signal and Mus musculus DGAT2
      truncated by 55 amino acid residues

<400> SEQUENCE: 86

Met Met Phe Met Arg Ile Ala Val Ala Ala Leu Ala Leu Leu Ala Ala
1               5                   10                  15

Pro Ser Ile Arg Ala Glu Glu Ala Gly Glu Glu Ala Lys Met Gly Thr
            20                  25                  30

Val Gly Gly Gly Ser Tyr Pro Tyr Asp Val Pro Asp Tyr Ala Gly Gly
        35                  40                  45

Gly Ser Val Thr Trp Leu Asn Arg Ser Lys Val Glu Lys Gln Leu Gln
    50                  55                  60

Val Ile Ser Val Leu Gln Trp Val Leu Ser Phe Leu Val Leu Gly Val
65                  70                  75                  80

Ala Cys Ser Val Ile Leu Met Tyr Thr Phe Cys Thr Asp Cys Trp Leu
                85                  90                  95

Ile Ala Val Leu Tyr Phe Thr Trp Leu Ala Phe Asp Trp Asn Thr Pro
            100                 105                 110

Lys Lys Gly Gly Arg Arg Ser Gln Trp Val Arg Asn Trp Ala Val Trp
        115                 120                 125

```
Arg Tyr Phe Arg Asp Tyr Phe Pro Ile Gln Leu Val Lys Thr His Asn
            130                 135                 140

Leu Leu Thr Thr Arg Asn Tyr Ile Phe Gly Tyr His Pro His Gly Ile
145                 150                 155                 160

Met Gly Leu Gly Ala Phe Cys Asn Phe Ser Thr Glu Ala Thr Glu Val
                165                 170                 175

Ser Lys Lys Phe Pro Gly Ile Arg Pro Tyr Leu Ala Thr Leu Ala Gly
                180                 185                 190

Asn Phe Arg Met Pro Val Leu Arg Glu Tyr Leu Met Ser Gly Gly Ile
            195                 200                 205

Cys Pro Val Asn Arg Asp Thr Ile Asp Tyr Leu Leu Ser Lys Asn Gly
            210                 215                 220

Ser Gly Asn Ala Ile Ile Ile Val Val Gly Ala Ala Glu Ser Leu
225                 230                 235                 240

Ser Ser Met Pro Gly Lys Asn Ala Val Thr Leu Lys Asn Arg Lys Gly
                245                 250                 255

Phe Val Lys Leu Ala Leu Arg His Gly Ala Asp Leu Val Pro Thr Tyr
                260                 265                 270

Ser Phe Gly Glu Asn Glu Val Tyr Lys Gln Val Ile Phe Glu Glu Gly
            275                 280                 285

Ser Trp Gly Arg Trp Val Gln Lys Lys Phe Gln Lys Tyr Ile Gly Phe
290                 295                 300

Ala Pro Cys Ile Phe His Gly Arg Gly Leu Phe Ser Ser Asp Thr Trp
305                 310                 315                 320

Gly Leu Val Pro Tyr Ser Lys Pro Ile Thr Thr Val Val Gly Glu Pro
                325                 330                 335

Ile Thr Val Pro Lys Leu Glu His Pro Thr Gln Lys Asp Ile Asp Leu
            340                 345                 350

Tyr His Ala Met Tyr Met Glu Ala Leu Val Lys Leu Phe Asp Asn His
            355                 360                 365

Lys Thr Lys Phe Gly Leu Pro Glu Thr Glu Val Leu Glu Val Asn Asp
            370                 375                 380

Asp Glu Leu
385

<210> SEQ ID NO 87
<211> LENGTH: 7
<212> TYPE: PRT
<213> ORGANISM: Artificial Sequence
<220> FEATURE:
<223> OTHER INFORMATION: Eukaryotic DGAT1 consensus motif
<220> FEATURE:
<221> NAME/KEY: DOMAIN
<222> LOCATION: (1)..(7)
<223> OTHER INFORMATION: X can be any amino acid residue

<400> SEQUENCE: 87

Phe Tyr Xaa Asp Trp Trp Asn
1               5
```